(12) United States Patent
Van Berkel et al.

(10) Patent No.: US 11,596,696 B2
(45) Date of Patent: Mar. 7, 2023

(54) COMBINATION THERAPY WITH AN ANTI-CD25 ANTIBODY-DRUG CONJUGATE

(71) Applicants: ADC Therapeutics SA, Epalinges (CH); Medimmune Limited, Cambridge (GB)

(72) Inventors: Patricius Hendrikus Cornelis Van Berkel, Epalinges (CH); Lisa Skelton, Epalinges (CH); Francesca Zammarchi, Epalinges (CH); Jay Marshall Feingold, Murray Hill, NJ (US); Jens Wuerthner, Epalinges (CH); John Hartley, London (GB)

(73) Assignees: ADC THERAPEUTICS SA, Epalinges (CH); MEDIMMUNE LIMITED, Cambridge (GB)

(*) Notice: Subject to any disclaimer, the term of this patent is extended or adjusted under 35 U.S.C. 154(b) by 131 days.

(21) Appl. No.: 16/605,708

(22) PCT Filed: Apr. 20, 2018

(86) PCT No.: PCT/EP2018/060214
§ 371 (c)(1),
(2) Date: Oct. 16, 2019

(87) PCT Pub. No.: WO2018/193104
PCT Pub. Date: Oct. 25, 2018

(65) Prior Publication Data
US 2022/0016259 A1 Jan. 20, 2022

(30) Foreign Application Priority Data

Apr. 20, 2017 (GB) .................................... 1706245
Apr. 20, 2017 (GB) .................................... 1706246
(Continued)

(51) Int. Cl.
*A61K 47/68* (2017.01)
*A61K 31/5517* (2006.01)
(Continued)

(52) U.S. Cl.
CPC ...... *A61K 47/6849* (2017.08); *A61K 31/5517* (2013.01); *A61K 31/7068* (2013.01);
(Continued)

(58) Field of Classification Search
None
See application file for complete search history.

(56) References Cited

U.S. PATENT DOCUMENTS 4,816,567 A  3/1989 Cabilly et al.
6,383,487 B1  5/2002 Amlot et al.
(Continued)

FOREIGN PATENT DOCUMENTS

WO  2007005874 A2  1/2007
WO  2014057118 A1  4/2014
(Continued)

OTHER PUBLICATIONS

Arce Vargas et al., "Fc-Optimized Anti-CD25 Depletes Tumor-Infiltrating Regulatory T Cells and Synergizes with PD-1 Blockade to Eradicate Established Tumors," Immunity 46(4):577-586 (2017).
(Continued)

*Primary Examiner* — Karl J Puttlitz
(74) *Attorney, Agent, or Firm* — Medler Ferro Woodhouse & Mills PLLC

(57) ABSTRACT

The present disclosure relates to combination therapies for the treatment of pathological conditions, such as cancer. In particular, the present disclosure relates to combination
(Continued)

therapies comprising treatment with an Antibody Drug Conjugate (ADC) and a secondary agent.

13 Claims, 11 Drawing Sheets

Specification includes a Sequence Listing.

(30) Foreign Application Priority Data

| | | | |
|---|---|---|---|
| Apr. 20, 2017 | (GB) | ..................................... | 1706247 |
| Apr. 20, 2017 | (GB) | ..................................... | 1706248 |
| Apr. 20, 2017 | (GB) | ..................................... | 1706249 |
| Apr. 20, 2017 | (GB) | ..................................... | 1706250 |
| Apr. 20, 2017 | (GB) | ..................................... | 1706251 |
| Apr. 20, 2017 | (GB) | ..................................... | 1706252 |
| Mar. 29, 2018 | (GB) | ..................................... | 1805189 |

(51) Int. Cl.
  *A61K 31/7068* (2006.01)
  *A61K 31/7076* (2006.01)
  *C07K 16/28* (2006.01)

(52) U.S. Cl.
  CPC ...... *A61K 31/7076* (2013.01); *A61K 47/6803* (2017.08); *C07K 16/2818* (2013.01); *C07K 16/2827* (2013.01); *C07K 16/2878* (2013.01)

(56) References Cited

U.S. PATENT DOCUMENTS

| | | | |
|---|---|---|---|
| 7,438,907 | B2 | 10/2008 | Schuurman et al. |
| 7,803,839 | B2 | 9/2010 | Aay et al. |
| 7,812,135 | B2 | 10/2010 | Smith et al. |
| 8,591,886 | B2 | 11/2013 | Ponath et al. |
| 8,609,089 | B2 | 12/2013 | Langermann et al. |
| 8,709,424 | B2 | 4/2014 | Schebye et al. |
| 8,735,553 | B1 | 5/2014 | Li et al. |
| 8,907,053 | B2 | 12/2014 | Sasikumar et al. |
| 9,205,148 | B2 | 11/2015 | Langermann et al. |
| 9,738,723 | B2 | 8/2017 | Hammond et al. |
| 9,834,606 | B2 | 12/2017 | Li et al. |
| 9,919,056 | B2 | 3/2018 | Van Berkel et al. |
| 9,931,414 | B2 | 4/2018 | Van Berkel et al. |
| 9,950,078 | B2 | 4/2018 | Howard et al. |
| 9,956,299 | B2 | 5/2018 | Howard et al. |
| 9,975,957 | B2 | 5/2018 | Du et al. |
| 10,010,624 | B2 | 7/2018 | Howard et al. |
| 10,017,580 | B2 | 7/2018 | Van Berkel et al. |
| 10,081,681 | B2 | 9/2018 | Korman et al. |
| 10,259,882 | B2 | 4/2019 | Van Dijk et al. |
| 10,479,838 | B2 | 11/2019 | Ravetch et al. |
| 10,544,225 | B2 | 1/2020 | Li et al. |
| 10,690,674 | B2 | 6/2020 | Wang et al. |
| 10,695,433 | B2 | 6/2020 | Van Berkel et al. |
| 10,736,903 | B2 | 8/2020 | Van Berkel et al. |
| 10,751,346 | B2 | 8/2020 | Van Berkel et al. |
| 10,780,096 | B2 | 9/2020 | Van Berkel et al. |
| 10,946,093 | B2 | 3/2021 | Junttila |
| 10,983,128 | B2 | 4/2021 | Bahjat et al. |
| 2015/0190506 | A1 | 7/2015 | Cheung et al. |
| 2015/0273077 | A1 | 10/2015 | Van Berkel et al. |
| 2015/0290316 | A1 | 10/2015 | Graziano et al. |
| 2016/0009805 | A1 | 1/2016 | Kowanetz et al. |
| 2016/0160290 | A1 | 6/2016 | Huseni |
| 2016/0166685 | A1 | 6/2016 | Cheung et al. |
| 2016/0256561 | A1 | 9/2016 | Howard et al. |
| 2016/0304607 | A1 | 10/2016 | Sadineni et al. |
| 2016/0034784 | A1 | 12/2016 | Hammond et al. |
| 2018/0086828 | A1 | 3/2018 | Van Berkel et al. |
| 2018/0092985 | A1 | 4/2018 | Van Berkel et al. |
| 2018/0092986 | A1 | 4/2018 | Van Berkel et al. |
| 2018/0099055 | A1 | 4/2018 | Van Berkel et al. |
| 2018/0117172 | A1 | 5/2018 | Van Berkel et al. |
| 2018/0125994 | A1 | 5/2018 | Van Berkel et al. |
| 2018/0127505 | A1 | 5/2018 | Van Berkel et al. |
| 2018/0142025 | A1 | 5/2018 | Van Berkel |
| 2018/0303953 | A1 | 10/2018 | Van Berkel et al. |
| 2020/0405873 | A1 | 12/2020 | Feingold et al. |

FOREIGN PATENT DOCUMENTS

| | | | |
|---|---|---|---|
| WO | 2014057119 | * | 4/2014 |
| WO | 2016166305 | A1 | 10/2016 |
| WO | 2016177438 | A1 | 11/2016 |

OTHER PUBLICATIONS

Babb et al., "Cancer phase I clinical trials: efficient dose escalation with overdose control," Statistics in Medicine 17(10):1103-1120 (1998).

Borch et al., "Reorienting the immune system in the treatment of cancer by using anti-PD-1 and anti-PD-L1 antibodies," Drug Discovery Today 20(9):1127-1134 (2015).

Brown et al., "Blockade of Programmed Death-1 Ligands on Dendritic Cells Enhances T Cell Activation and Cytokine Production," Journal of Immunology 170(3):1257-1266 (2003).

Carter, P., "Potent antibody therapeutics by design," Nature Reviews Immunology 6(5):343-357 (2006).

Clackson et al., "Making antibody fragments using phage display libraries," Nature, 352:624-628 (1991).

Cuzzocrea et al., "Glucocorticoid-induced TNF receptor family gene (GITR) knockout mice exhibit a resistance to splanchnic artery occlusion (SAO) shock," Journal of Leukocyte Biology, 76(5):933-940 (2004).

Cuzzocrea et al., "Proinflammatory role of glucocorticoid-induced TNF receptor-related gene in acute lung inflammation," Journal of Immunology, 177(1):631-641 (2006).

Cuzzocrea et al., "Genetic and pharmacological inhibition of GITR-GITRL interaction reduces chronic lung injury induced by bleomycin instillation," FASEB Journal, 21(1):117-129 (2007).

Dong et al., "Tumor-associated B7-H1 promotes T-cell apoptosis: A potential mechanism of immune evasion," Nature Medicine 8(8):793-800 (2002).

Fielding A. "Current treatment of Philadelphia chromosome-positive acute lymphoblastic leukemia," Haematologica 95(1):8-12 (2010).

Flynn et al. "ADCT-301, a Pyrrolobenzodiazepine (PBD) Dimer-Containing Antibody-Drug Conjugate (ADC) Targeting CD25-Expressing Hematological Malignancies," Molecular Cancer Therapeutics 15(11):2709-2721 (2016).

Gonzalez et al. "Abstract 3204: INCAGN01949: an anti-OX40 agonist antibody with the potential to enhance tumor-specific T-cell responsiveness, while selectively depleting intratumoral regulatory T cells" Cancer Research 76(14_Supplement):3204 (2016).

Hamann P. "Monoclonal antibody-drug conjugates," Expert Opinion on Therapeutic Patents 15(9):1087-1103 (2005).

Hartley J., "The development of pyrrolobenzodiazepines as antitumour agents," Expert Opinion on Investigational Drugs 20(6):733-744 (2011).

Horwood et al., "Bruton's Tyrosine Kinase is Required for TLR2 and TLR4-Induced TNF, but not IL-6, Production," Journal of Immunology 176(6):3635-3641 (2006).

Ko et al., "Treatment of advanced tumors with agonistic anti-GITR mAb and its effects on tumor-infiltrating Foxp3+CD25+CD4+ regulatory T cells," Journal of Experimental Medicine 202(7):885-891 (2005).

Kohler et al., "Continuous cultures of fused cells secreting antibody of predefined specificity," Nature 256:495-497 (1975).

Kovtun et al., "Antibody-Drug Conjugates Designed to Eradicate Tumors with Homogeneous and Heterogeneous Expression of the Target Antigen," Cancer Research 66(6):3214-3221 (2006).

Lambert J., "Drug-conjugated monoclonal antibodies for the treatment of cancer," Current Opinion in Pharmacology 5(5):543-549 (2005).

(56) References Cited

OTHER PUBLICATIONS

Law et al., "Lymphocyte Activation Antigen CD70 Expressed by Renal Cell Carcinoma is a Potential Therapeutic Target for Anti-CD70 Antibody-Drug Conjugates," Cancer Research 66(4):2328-2337 (2006).
Levi et al., "Detection of interleukin-2 receptors on tumor cells in formalin-fixed, paraffin-embedded tissues," Applied Immunohistochemistry 5(4):234-238 (1997).
Li et al., "A Mini-Review for Cancer Immunotherapy: Molecular Understanding of PD-1/PD-L1 Pathway & Translational Blockade of Immune Checkpoints," International Journal of Molecular Sciences 17(7):1151 (2016).
Lin et al., "The PD-1/PD-L1 complex resembles the antigen-binding Fv domains of antibodies and T cell receptors" Proceedings of the National Academy of Sciences 105(8):3011-3016 (2008).
Lonberg N., "Fully human antibodies from transgenic mouse and phage display platforms," Current Opinion in Immunology 20(4):450-459 (2008).
Marks et al., "By-passing Immunization, Human Antibodies from V-gene Libraries Displayed on Phage," Journal of Molecular Biology 222(3):581-597 (1991).
Menon et al., "Advances in Cancer Immunotherapy in Solid Tumors," Cancers 8(12):106 (2016).
Ménétrier-Caux et al., "Targeting regulatory T cells," Targeted Oncology 7(1):15-28 (2012).
Merz et al., "ImmunoMax. A maximized immunohistochemical method for the retrieval and enhancement of hidden antigens," Laboratory Investigation 73(1):149-156 (1995).
Miller et al., "Design, Construction, and In Vitro Analyses of Multivalent Antibodies," Journal of Immunology 170(9):4854-4861 (2003).
Morrison et al., "Chimeric human antibody molecules: Mouse antigen-binding domains with human constant region domains," Proc. Natl. Acad. Sci. USA, 81(21):6851-6855 (1984).
Neuenschwander et al. "Critical aspects of the Bayesian approach to phase I cancer trials," Statistics in Medicine 27(13):2420-2439 (2008).
Nocentini et al. "A new member of the tumor necrosis factor/nerve growth factor receptor family inhibits T cell receptor-induced apoptosis," Proceedings of the National Academy of Sciences 94(12):6216-6221 (1997).
Nomi et al. "Clinical significance and therapeutic potential of the programmed death-1 ligand/programmed death-1 pathway in human pancreatic cancer," Clinical Cancer Research 13(7):2151-2157 (2007).
Okazaki et al., "PD-1 and PD-1 ligands: from discovery to clinical application," International Immunology 19(7):813-824 (2007).
Pardoll D. "The blockade of immune checkpoints in cancer immunotherapy," Nature Reviews Cancer 12(4):252-264 (2012).
Pavlasova et al. "Ibrutinib inhibits CD20 upregulation on CLL B cells mediated by the CXCR4/SDF-1 axis," Blood 128(12):1609-1613 (2016).
Payne, G. "Progress in immunoconjugate cancer therapeutics," Cancer Cell 3(3):207-212 (2003).
Peggs et al., "Cancer immunotherapy: co-stimulatory agonists and co-inhibitory antagonists," Clinical and Experimental Immunology 157(1):9-19 (2009).
Ponader et al., "The Bruton tyrosine kinase inhibitor PCI-32765 thwarts chronic lymphocytic leukemia cell survival and tissue homing in vitro and in vivo," Blood 119(5):1182-1189 (2012).
Rajaiya et al., "Induction of Immunoglobulin Heavy-Chain Transcription through the Transcription Factor Bright Requires TFII-I," Molecular and Cellular Biology 26(12):4758-4768 (2006).
Rodriguez et al., "Tyrosine residues in phospholipase Cgamma 2 essential for the enzyme function in B-cell signaling," Journal of Biological Chemistry 276(51):47982-47992 (2001).
Shevach et al., "The GITR-GITRL interaction: co-stimulation or contrasuppression of regulatory activity?," Nature Reviews Immunology 6(8):613-618 (2006).
Strome et al., "B7-H1 blockade augments adoptive T-cell immunotherapy for squamous cell carcinoma," Cancer Research 63(19):6501-6505 (2003).
Sukumar et al., "Characterization of MK-4166, a Clinical Agonistic Antibody That Targets Human GITR and Inhibits the Generation and Suppressive Effects of T Regulatory Cells," Cancer Research 77(16):4378-4388 (2017).
Syrigos et al., "Antibody Directed Enzyme Prodrug Therapy (ADEPT): A Review of the Experimental and Clinical Considerations," Anticancer Research 19(1A):605-613 (1999).
Tanaka et al., "Regulatory T cells in cancer immunotherapy," Cell Research 27(1):109-118 (2017).
Thompson et al., "Tumor B7-H1 is associated with poor prognosis in renal cell carcinoma patients with long-term follow-up," Cell Research 66(7):3381-3385 (2006).
Thompson et al., "PD-1 is expressed by tumor-infiltrating immune cells and is associated with poor outcome for patients with renal cell carcinoma," Clinical Cancer Research 13(6):1757-1761 (2007).
Tigue et al., "MEDI1873, a potent, stabilized hexameric agonist of human GITR with regulatory T-cell targeting potential." Oncoimmunology 6(3):e1280645 (2017).
Trail et al., "Monoclonal antibody drug immunoconjugates for targeted treatment of cancer," Cancer Immunology, Immunotherapy 52(5):328-337 (2003).
Tsushima et al., "Predominant expression of B7-H1 and its immunoregulatory roles in oral squamous cell carcinoma," Oral Oncology 42(3):268-274 (2006).
Weinberg, "Anti-OX40 (CD134) administration to nonhuman primates: immunostimulatory effects and toxicokinetic study," Journal of Immunotherapy 29(6):575-85 (2006).
Wintterle et al., "Expression of the B7-related molecule B7-H1 by glioma cells: a potential mechanism of immune paralysis," Cancer Research 63(21):7462-7467 (2003).
Wu et al., "Arming antibodies: prospects and challenges for immunoconjugates," Nature Biotechnology 23(9):1137-1146 (2005).
Xie et al., "In vivo behaviour of antibody-drug conjugates for the targeted treatment of cancer," Expert Opinion on Biological Therapy 6(3):281-291 (2006).
Yang et al., "BAP-135, a target for Bruton's tyrosine kinase in response to B cell receptor engagement," Proceedings of the National Academy of Sciences 94(2):604-609 (1997).
Zhang et al., "Structural and functional analysis of the costimulatory receptor programmed death-1," Immunity 20(3):337-347 (2004).

\* cited by examiner

SEQUENCES

SEQ ID NO. 1 (AB12 VH):
QVQLVQSGAEVKKPGSSVKVSCKASGGTFSRYIINWVRQAPGQGLEWMGRIIPILGVEN
YAQKFQGRVTITADKSTSTAYMELSSLRSEDTAVYYCARKDWFDYWGQGTLVTVSSAS
TKGPSVFPLA

SEQ ID NO. 2 (AB12 VL):
EIVLTQSPGTLSLSPGERATLSCRASQSVSSYLAWYQQKPGQAPRLLIYGASSRATGIPD
RFSGSGSGTDFTLTISRLEPEDFAVYYCQQYGSSPLTFGGGTKVEIKRTVAAPSVFIFP

SEQ ID NO. 3 (VH CDR1):
RYIIN

SEQ ID NO. 4 (VH CDR2):
RIIPILGVENYAQKFQG

SEQ ID NO. 5 (VH CDR3):
KDWFDY

SEQ ID NO. 6 (VL CDR1):
RASQSVSSYLA

SEQ ID NO. 7 (VL CDR2):
GASSRAT

SEQ ID NO. 8 (VL CDR3):
QQYGSSPLT

Figure 1

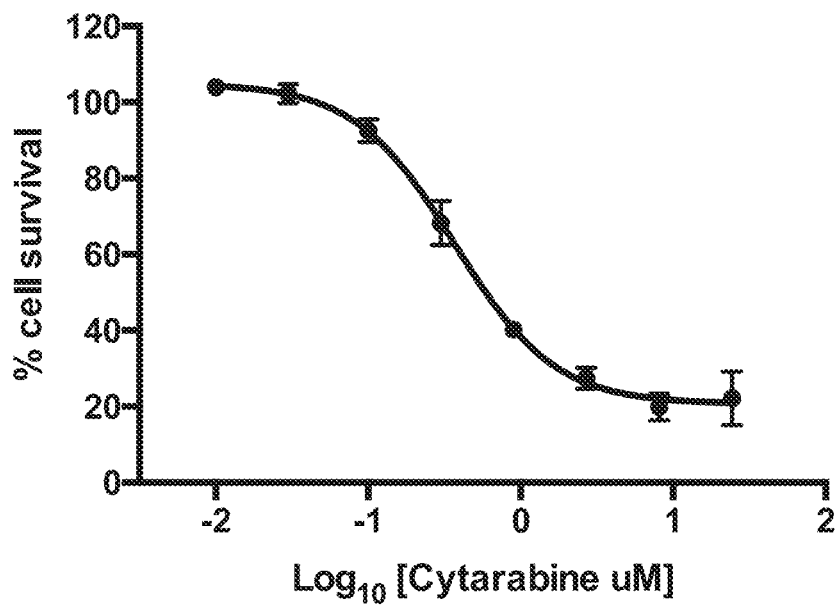
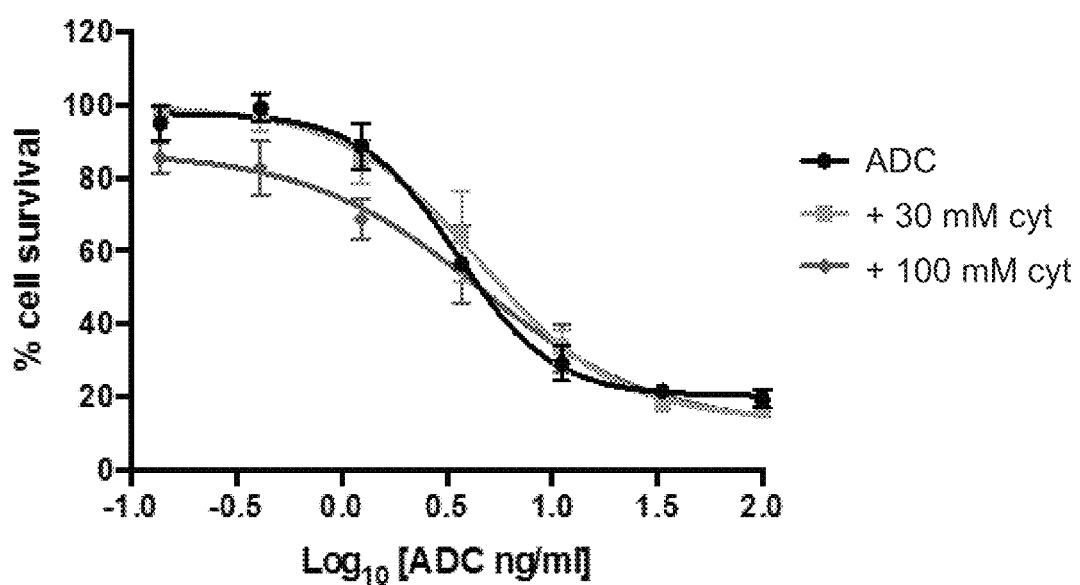
Figure 4

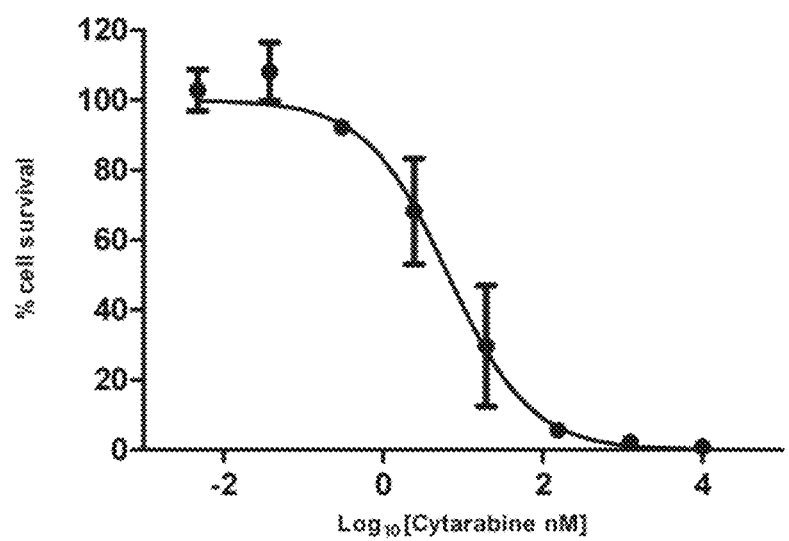
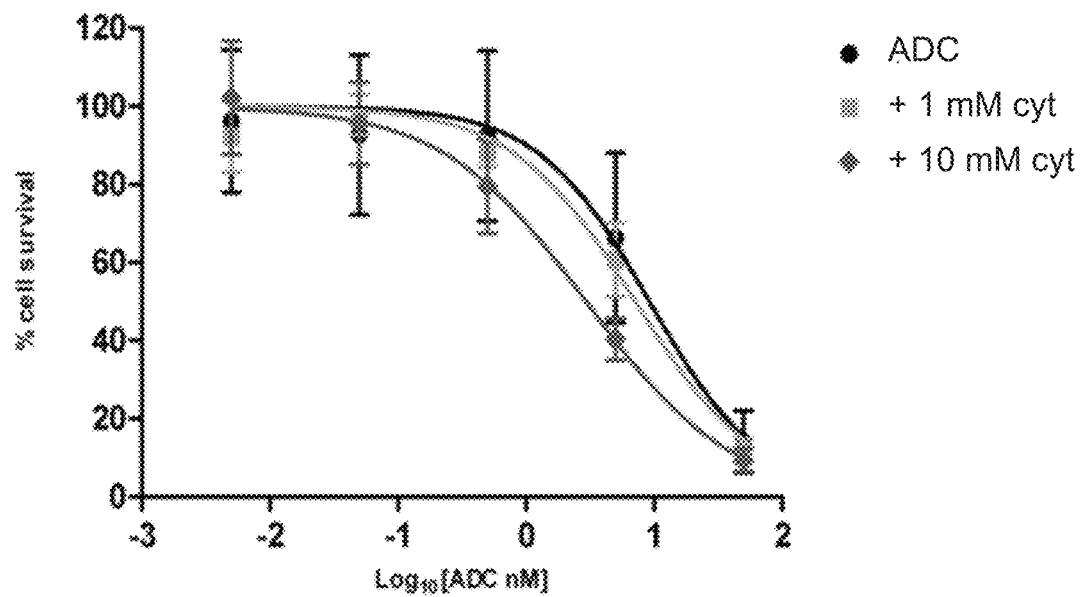
Figure 5

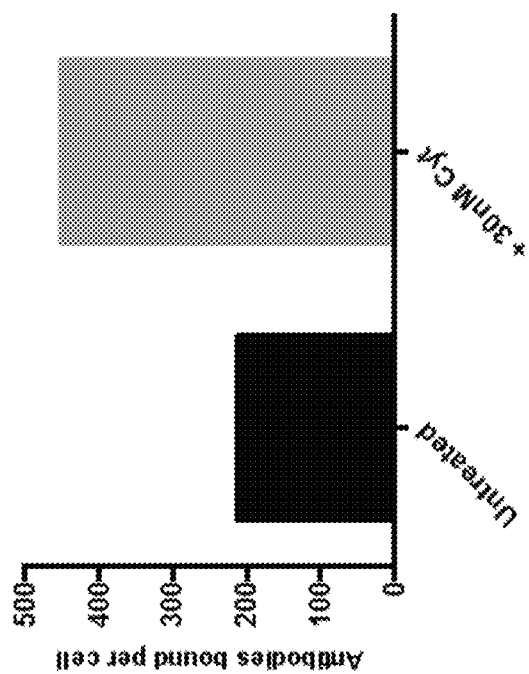
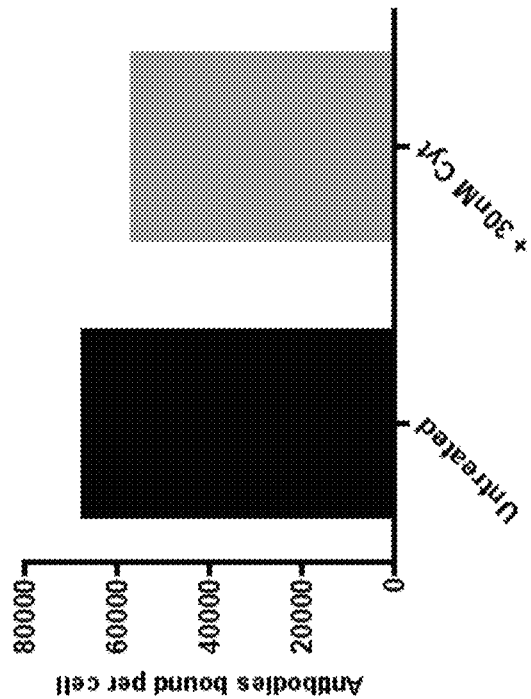
Figure 6

COMBINATION THERAPY WITH AN ANTI-CD25 ANTIBODY-DRUG CONJUGATE

CROSS-REFERENCE TO RELATED APPLICATIONS

This application is a national phase application under 35 U.S.C. § 371 of PCT International Application No. PCT/EP2018/060214, filed Apr. 20, 2018, which claims the benefit of GB1706252.2, GB1706251.4, GB1706250.6, GB1706249.8, GB1706248.0, GB1706247.2, GB1706246.4, GB1706245.6, all filed Apr. 20, 2017, and GB1805189.6 filed Mar. 29, 2017.

FIELD

The present disclosure relates to combination therapies for the treatment of pathological conditions, such as cancer. In particular, the present disclosure relates to combination therapies comprising treatment with an Antibody Drug Conjugate (ADC) and a secondary agent.

BACKGROUND

Antibody Therapy

Antibody therapy has been established for the targeted treatment of subjects with cancer, immunological and angiogenic disorders (Carter, P. (2006) Nature Reviews Immunology 6:343-357). The use of antibody-drug conjugates (ADC), i.e. immunoconjugates, for the local delivery of cytotoxic or cytostatic agents, i.e. drugs to kill or inhibit tumour cells in the treatment of cancer, targets delivery of the drug moiety to tumours, and intracellular accumulation therein, whereas systemic administration of these unconjugated drug agents may result in unacceptable levels of toxicity to normal cells (Xie et al (2006) Expert. Opin. Biol. Ther. 6(3):281-291; Kovtun et al (2006) Cancer Res. 66(6): 3214-3121; Law et al (2006) Cancer Res. 66(4):2328-2337; Wu et al (2005) Nature Biotech. 23(9):1137-1145; Lambert J. (2005) Current Opin. in Pharmacol. 5:543-549; Hamann P. (2005) Expert Opin. Ther. Patents 15(9):1087-1103; Payne, G. (2003) Cancer Cell 3:207-212; Trail et al (2003) Cancer Immunol. Immunother. 52:328-337; Syrigos and Epenetos (1999) Anticancer Research 19:605-614).

CD25

The type I transmembrane protein CD25 is present on activated T- and B-cells, some thymocytes, myeloid precursors, and oligodendrocytes. On activated T-cells, it forms heterodimers with the beta- and gamma subunits (CD122 and CD132), thus comprising the high-affinity receptor for IL-2. This ligand represents a survival factor for activated T-cells, as removal of IL-2 leads to immediate death of these cells.

In case of B-cells, CD25 is physiologically expressed in early developmental stages of late pro-B and pre-B cells. Malignancies arising from this stage of B-cell differentiation may thus also express CD25. Mast cell lesions are also positive for CD25 which is thus considered as a key diagnostic criterion for determination of systemic mastocytosis. In Hodgkin lymphomas, CD25 is reported to be not expressed in Hodgkin-/Reed-Sternberg cells in nodular lymphocyte predominance Hodgkin lymphoma (NLPHL), whereas the same cell type expresses CD25 at varying levels in classical Hodgkin' lymphomas of mixed cellularity type. The general expression levels are reported to be lower than in tumor infiltrating lymphocytes (TILs), which may result in problems demonstrating CD25 tumor cells in these cases (Levi et al., Merz et al, 1995).

Expression of the target antigen has also been reported for several B- and T-cell-derived subtypes of non-Hodgkin-lymphomas, i.e. B-cell chronic lymphatic leukemia, hairy cell leukemia, small cell lymphocytic lymphoma/chronic lymphocytic leukemia as well as adult T-cell leukemia/lymphoma and anaplastic large cell lymphoma.

CD25 may be localised to the membrane, with some expression observed in the cytoplasm. Soluble CD25 may also be observed outside of cells, such as in serum.

Therapeutic Uses of Anti-CD25 ADCs

The efficacy of an Antibody Drug Conjugate comprising an anti-CD25 antibody (an anti-CD25-ADC) in the treatment of, for example, cancer has been established—see, for example, WO2014/057119, WO2016/083468, and WO2016/166341.

Research continues to further improve the efficacy, tolerability, and clinical utility of anti-CD25 ADCs. To this end, the present authors have identified clinically advantageous combination therapies in which an anti-CD25 ADC is administered in combination with at least one secondary agent.

SUMMARY

The present authors have determined that the administration of a combination of an ADC and secondary agent to an individual leads to unexpected clinical advantages.

Accordingly, in one aspect the disclosure provides a method for treating a disorder in an individual, the method comprising administering to the individual an effective amount of an ADC and secondary agent.

The disorder may be a proliferative disease, for example a cancer such as Hodgkin's and non-Hodgkin's Lymphoma, including diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL) and leukemias such as Hairy cell leukemia (HCL), Hairy cell leukemia variant (HCL-v), Acute Myeloid Leukaemia (AML), and Acute Lymphoblastic Leukaemia (ALL) such as Philadelphia chromosome-positive ALL (Ph+ ALL) or Philadelphia chromosome-negative ALL (Ph− ALL).

The proliferative disease may be characterised by the presence of a neoplasm comprising both CD25+ve and CD25−ve cells.

The proliferative disease may be characterised by the presence of a neoplasm composed of CD25−ve neoplastic cells, optionally wherein the CD25−ve neoplastic cells are associated with CD25+ve non-neoplastic cells such as CD25+ve T-cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of CD25+ve neoplastic cells. Solid tumors may be neoplasms, including non-haematological cancers, infiltrated with CD25+ve cells, such as CD25+ve T-cells; such solid tumours may lack expression of CD25 (that is, comprise or be composed of CD25−ve neoplastic cells).

For example, the solid tumour may be a tumour with high levels of infiltrating T-cells, such as infiltrating regulatory T-cells (Treg; Ménétrier-Caux, C., et al., Targ Oncol (2012) 7:15-28; Arce Vargas et al., 2017, Immunity 46, 1-10; Tanaka, A., et al., Cell Res. 2017 January; 27(1):109-118). Accordingly, the solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

The ADC may be anti-CD25-ADC, such as ADCX25 described herein.

The secondary agent may be a Bruton's Tyrosine Kinase inhibitor (BTKi), a PD1 antagonist, a PD-L1 antagonist, a GITR agonist, an OX40 agonist, a CTLA-4 antagonist, Fludarabine or Cytarabine, or a hypomethylating agent.

The individual may be human. The individual may have cancer, or may have been determined to have cancer. The individual may have, or have been determined to have, a CD25+ cancer or CD25+ tumour-associated non-tumour cells, such as CD25+ infiltrating T-cells.

The individual may have, or have been determined to have, a PD-L1+ cancer.

In the disclosed methods the ADC may be administered before the secondary agent, simultaneous with the secondary agent, or after the secondary agent. The disclosed methods may comprise administering a further chemotherapeutic agent to the individual.

In another aspect, the disclosure provides a first composition comprising an ADC for use in a method of treating a disorder in an individual, wherein the treatment comprises administration of the first composition in combination with a second composition comprising a secondary agent.

Also provided by this aspect is a first composition comprising a secondary agent for use in a method of treating a disorder in an individual, wherein the treatment comprises administration of the first composition in combination with a second composition comprising an ADC.

The disorder may be a proliferative disease, for example a cancer such as Hodgkin's and non-Hodgkin's Lymphoma, including diffuse large B-cell lymphoma (DLBCL), follicular lymphoma, (FL), Mantle Cell lymphoma (MCL), chronic lymphatic lymphoma (CLL) Marginal Zone B-cell lymphoma (MZBL), and leukemias such as Hairy cell leukemia (HCL), Hairy cell leukemia variant (HCL-v), Acute Myeloid Leukaemia (AML), and Acute Lymphoblastic Leukaemia (ALL) such as Philadelphia chromosome-positive ALL (Ph+ ALL) or Philadelphia chromosome-negative ALL (Ph− ALL).

The proliferative disease may be characterised by the presence of a neoplasm comprising both CD25+ve and CD25−ve cells.

The proliferative disease may be characterised by the presence of a neoplasm composed of CD25−ve neoplastic cells, optionally wherein the CD25−ve neoplastic cells are associated with CD25+ve non-neoplastic cells such as CD25+ve T-cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of CD25+ve neoplastic cells. Solid tumors may be neoplasms, including non-haematological cancers, infiltrated with CD25+ve cells, such as CD25+ve T-cells; such solid tumours may lack expression of CD25 (that is, comprise or be composed of CD25-ve neoplastic cells).

For example, the solid tumour may be a tumour with high levels of infiltrating T-cells, such as infiltrating regulatory T-cells (Treg; Ménétrier-Caux, C., et al., Targ Oncol (2012) 7:15-28; Arce Vargas et al., 2017, Immunity 46, 1-10; Tanaka, A., et al., Cell Res. 2017 January; 27(1):109-118). Accordingly, the solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

The ADC may be anti-CD25-ADC, such as ADCX25 described herein.

The secondary agent may be a Bruton's Tyrosine Kinase inhibitor (BTKi), a PD1 antagonist, a PD-L1 antagonist, a GITR agonist, an OX40 agonist, a CTLA-4 antagonist, Fludarabine or Cytarabine, or a hypomethylating agent.

The individual may be human. The individual may have cancer, or may have been determined to have cancer. The individual may have, or have been determined to have, a CD25+ cancer or CD25+ tumour-associated non-tumour cells, such as CD25+infiltrating T-cells.

The individual may have, or have been determined to have, a PD-L1+ cancer.

The first composition may be administered before the second composition, simultaneous with the second composition, or after the second composition. The treatment may comprise administering a further chemotherapeutic agent to the individual.

In a further aspect, the disclosure provides the use of n ADC in the manufacture of a medicament for treating a disorder in an individual, wherein the medicament comprises an ADC, and wherein the treatment comprises administration of the medicament in combination with a composition comprising secondary agent.

Also provided by this aspect is the use of secondary agent in the manufacture of a medicament for treating a disorder in an individual, wherein the medicament comprises a secondary agent, and wherein the treatment comprises administration of the medicament in combination with a composition comprising an ADC.

The disorder may be a proliferative disease, for example a cancer such as Hodgkin's and non-Hodgkin's Lymphoma, including diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL) and leukemias such as Hairy cell leukemia (HCL), Hairy cell leukemia variant (HCL-v), Acute Myeloid Leukaemia (AML), and Acute Lymphoblastic Leukaemia (ALL) such as Philadelphia chromosome-positive ALL (Ph+ ALL) or Philadelphia chromosome-negative ALL (Ph− ALL).

The proliferative disease may be characterised by the presence of a neoplasm comprising both CD25+ve and CD25−ve cells.

The proliferative disease may be characterised by the presence of a neoplasm composed of CD25−ve neoplastic cells, optionally wherein the CD25−ve neoplastic cells are associated with CD25+ve non-neoplastic cells such as CD25+ve T-cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of CD25+ve neoplastic cells. Solid tumors may be neoplasms, including non-haematological cancers, infiltrated with CD25+ve cells, such as CD25+ve T-cells; such solid tumours may lack expression of CD25 (that is, comprise or be composed of CD25-ve neoplastic cells).

For example, the solid tumour may be a tumour with high levels of infiltrating T-cells, such as infiltrating regulatory T-cells (Treg; Ménétrier-Caux, C., et al., Targ Oncol (2012) 7:15-28; Arce Vargas et al., 2017, Immunity 46, 1-10; Tanaka, A., et al., Cell Res. 2017 January; 27(1):109-118). Accordingly, the solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

The ADC may be anti-CD25-ADC, such as ADCX25 described herein.

The secondary agent may be a Bruton's Tyrosine Kinase inhibitor (BTKi), a PD1 antagonist, a PD-L1 antagonist, a GITR agonist, an OX40 agonist, a CTLA-4 antagonist, Fludarabine or Cytarabine, or a hypomethylating agent.

The individual may be human. The individual may have cancer, or may have been determined to have cancer. The individual may have, or have been determined to have, a CD25+ cancer or CD25+ tumour-associated non-tumour cells, such as CD25+ infiltrating T-cells.

The individual may have, or have been determined to have, a PD-L1+ cancer.

The medicament may be administered before the composition, simultaneous with the composition, or after the composition. The treatment may comprise administering a further chemotherapeutic agent to the individual.

Another aspect of the disclosure provides a kit comprising:
- a first medicament comprising an ADC;
- a second medicament comprising a secondary agent; and, optionally,
- a package insert comprising instructions for administration of the first medicament to an individual in combination with the second medicament for the treatment of a disorder.

Also provided by this aspect is a kit comprising a medicament comprising an ADC and a package insert comprising instructions for administration of the medicament to an individual in combination with a composition comprising a secondary agent for the treatment of a disorder.

Further provided by this aspect is a kit comprising a medicament comprising a secondary agent and a package insert comprising instructions for administration of the medicament to an individual in combination with a composition comprising an ADC for the treatment of a disorder.

The disorder may be a proliferative disease, for example a cancer such as Hodgkin's and non-Hodgkin's Lymphoma, including diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL) and leukemias such as Hairy cell leukemia (HCL), Hairy cell leukemia variant (HCL-v), Acute Myeloid Leukaemia (AML), and Acute Lymphoblastic Leukaemia (ALL) such as Philadelphia chromosome-positive ALL (Ph+ ALL) or Philadelphia chromosome-negative ALL (Ph– ALL).

The proliferative disease may be characterised by the presence of a neoplasm comprising both CD25+ve and CD25–ve cells.

The proliferative disease may be characterised by the presence of a neoplasm composed of CD25–ve neoplastic cells, optionally wherein the CD25–ve neoplastic cells are associated with CD25+ve non-neoplastic cells such as CD25+ve T-cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of CD25+ve neoplastic cells. Solid tumors may be neoplasms, including non-haematological cancers, infiltrated with CD25+ve cells, such as CD25+ve T-cells; such solid tumours may lack expression of CD25 (that is, comprise or be composed of CD25-ve neoplastic cells).

For example, the solid tumour may be a tumour with high levels of infiltrating T-cells, such as infiltrating regulatory T-cells (Treg; Ménétrier-Caux, C., et al., Targ Oncol (2012) 7:15-28; Arce Vargas et al., 2017, Immunity 46, 1-10; Tanaka, A., et al., Cell Res. 2017 January; 27(1):109-118). Accordingly, the solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

The ADC may be anti-CD25-ADC, such as ADCX25 described herein.

The secondary agent may be a Bruton's Tyrosine Kinase inhibitor (BTKi), a PD1 antagonist, a PD-L1 antagonist, a GITR agonist, an OX40 agonist, a CTLA-4 antagonist, Fludarabine or Cytarabine, or a hypomethylating agent.

The individual may be human. The individual may have cancer, or may have been determined to have cancer. The individual may have, or have been determined to have, a CD25+ cancer or CD25+ tumour-associated non-tumour cells, such as CD25+infiltrating T-cells.

The individual may have, or have been determined to have, a PD-L1+ cancer.

The medicament or composition comprising the ADC may be administered before the medicament or composition comprising the secondary agent, simultaneous with the medicament or composition comprising the secondary agent, or after the medicament or composition comprising the secondary agent. The treatment may comprise administering a further chemotherapeutic agent to the individual.

In a yet further aspect, the disclosure provides a composition comprising an ADC and a secondary agent.

Also provided in this aspect of the disclosure is a method of treating a disorder in an individual, the method comprising administering to the individual an effective amount of the composition comprising an ADC and a secondary agent.

Also provided in this aspect of the disclosure is a composition comprising an ADC and a secondary agent for use in a method of treating a disorder in an individual.

Also provided in this aspect of the disclosure is the use of a composition comprising an ADC and a secondary agent in the manufacture of a medicament for treating a disorder in an individual.

Also provided in this aspect of the disclosure is a kit comprising composition comprising an ADC and a secondary agent and a set of instructions for administration of the medicament to an individual for the treatment of a disorder.

The disorder may be a proliferative disease, for example a cancer such as Hodgkin's and non-Hodgkin's Lymphoma, including diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL), and leukemias such as Hairy cell leukemia (HCL), Hairy cell leukemia variant (HCL-v), Acute Myeloid Leukaemia (AML), and Acute Lymphoblastic Leukaemia (ALL) such as Philadelphia chromosome-positive ALL (Ph+ ALL) or Philadelphia chromosome-negative ALL (Ph− ALL).

The proliferative disease may be characterised by the presence of a neoplasm comprising both CD25+ve and CD25−ve cells.

The proliferative disease may be characterised by the presence of a neoplasm composed of CD25−ve neoplastic cells, optionally wherein the CD25−ve neoplastic cells are associated with CD25+ve non-neoplastic cells such as CD25+ve T-cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of CD25+ve neoplastic cells. Solid tumors may be neoplasms, including non-haematological cancers, infiltrated with CD25+ve cells, such as CD25+ve T-cells; such solid tumours may lack expression of CD25 (that is, comprise or be composed of CD25-ve neoplastic cells).

For example, the solid tumour may be a tumour with high levels of infiltrating T-cells, such as infiltrating regulatory T-cells (Treg; Ménétrier-Caux, C., et al., Targ Oncol (2012) 7:15-28; Arce Vargas et al., 2017, Immunity 46, 1-10; Tanaka, A., et al., Cell Res. 2017 January; 27(1):109-118). Accordingly, the solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

The ADC may be anti-CD25-ADC, such as ADCX25 described herein.

The secondary agent may be a Bruton's Tyrosine Kinase inhibitor (BTKi), a PD1 antagonist, a PD-L1 antagonist, a GITR agonist, an OX40 agonist, a CTLA-4 antagonist, Fludarabine or Cytarabine, or a hypomethylating agent.

The individual may be human. The individual may have cancer, or may have been determined to have cancer. The individual may have, or have been determined to have, a CD25+ cancer or CD25+ tumour-associated non-tumour cells, such as CD25+infiltrating T-cells.

The individual may have, or have been determined to have, a PD-L1+ cancer.

The treatment may comprise administering a further chemotherapeutic agent to the individual.

DETAILED DESCRIPTION

Antibody Drug Conjugates (ADCs)

The present disclosure relates to the improved efficacy of combinations of an ADC and a secondary agent.

The ADC can deliver a drug to a target location. The target location is preferably a proliferative cell population. The antibody is an antibody for an antigen present on a proliferative cell population. In one aspect the antigen is absent or present at a reduced level in a non-proliferative cell population compared to the amount of antigen present in the proliferative cell population, for example a tumour cell population.

The ADC may comprise a linker which may be cleaved so as to release the drug at the target location. The drug may be a compound selected from RelA, RelB, RelC, RelD or RelE. Thus, the conjugate may be used to selectively provide a compound RelA, RelB, RelC, RelD or RelE to the target location.

The linker may be cleaved by an enzyme present at the target location.

The disclosure particularly relates treatment with an anti-CD25 ADC disclosed in WO2014/057119, and as herein described.

Anti-CD25 ADCs

As used herein, the term "CD25-ADC" refers to an ADC in which the antibody component is an anti-CD25 antibody. The term "PBD-ADC" refers to an ADC in which the drug component is a pyrrolobenzodiazepine (PBD) warhead. The term "anti-CD25-ADC" refers to an ADC in which the antibody component is an anti-CD25 antibody, and the drug component is a PBD warhead.

The ADC may comprise a conjugate of formula $L-(D^L)_p$, where $D^L$ is of formula I or II:

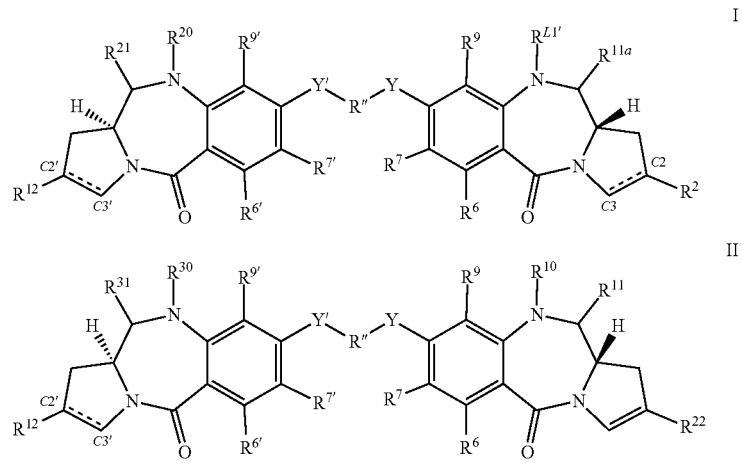

wherein:

L is an antibody (Ab) which is an antibody that binds to CD25;

when there is a double bond present between C2' and C3', $R^{12}$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-6}$ saturated cycloalkyl;

(id)

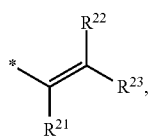

wherein each of $R^{21}$, $R^{22}$ and $R^{23}$ are independently selected from H, $C_{1-3}$ saturated alkyl, $C_{2-3}$ alkenyl, $C_{2-3}$ alkynyl and cyclopropyl, where the total number of carbon atoms in the $R^{12}$ group is no more than 5;

(ie)

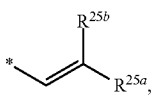

wherein one of $R^{25a}$ and $R^{25b}$ is H and the other is selected from:

phenyl, which phenyl is optionally substituted by a group selected from halo, methyl, methoxy; pyridyl; and thiophenyl; and (if)

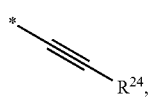

where $R^{24}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2' and C3', $R^{12}$ is

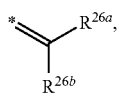

where $R^{26a}$ and $R^{26b}$ are independently selected from H, F, $C_{1-4}$ saturated alkyl, $C_{2-3}$ alkenyl, which alkyl and alkenyl groups are optionally substituted by a group selected from $C_1$0.4 alkyl amido and C1-4 alkyl ester; or, when one of $R^{26a}$ and $R^{26b}$ is H, the other is selected from nitrile and a $C_{1-4}$ alkyl ester;

$R^6$ and $R^9$ are independently selected from H, R, OH, OR, SH, SR, $NH_2$, NHR, NRR', nitro, $Me_3Sn$ and halo;

where R and R' are independently selected from optionally substituted C1-12 alkyl, C3-20 heterocyclyl and $C_{5-20}$ aryl groups;

$R^7$ is selected from H, R, OH, OR, SH, SR, $NH_2$, NHR, NHRR', nitro, $Me_3Sn$ and halo;

R" is a $C_{3-12}$ alkylene group, which chain may be interrupted by one or more heteroatoms, e.g. O, S, $NR^{N2}$ (where $R^{N2}$ is H or $C_{1-4}$ alkyl), and/or aromatic rings, e.g. benzene or pyridine;

Y and Y' are selected from O, S, or NH;

$R^{6'}$, $R^{7'}$, $R^{9'}$ are selected from the same groups as $R^6$, $R^7$ and $R^9$ respectively;

[Formula I]

$R^{L1'}$ is a linker for connection to the antibody (Ab);

$R^{11a}$ is selected from OH, $OR^A$, where $R^A$ is $C_{1-4}$ alkyl, and $SO_zM$, where z is 2 or 3 and M is a monovalent pharmaceutically acceptable cation;

$R^{20}$ and $R^{21}$ either together form a double bond between the nitrogen and carbon atoms to which they are bound or;

$R^{20}$ is selected from H and $R^C$, where $R^C$ is a capping group;

$R^{21}$ is selected from OH, $OR^A$ and $SO_zM$;

when there is a double bond present between C2 and C3, $R^2$ is selected from the group consisting of:

(ia) $C_{5-10}$ aryl group, optionally substituted by one or more substituents selected from the group comprising: halo, nitro, cyano, ether, carboxy, ester, $C_{1-7}$ alkyl, $C_{3-7}$ heterocyclyl and bis-oxy-$C_{1-3}$ alkylene;

(ib) $C_{1-5}$ saturated aliphatic alkyl;

(ic) $C_{3-8}$ saturated cycloalkyl;

(id)

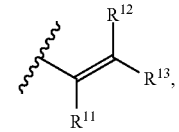

wherein each of $R^{11}$, $R^{12}$ and $R^{13}$ are independently selected from H, $C_{1-3}$ saturated alkyl, $C_{2-3}$ alkenyl, $C_{2-3}$ alkynyl and cyclopropyl, where the total number of carbon atoms in the $R^2$ group is no more than 5;

(ie)

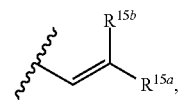

wherein one of $R^{15a}$ and $R^{16b}$ is H and the other is selected from: phenyl, which phenyl is optionally substituted by a group selected from halo, methyl, methoxy; pyridyl; and thiophenyl; and (if)

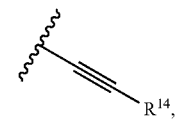

where $R^{14}$ is selected from: H; $C_{1-3}$ saturated alkyl; $C_{2-3}$ alkenyl; $C_{2-3}$ alkynyl; cyclopropyl; phenyl, which phenyl is optionally substituted by a group selected from halo, methyl, methoxy; pyridyl; and thiophenyl;

when there is a single bond present between C2 and C3, R² is

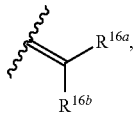

where $R^{16a}$ and $R^{16b}$ are independently selected from H, F, $C_{1-4}$ saturated alkyl, $C_{2-3}$ alkenyl, which alkyl and alkenyl groups are optionally substituted by a group selected from $C_{1-4}$ alkyl amido and $C_{1-4}$ alkyl ester; or, when one of $R^{16a}$ and $R^{16b}$ is H, the other is selected from nitrile and a $C_{1-4}$ alkyl ester;

[Formula II]

$R^{22}$ is of formula IIIa, formula IIIb or formula IIIc:

(a)

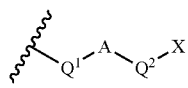

IIIa where A is a $C_{5-7}$ aryl group, and either (i) $Q^1$ is a single bond, and $Q^2$ is selected from a single bond and —Z—$(CH_2)_n$—, where Z is selected from a single bond, O, S and NH and n is from 1 to 3; or (ii) $Q^1$ is —CH=CH—, and $Q^2$ is a single bond;

(b)

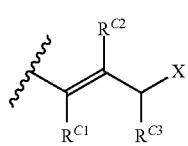

IIIb where;

$R^{C1}$, $R^{C2}$ and $R^{C3}$ are independently selected from H and unsubstituted $C_{1-2}$ alkyl;

(c)

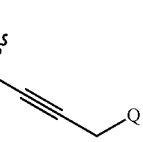

IIIc where Q is selected from O—$R^{L2'}$, S—$R^{L2'}$ and $NR^N$—$R^{L2'}$, and $R^N$ is selected from H, methyl and ethyl X is selected from the group comprising: O—$R^{L2'}$, S—$R^{L2'}$, $CO_2$—$R^{L2'}$, NH—C(=O)—$R^{L2'}$, NHNH—$R^{L2'}$, CONHNH—$R_{L2'}$,

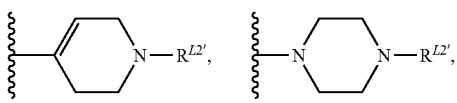

$NR^N R^{L2'}$, wherein $R^N$ is selected from the group comprising H and $C_{1-4}$ alkyl;

$R^{L2'}$ is a linker for connection to the antibody (Ab);

$R^{10}$ and $R^{11}$ either together form a double bond between the nitrogen and carbon atoms to which they are bound or;

$R^{10}$ is H and $R^{11}$ is selected from OH, $OR^A$ and $SO_z N$;

$R^{30}$ and $R^{31}$ either together form a double bond between the nitrogen and carbon atoms to which they are bound or;

$R^{30}$ is H and $R^{31}$ is selected from OH, $OR^A$ and $SO_z M$.

In some embodiments L-$R^{L1'}$ or L-$R^{L2'}$ is a group:

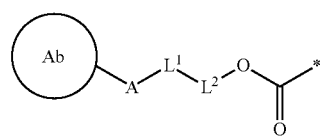

where the asterisk indicates the point of attachment to the PBD, Ab is the antibody, $L^1$ is a cleavable linker, A is a connecting group connecting $L^1$ to the antibody, $L^2$ is a covalent bond or together with —OC(=O)— forms a self-immolative linker.

In some of these embodiments, $L^1$ is enzyme cleavable.

It has previously been shown that such ADCs are useful in the treatment of CD25 expressing cancers (see, for example, WO2014/057119, which is incorporated by reference herein in its entirety).

The term anti-CD25-ADC may include any embodiment described in WO 2014/057119. In particular, in preferred embodiments the ADC may have the chemical structure:

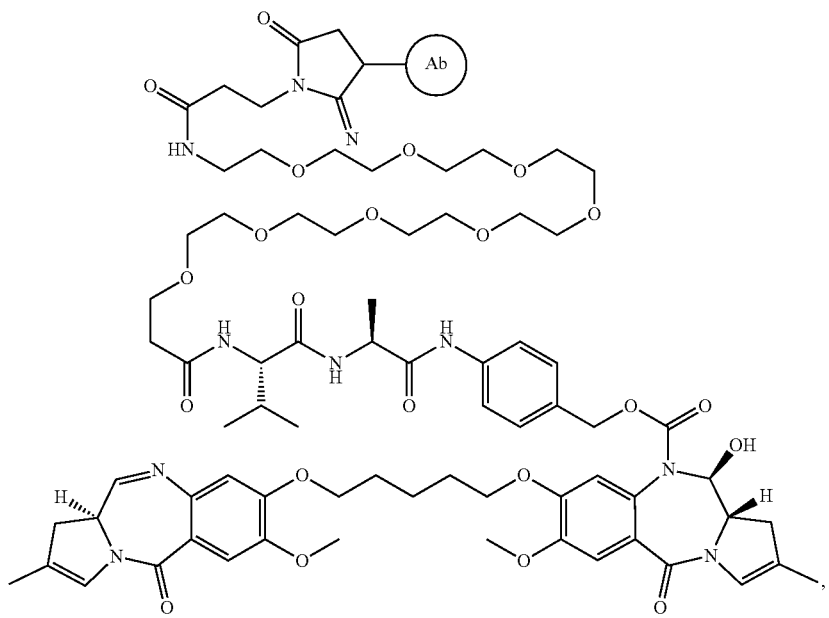

where the Ab is a CD25 antibody, and the DAR is between 1 and 8.

The antibody may comprise a VH domain comprising a VH CDR1 with the amino acid sequence of SEQ ID NO.3, a VH CDR2 with the amino acid sequence of SEQ ID NO.4, and a VH CDR3 with the amino acid sequence of SEQ ID NO.5.

In some aspects the antibody component of the anti-CD25-ADC is an antibody comprising: a VH domain comprising a VH CDR1 with the amino acid sequence of SEQ ID NO.3, a VH CDR2 with the amino acid sequence of SEQ ID NO.4, and a VH CDR3 with the amino acid sequence of SEQ ID NO.5. In some embodiments the antibody comprises a VH domain having the sequence according to SEQ ID NO. 1.

The antibody may further comprise: a VL domain comprising a VL CDR1 with the amino acid sequence of SEQ ID NO.6, a VL CDR2 with the amino acid sequence of SEQ ID NO.7, and a VL CDR3 with the amino acid sequence of SEQ ID NO.8. In some embodiments the antibody further comprises a VL domain having the sequence according to SEQ ID NO. 2.

In some embodiments the antibody comprises a VH domain and a VL domain, the VH and VL domains having the sequences of SEQ ID NO. 1 paired with SEQ ID NO. 2.

The VH and VL domain(s) may pair so as to form an antibody antigen binding site that binds CD25.

In preferred embodiments the antibody is an intact antibody comprising a VH domain and a VL domain, the VH and VL domains having sequences of SEQ ID NO. 1 and SEQ ID NO. 2.

In some embodiments the antibody is a fully human monoclonal IgG1 antibody, preferably IgG1,κ.

In some embodiments the antibody is the AB12 antibody described in WO 2004/045512 (Genmab A/S).

In an aspect the antibody is an antibody as described herein which has been modified (or further modified) as described below. In some embodiments the antibody is a humanised, deimmunised or resurfaced version of an antibody disclosed herein.

The preferred anti-CD25-ADC for use with the aspects of the present disclosure is ADCX25, as described herein below.

ADCx25

ADCx25 is an antibody drug conjugate composed of a human antibody against human CD25 attached to a pyrrolobenzodiazepine (PBD) warhead via a cleavable linker. The mechanism of action of ADCX25 depends on CD25 binding. The CD25 specific antibody targets the antibody drug conjugate (ADC) to cells expressing CD25. Upon binding, the ADC internalizes and is transported to the lysosome, where the protease sensitive linker is cleaved and free PBD dimer is released inside the target cell. The released PBD dimer inhibits transcription in a sequence-selective manner, due either to direct inhibition of RNA polymerase or inhibition of the interaction of associated transcription factors. The PBD dimer produces covalent crosslinks that do not distort the DNA double helix and which are not recognized by nucleotide excision repair factors, allowing for a longer effective period (Hartley 2011).

It has the chemical structure:

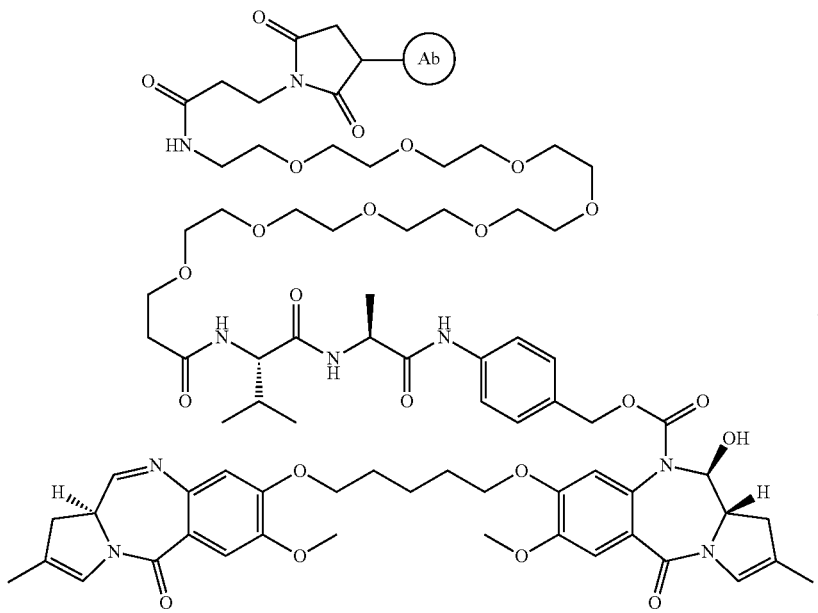

Ab represents Antibody AB12 (fully human monoclonal IgG1, K antibody with the VH and VL sequences SEQ ID NO. 1 and SEQ ID NO. 2, respectively, also known as HuMax-TAC). It is synthesised as described in WO 2014/057119 (Conj AB12-E) and typically has a DAR (Drug to Antibody Ratio) of 2.0+/−0.3.

CD25 Binding

The "first target protein" (FTP) as used herein is preferably CD25.

As used herein, "binds CD25" is used to mean the antibody binds CD25 with a higher affinity than a non-specific partner such as Bovine Serum Albumin (BSA, Genbank accession no. CAA76847, version no. CAA76847.1 GI:3336842, record update date: Jan. 7, 2011 02:30 PM). In some embodiments the antibody binds CD25 with an association constant ($K_a$) at least 2, 3, 4, 5, 10, 20, 50, 100, 200, 500, 1000, 2000, 5000, $10^4$, $10^5$ or $10^8$-fold higher than the antibody's association constant for BSA, when measured at physiological conditions. The antibodies of the disclosure can bind CD25 with a high affinity. For example, in some embodiments the antibody can bind CD25 with a $K_D$ equal to or less than about $10^{-6}$ M, such as equal to or less than one of $1 \times 10^{-6}$, $10^{-7}$, $10^{-8}$, $10^{-9}$, $10^{-10}$, $10^{-11}$, $10^{-12}$, $10^{-13}$ or $10^{-14}$.

In some embodiments, CD25 polypeptide corresponds to Genbank accession no. NP_000408, version no. NP_000408.1 GI:4557667, record update date: Sep. 9, 2012 04:59 PM. In one embodiment, the nucleic acid encoding CD25 polypeptide corresponds to Genbank accession no. NM_000417, version no. NM_000417.2 GI:269973860, record update date: Sep. 9, 2012 04:59 PM. In some embodiments, CD25 polypeptide corresponds to Uniprot/Swiss-Prot accession No. P01589.

Secondary Agents

The recent development of agents that enhance anti-tumor immunity is rapidly changing the treatment of a broad range of cancers. However, these treatments are not effective in all cancer types, responses are often not durable, and many patients receive little or no benefit from treatment. The prevailing assumption in the oncology field is that only combinations of immune-therapies with other treatment options will ultimately be able to cure cancer patients.

The ADC is well tolerated and active across a range of cancer types, and will likely be one component of combination therapies that increase the response rate and durability of treatment. The purpose of this disclosure is to combine the ADC with the secondary agent.

A secondary agent as described herein may be an Immune-oncology (IO) drug.

Immune-oncology (IO) drugs, a type of cancer therapy relying on the body's immune system to help fight cancer, have shown enhanced durability of anti-tumor response. There are different types of IO, including but not limited to PD1 inhibitors, PD-L1 inhibitors, CLTL4 inhibitors, GITR agonists and OX40 agonists. Due to the considerable fraction of patients who are not cured by single agent immunotherapies and ultimately relapse, combination treatments with alternative IO drugs or different therapeutic modalities are needed (see K S Peggs et al. 2009, Clinical and Experimental Immunology, 157: 9-19 [doi:10.1111/j.1365-2249.2009.03912.x]; D M Pardoll 2012 [doi:10.1038/nrc3239]).

Immunogenic cell death (ICD) is a particular form of cell death that stimulates an immune response against dead-cell antigens (released by dying cells) and it is considered as one of the best way to induce an adaptive immune response and improve the efficacy of anti-cancer treatment. This process is frequently suboptimal, calling for combinatorial strategies that attempt to restore the full immunogenicity of cell death for therapeutic purposes. There are several anti-neoplastic agents that can induce ICD such as various anthracyclines (including doxorubicin, epirubicin and idarubicin), alkylating agents (including oxaliplatin and cyclophosphamide), the topoisomerase II inhibitor mitoxantrone, and the proteasomal inhibitor Bortezomib.

Antibody-drug conjugates, including those with a PBD warhead, may be particularly suited as combination partners because they are more targeted compared to conventional chemotherapy and expected to offer an increased antigen presentation to infiltrating T cells as has been shown for auristatin-based ADCs.

Combining ADCs with IO therefore allows for dual benefits: on the one hand, the ADC will directly kill the tumor expressing the target, providing immediate anti-tumor activity, and on the other the immunogenic cell death induced by ADC mediated cell kill may boost a stronger and more durable adaptive immune response, as compared to when the IO is given as a single agent.

The secondary agent may be:
(a) a Bruton's Tyrosine Kinase inhibitor (BTKi), such as Ibrutinib (Imbruvica), Acalabrutinib/ACP-196, ONO/GS-4059, Spebrutinib/AVL-292/CC-292, HM71224 (Poseltinib) or BGB-3111 (Zanubrutinib);
(b) a PD1 antagonist, such as pembrolizumab, nivolumab, MEDI0680, PDR001 (spartalizumab), Camrelizumab, AUNP12, Pidilizumab, Cemiplimab (REGN-2810), AMP-224, BGB-A317 (Tisleizumab), or BGB-108;
(c) a PD-L1 antagonist, such as atezolizumab (Tecentriq), BMS-936559/MDX-1105, durvalumab/MEDI4736, or MSB0010718C (Avelumab);
(d) a GITR (Glucocorticoid-Induced TNFR-Related protein) agonist, such as MEDI1873, TRX518, GWN323, MK-1248, MK-4166, BMS-986156 or INCAGN1876;
(e) an OX40 agonist, such as MED10562, MEDI6383, MOXR0916, RG7888, OX40mAb24, INCAGN1949, GSK3174998, or PF-04518600;
(f) a CTLA-4 antagonist, such as ipilimumab (brand name Yervoy) or Tremelimumab (Originally developed by Pfizer, now Medimmune);
(g) Fludarabine or Cytarabine; or
(h) a hypomethylating agent, such as cytidine analogs—for example, 5-azacytidine (azacitidine) and 5-aza-2'-deoxycytidine (decitabine).

Each of these classes of secondary agent is described in more detail below.

BTK Inhibitors

BTK is a non-receptor tyrosine kinase indispensable for B lymphocyte development, differentiation and signalling. Binding of antigen to the B-cell antigen receptor (BCR) triggers signalling that ultimately leads to B-cell activation. After BCR engagement and activation at the plasma membrane, BTK phosphorylates PLCG2 at several sites, igniting the downstream signaling pathway through calcium mobilization, followed by activation of the protein kinase C (PKC) family members. PLCG2 phosphorylation is performed in close cooperation with the adapter protein B-cell linker protein BLNK [Yang et al., Proc. Natl. Acad. Sci. U.S.A. 94:604-609(1997); Rodriguez et al., J. Biol. Chem. 276:47982-47992(2001)].

BTK acts as a platform to bring together a diverse array of signalling proteins and is implicated in cytokine receptor signalling pathways. It plays an important role in the function of immune cells of innate as well as in adaptive immunity, as a component of the Toll-like receptors (TLR) pathway. The TLR pathway acts as a primary surveillance system for the detection of pathogens and are crucial to the activation of host defence [Horwood et al. J. Immunol. 176:3635-3641(2006)].

Another key role for BTK is the regulation of TLR9 activation in splenic B-cells. Within the TLR pathway, BTK induces tyrosine phosphorylation of TIRAP which leads to TIRAP degradation.

BTK also plays also a critical role in transcription regulation as it is involved in the signalling pathway linking TLR8 and TLR9. As a result, BTK activity induces the activity of NF-kappa-B, which is itself involved in regulating the expression of hundreds of genes. Other transcriptional targets of BTK include ARID3A, NFAT and GTF2I;

BTK is required for the formation of functional ARID3A DNA-binding complexes; whilst BTK's transient phosphorylatation of GTF2I causes it to translocate to the nucleus to bind regulatory enhancer elements to modulate gene expression [Rajaiya, Mol. Cell. Biol. 26:4758-4768(2006)].

BTK has a dual role in the regulation of apoptosis.

"BTK inhibitor" means any chemical compound or biological molecule that inhibits the activity of BTK. For example, agents that prevent kinase activity of BTK with an IC50 of 0.001 µM to about 2 µM.

The BTK enzyme inhibitory activity may be measured, based on the protocol provided by the manufacturer, using Btk (Invitrogen Corporation) and the Z'-LYTE™ Kinase Assay Kit-Tyr1 peptide (Invitrogen Corporation), which contains the following reagents: Tyr-1 peptide, Thy-1 phosphopeptide, 5× kinase buffer, ATP, development reagent B, development buffer, and stop reagent. 5 µl/well of a solution of a BTK inhibitor may be diluted with dimethyl sulfoxide (DMSO), or DMSO, and 10 µl/well of the substrate/enzyme mixture solution dispensed to a 96-well assay plate and a reaction carried out for 20 minutes at 30° C. The substrate/enzyme mixture solution may be prepared by dilution with the kinase buffer (DL-dithiothreitol (DTT, 2.7 mM), 1.33× kinase buffer) to provide a final concentration for the Tyr-1 peptide of 4 µM and a final BTK concentration of 5 nM. 5 µl/well of the adenosine triphosphate (ATP, final concentration=36 µM) can then be added and a reaction carried out for 1 hour at 30° C. After the completion of the reaction, 10 µL, of a development solution, provided by diluting the development reagent B to 128× using the development buffer, may be added and a reaction carried out for an additional 1 hour at 30° C. The enzymatic reaction can then be stopped by adding 10 µL, of the stop solution. The fluorescence intensity at 445 nm and 520 nm in each well may be measured using a Fusion Universal Microplate Analyzer (PerkinElmer Inc.) fluorescence plate reader. The percent phosphorylation may be determined using the ratio of the emission at 445 nm (coumarin emission) to the emission at 520 nm (fluorescein emission) in accordance with the protocol provided with the kit.

The percent inhibition (%) by a BTK inhibitor may be calculated using the following equation.

$$\text{percent inhibition (\%) of phosphorylation} = 1 - \{(AC-AX)/(AC-AB)\} \times 100$$

AX: % phosphorylation when a BTK inhibitor has been added

AB: % phosphorylation in the absence of ATP addition (blank)

AC: % phosphorylation when only DMSO has been added (control)

The 50% inhibition value (IC50 value) for a BTK inhibitor may be determined from the inhibition curve based on the % inhibition at each concentration of a BTK inhibitor.

The BTKi Ibrutinib (Imbruvica) is a small molecule drug that covalently binds to Bruton's tyrosine kinase (BTK) and has been used to treat B-cell cancers like mantle cell lymphoma, chronic lymphocytic leukemia, and Waldenström's macroglobulinemia, a form of non-Hodgkin's lymphoma.

Ibrutinib has been reported to reduce chronic lymphocytic leukemia (CLL) cell chemotaxis towards the chemokines CXCL12 and CXCL13, and inhibit cellular adhesion following stimulation at the B cell receptor (BCR) (S Ponader et al. 2011, doi:10.1182/blood-2011-10-386417. PMID 22180443.) Additionally, ibrutinib down-modulates the expression of CD20 by targeting the CXCR4/SDF1 axis (Pavlasova 2016, PMID 27480113. Together, these data are consistent with a mechanistic model whereby ibrutinib blocks BCR signalling, which drives B-cells into apoptosis and/or disrupts cell migration and adherence to protective tumour microenvironments.

In preclinical studies on chronic lymphocytic leukemia (CLL) cells, ibrutinib has been reported to promote apoptosis, inhibit proliferation, and also prevent CLL cells from responding to survival stimuli provided by the microenvironment (Pavlasova 2016). This also leads to a reduction of Mcl1 levels (anti-apoptotic protein) in malignant B cells. Treatment of activated CLL cells with ibrutinib resulted in inhibition of BTK tyrosine phosphorylation and also effectively abrogated downstream survival pathways activated by this kinase including ERK1/2, PI3K, and NE-κB. Additionally, ibrutinib inhibited proliferation of CLL cells in vitro, effectively blocking survival signals provided externally to CLL cells from the microenvironment including soluble factors (CD40L, BAFF, IL-6, IL-4, and TNF-α), fibronectin engagement and stromal cell contact.

Accordingly, combining an ADC, which targets a first target protein (FTP) with a BTKi is advantageous, because on the one hand, the ADC will directly kill the FTP positive tumor cells, while on the other hand the BTKi will interact with malignant B-cells resulting in inhibition of proliferation of the cancer cells. Next to FTP(+) tumor cells, FTP negative tumor cells in close proximity to FTP(+) tumor cells will potentially be killed by the bystander mechanism of the PBD-dimer released after cell kill of FTP(+) cells. Hence, the ADC will directly kill the tumor cells.

Furthermore, indications are that BTKi reduces tumour cell mobility and tips the regulatory balance in these cells more towards apoptosis. It is believed that these changes induced by the BTKi will make the tumour cells more susceptible to direct and indirect ADC medicated killing.

To show that ADCs works synergistically with BTKi, a panel of FTP (+) cell lines will be co-treated with a range of concentration of both ADC and BTK1. As negative controls, the same panel of cell lines will be treated with a range of concentrations of BTKi or with a range of concentration of ADC and vehicle. After incubation, two parameters will be measured: the amount of surface FTP (as determined by flow cytometry) and the in vitro cytotoxicity of the combinations (as determined by MTS assays). To determine the cytotoxicity, Cell viability is measured by adding MTS per well and incubating for 4 hours at 37° C. Percentage cell viability is calculated compared to the untreated control. Cytotoxic synergy is calculated by transforming the cell viability data into fraction affected, and calculating the combination index using the CalcuSyn analysis program.

BTKi suitable for use as secondary agents in the present disclosure include:

(1) 9-(1-acryloyl-3-azetidinyl)-6-amino-7-(4-phenoxyphenyl)-7, 9-dihydro-8H-purin-8-one, (2) 6-amino-9-{(3R)-1-[(2E)-4-(dimethylamino)-2-butenoyl]-3-pyrrolidinyl}-7-(4-phenoxyphenyl)-7,9-dihydro-8H-purin-8-one, (3) 9-[(1-acryloyl-4-piperidinyl)methyl]-6-amino-7-(4-phenoxyphenyl)-7,9-dihydro-8H-purin-8-one, (4) 6-amino-9-[(3R)-1-(2-butynoyl)-3-pyrrolidinyl]-7-(4-phenoxyphenyl)-7,9-dihydro-8H-purin-8-one, (5) 6-amino-9-{(3 S)-1-[(2E)-4-(dimethylamino)-2-butenoyl]-3-pyrrolidinyl}-7-(4-phenoxyphenyl)-7,9-dihydro-8H-purin-8-one, (6) 6-amino-7-[4-(3-chlorophenoxy)phenyl]-9-{(3R)-1-[(2E)-4-(dimethylamino)-2-butenoyl]-3-pyrrolidinyl}-7,9-dihydro-8H-purin-8-one, (7) 6-amino-9-[I-(2-butynoyl)-3-pyrrolidinyl]-7-(4-phenoxyphenyl)-7,9-dihydro-8H-purin-8-one, and (8) 6-amino-9-{1-[(2E)-4-(dimethylamino)-2-butenoyl]-3-pyrrolidinyl}-7-(4-phenoxyphenyl)-7,9-dihydro-8H-purin-8-one.

Preferred BTK inhibitors for use as secondary agents in the present disclosure include (Ibrutnib being most preferred):

a) Ibrutinib (Imbruvica)
  i. CAS Number→936563-96-1
    (see http://www.cas.org/content/chemical-substances/faqs)
  ii. NCBI Pubchem reference→24821094
    (see https://pubchem.ncbi.nlm.nih.gov/)
  iii. IUPHAR/BPS reference→6912
    (see http://www.guidetopharmacology.org/)
  iv. Unique Ingredient Identifier (UNII) →1X70OSD4VX
    (see http://www.fda.gov/ForIndustry/DataStandards/SubstanceRegistrationSystem-UniqueIngredientIdentifierUNII/default.htm)

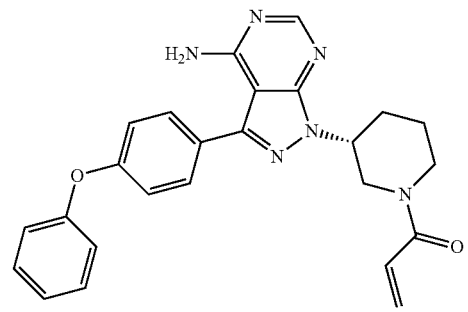 [SMILES: C=CC(=O)N1CCC[C@@H](n2nc(-c3ccc(Oc4ccccc4)cc3)c3c(N)ncnc32)C1]

Formula I, Ibrutinib: 1-[(3R)-3-[4-Amino-3-(4-phenoxyphenyl)-1H-pyrazolo[3,4-d]pyrimidin-1-yl]piperidin-1-yl]prop-2-en-1-one b) Acalabrutinib/ACP-196
  i. CAS Number→1420477-60-6
    (see http://www.cas.org/content/chemical-substances/faqs)
  ii. Chemspider→36764951
    (see https://http://www.chemspider.com/)

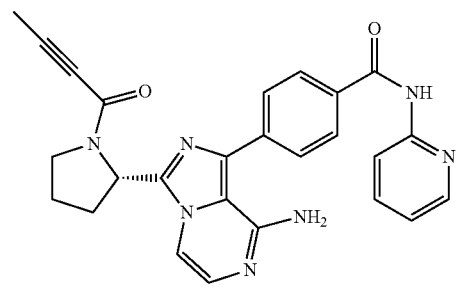 [SMILES: CC#CC(=O)N1CCC[C@H]1c1nc(-c2ccc(C(=O)Nc3ccccn3)cc2)c2c(N)nccn12]

Formula II, Acalabrutinib: 4-{8-Amino-3-[(2S)-1-(2-butynoyl)-2-pyrrolidinyl]imidazo[1,5-a]pyrazin-1-yl}-N-(2-pyridinyl)benzamide c) ONO/GS-4059
  i. CAS Number→1351635-67-0
    (see http://www.cas.org/content/chemical-substances/faqs)

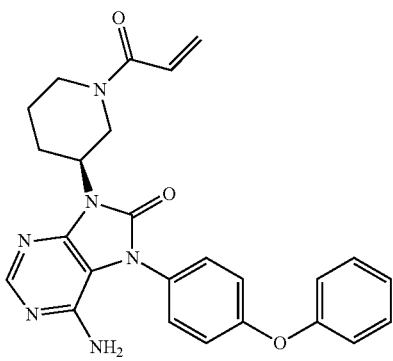 [SMILES: C=CC(=O)N1CCC[C@H](n2c(=O)n(-c3ccc(Oc4ccccc4)cc3)c3c(N)ncnc32)C1]

Formula III, ONO/GS-4059: 6-amino-7,9-dihydro-9-[(3S)-1-(1-oxo-2-propen-1-yl)-3-piperidinyl]-7-(4-phenoxyphenyl)-8H-purin-8-one d) Spebrutinib/AVL-292/CC-292
  i. CAS Number→1202757-89-8
    (see http://www.cas.org/content/chemical-substances/faqs)
  ii. PubChem ID→59174488
    (see https://pubchem.ncbi.nlm.nih.gov)

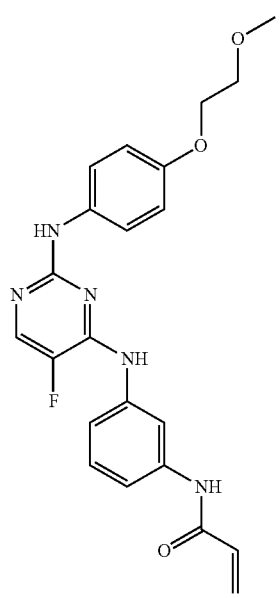 [SMILES: C=CC(=O)Nc1cccc(Nc2nc(Nc3ccc(OCCOC)cc3)ncc2F)c1]

Formula IV, Spebrutinib: N-[3-({5-fluoro-2-[4-(2-methoxyethoxy)anilino]pyrimidin-4-yl}amino)phenyl]prop-2-enamide e) BGB-3111 (Zanubrutinib)
  i. CAS Number→1691249-45-2
    (see http://www.cas.org/content/chemical-substances/faqs)

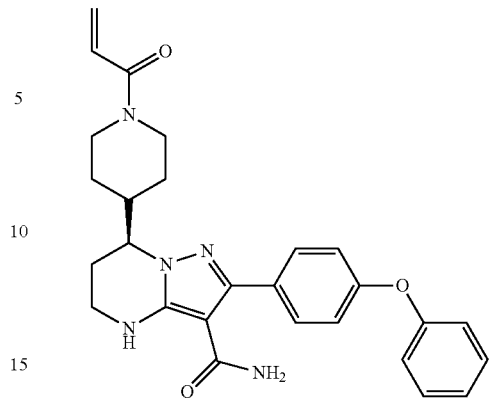

Formula V, Zanubrutinib: (7S)-4,5,6,7-Tetrahydro-7-[1-(1-oxo-2-propen-1-yl)-4-piperidinyl]-2-(4-phenoxyphenyl)pyrazolo[1,5-a]pyrimidine-3-carboxamide f) HM71224 (Poseltinib)
  i. CAS Number→1353552-97-2
    (see http://www.cas.org/content/chemical-substances/faqs)

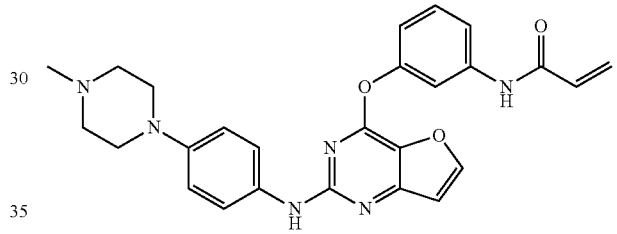

Formula VI, Poseltinib: N-(3-((2-((4-(4-methylpiperazin-1-yl)phenyl)amino)furo[3,2-d]pyrimidin-4-yl)oxy)phenyl)acrylamide In some embodiments, BTK polypeptide corresponds to Genbank accession no. CAA41728, version no. CAA41728.1, record update date: Feb. 2, 2011 10:07 AM. In one embodiment, the nucleic acid encoding BTK polypeptide corresponds to Genbank accession no. X58957, version no. X58957.1, record update date: Feb. 2, 2011 10:07 AM. In some embodiments, BTK polypeptide corresponds to Uniprot/Swiss-Prot accession No. Q06187.

PD1 Antagonists

Programmed death receptor I (PD1) is an immune-inhibitory receptor that is primarily expressed on activated T and B cells. Interaction with its ligands has been shown to attenuate T-cell responses both in vitro and in vivo. Blockade of the interaction between PD1 and one of its ligands, PD-L1, has been shown to enhance tumor-specific CD8+ T-cell immunity and may therefore be helpful in clearance of tumor cells by the immune system.

PD1 (encoded by the gene PdcdI) is an Immunoglobulin superfamily member related to CD28, and CTLA-4. PD1 has been shown to negatively regulate antigen receptor signalling upon engagement of its ligands (PD-L1 and/or PD-L2). The structure of murine PD1 has been solved as well as the co-crystal structure of mouse PD1 with human PD-L1 (Zhang, X., et al., (2004) Immunity 20: 337-347; Lin, et al., (2008) Proc. Natl. Acad. Sci. USA 105: 30I 1-6). PD1 and like family members are type I transmembrane glycoproteins containing an Ig Variable-type (V-type) domain responsible for ligand binding and a cytoplasmic tail that is responsible for the binding of signaling molecules. The cytoplasmic tail of PD1 contains two tyrosine-based signaling motifs, an ITIM (immunoreceptor tyrosine-based inhibition motif) and an ITSM (immunoreceptor tyrosine-based switch motif).

In humans, expression of PD1 (on tumor infiltrating lymphocytes) and/or PD-L1 (on tumor cells) has been found in a number of primary tumor biopsies assessed by immunohistochemistry. Such tissues include cancers of the lung, liver, ovary, cervix, skin, colon, glioma, bladder, breast, kidney, esophagus, stomach, oral squamous cell, urothelial cell, and pancreas as well as tumors of the head and neck (Brown, J. A., et al., (2003) J Immunol. 170: 1257-1266; Dong H., et al., (2002) Nat. Med. 8: 793-800; Wintterle, et al., (2003) Cancer Res. 63: 7462-7467; Strome, S. E., et al., (2003) Cancer Res. 63: 6501-6505; Thompson, R. H., et al., (2006) Cancer Res. 66: 3381-5; Thompson, et al., (2007) Clin. Cancer Res. 13:1 757-61; Nomi, T., et al., (2007) Clin. Cancer Res. 13: 2151-7). More strikingly, PD-ligand expression on tumor cells has been correlated to poor prognosis of cancer patients across multiple tumor types (reviewed in Okazaki and Honjo, (2007) Int. Immunol. 19: 813-824).

To date, numerous studies have shown that interaction of PD1 with its ligands (PD-L1 and PD-L2) leads to the inhibition of lymphocyte proliferation in vitro and in vivo. Blockade of the PD1/PD-L1 interaction could lead to enhanced tumor-specific T-cell immunity and therefore be helpful in clearance of tumor cells by the immune system. To address this issue, a number of studies were performed. In a murine model of aggressive pancreatic cancer (Nomi, T., et al. (2007) Clin. Cancer Res. 13: 2151-2157), the therapeutic efficacy of PD1/PD-L1 blockade was demonstrated. Administration of either PD1 or PD-L1 directed antibody significantly inhibited tumor growth. Antibody blockade effectively promoted tumor reactive CD8+ T cell infiltration into the tumor resulting in the up-regulation of anti-tumor effectors including IFN gamma, granzyme Band perforin. Additionally, the authors showed that PD1 blockade can be effectively combined with chemotherapy to yield a synergistic effect. In another study, using a model of squamous cell carcinoma in mice, antibody blockade of PD1 or PD-L1 significantly inhibited tumor growth (Tsushima, F., et al., (2006) Oral Oneal. 42: 268-274).

"PD1 antagonist" means any chemical compound or biological molecule that stimulates an immune reaction through inhibition of PD1 signalling.

To examine the extent of enhancement of, e.g., PD1 activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) with PD1 inhibitors is advantageous, because on the one hand, the ADC will directly kill the FTP positive tumor cells, while on the other hand the PD1 inhibitor will engage the patient's own immune system to eliminate the cancer cells. Next to FTP(+) tumor cells, FTP negative tumor cells in close proximity to FTP(+) tumor cells will potentially be killed by the bystander mechanism of the PBD-dimer released after cell kill of CD25(+) cells. Hence, the ADC will directly kill the tumor cells.

The resulting release of tumor associated antigens from cells that are killed with the PBD dimer will trigger the immune system, which will be further enhanced by the use of programmed cell death protein 1 (PD1) inhibitors, expressed on a large proportion of tumour infiltrating lymphocytes (TILs) from many different tumour types. Blockade of the PD1 pathway may enhance antitumour immune responses against the antigens released from the tumors killed by the ADC by diminishing the number and/or suppressive activity of intratumoral TReg cells.

The major function of PD1 is to limit the activity of T-cells at the time of an anti-inflammatory response to infection and to limit autoimmunity. PD1 expression is induced when T-cells become activated, and binding of one of its own ligands inhibits kinases involved in T-cell activation. Hence, in the tumor environment this may translate into a major immune resistance, because many tumours are highly infiltrated with TReg cells that probably further suppress effector immune responses. This resistance mechanism is alleviated by the use of PD1 inhibitors in combination with the ADC.

PD1 antagonists suitable for use as secondary agents in the present disclosure include:
 a) a PD1 antagonist which inhibits the binding of PD1 to its ligand binding partners.
 b) a PD1 antagonist which inhibits the binding of PD1 to PD-L1.
 c) a PD1 antagonist which inhibits the binding of PD-1 to PDL2.
 d) a PD1 antagonist which inhibits the binding of PD-1 to both PDLI and PDL2.
 e) a PD1 antagonist of parts (a) to (d) which is an antibody.

Specific PD1 antagonists suitable for use as secondary agents in the present disclosure include:
 a) pembrolizumab (brand name Keytruda)
  i. CAS Number→1374853-91-4
   (see http://www.cas.org/content/chemical-substances/faqs)
  ii. NCBI Pubchem reference→254741536
   (see https://pubchem.ncbi.nlm.nih.gov/)
  iii. DrugBank reference→DB09037
   (see https://www.drugbank.ca/)
  iv. Unique Ingredient Identifier (UNII)→DPT0O3T46P
   (see http://www.fda.gov/ForIndustry/DataStandards/SubstanceRegistrationSystem-UniqueIngredientIdentifierUNII/default.htm)
 b) nivolumab (brand name Opdivo)
  i. CAS Number→946414-94-4
   (see http://www.cas.org/content/chemical-substances/faqs)
  ii. DrugBank reference→DB09035
   (see https://www.drugbank.ca/)

c) MEDI0680 (formerly AMP-514)
   As described in WO2014/055648, WO2015/042246, WO2016/127052, WO2017/004016, WO2012/145493, U.S. Pat. No. 8,609,089, WO2016/007235, WO2016/011160; Int. J. Mol. Sci. 2016 July; 17(7): 1151, doi: 10.3390/ijms17071151; and Drug Discov Today, 2015 September; 20(9):1127-34. doi: 10.1016/j.drudis.2015.07.003.
   See also clinical trials NCT02271945 and NCT02013804 at https://clinicaltrials.gov/ct2/home
d) PDR001 (spartalizumab)
   i. CAS Number→1935694-88-4
      (see http://www.cas.org/content/chemical-substances/faqs)
   ii. Unique Ingredient Identifier (UNII)→QOG25L6Z8Z
      (see http://www.fda.gov/ForIndustry/DataStandards/SubstanceRegistrationSystem-UniqueIngredientIdentifierUNII/default.htm)
      ii. Unique Ingredient Identifier (UNII)→6QVL057INT
         (see http://www.fda.gov/ForIndustry/DataStandards/SubstanceRegistrationSystem-UniqueIngredientIdentifierUNII/default.htm)
      As described in WO2016/007235
      NCI thesaurus code→C121540
         (see https://ncit.nci.nih.gov/ncitbrowser/)
i) BGB-A317 (Tislelizumab)
   i. As described in U.S. Pat. No. 9,834,606 B2
   ii. See clinical trial NCT03209973 (https://clinicaltrials.gov/)
   iii. NCI thesaurus code C121775
      (see https://ncit.nci.nih.gov/ncitbrowser/)
j) BGB-108
   See WO2016/000619 and U.S. Pat. No. 8,735,553
k) AMP-224
   see clinical trial NCT02298946, https://clinicaltrials.gov/ct2/home

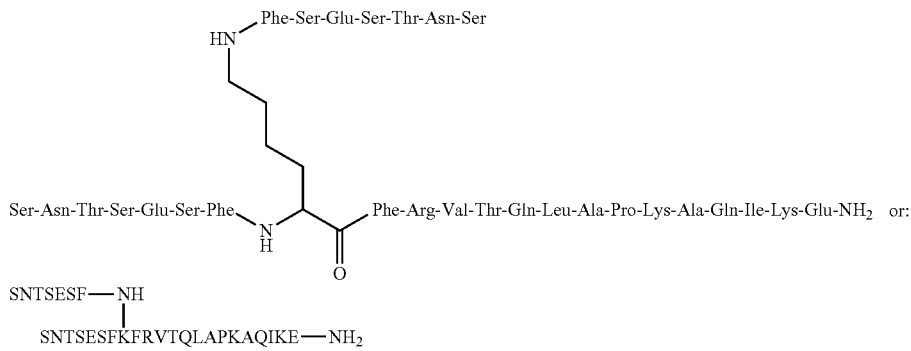

SNTSESF—NH
|
SNTSESFKFRVTQLAPKAQIKE—NH$_2$

As described in WO2016/007235 and WO2016/011160
NCI thesaurus code→C121625
   (see https://ncit.nci.nih.gov/ncitbrowser/)
e) Camrelizumab [INCSHR-1210] (Incyte)
   i. CAS Number→1798286-48-2
      (see http://www.cas.org/content/chemical-substances/faqs)
   ii. Unique Ingredient Identifier (UNII)→73096E137E
      (see http://www.fda.gov/ForIndustry/DataStandards/SubstanceRegistrationSystem-UniqueIngredientIdentifierUNII/default.htm)
f) AUNP12 (peptide) (Aurigene/PierreFabre)
   i. Disclosed in WO2011/161699 as SEQ ID NO:49 a.k.a. "compound 8", see Example 2 on page 77 of the A2 publication of WO2011/161699.
   ii. CAS Number→1353563-85-5
      (see http://www.cas.org/content/chemical-substances/faqs)
g) Pidilizumab (CT-01 1)
   i. CAS Number→1036730-42-3
      (see http://www.cas.org/content/chemical-substances/faqs)
   ii. Unique Ingredient Identifier (UNII)→B932PAQ1BQ
      (see http://www.fda.gov/ForIndustry/DataStandards/SubstanceRegistrationSystem-UniqueIngredientIdentifierUNII/default.htm)
h) Cemiplimab (formerly REGN-2810, SAR-439684)
   i. CAS Number→1801342-60-8 (see http://www.cas.org/content/chemical-substances/faqs)

In some embodiments, PD1 polypeptide corresponds to Genbank accession no. AAC51773, version no. AAC51773.1, record update date: Jun. 23, 2010 09:24 AM. In one embodiment, the nucleic acid encoding PD1 polypeptide corresponds to Genbank accession no. U64863, version no. U64863.1, record update date: Jun. 23, 2010 09:24 AM. In some embodiments, PD1 polypeptide corresponds to Uniprot/Swiss-Prot accession No. Q15116.

PD-L1 Antagonists

"PD-L1 antagonist" means any chemical compound or biological molecule that stimulates an immune reaction through inhibition of PD-L1 signalling.

To examine the extent of enhancement of, e.g., PD-L1 activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with PD-L1 inhibitors is advantageous because, on the one hand, the ADC will directly kill the FTP positive tumor cells while, on the other hand, the PD-L1 inhibitor will engage the patient's own immune system to eliminate the cancer cells.

Next to FTP(+) tumor cells, target negative tumor cells in close proximity to FTP(+) tumor cells will potentially be killed by the bystander mechanism of the PBD-dimer released after cell kill of FTP(+) cells. Hence, the ADC will directly kill the tumor cells. The resulting release of tumor associated antigens from cells that are killed with the PBD dimer will trigger the immune system, which will be further enhanced by the use of programmed cell death protein 1 ligand inhibitors (PD-L1, aka B7-H1 or CD274).

PD-L1 is commonly upregulated on the tumour cell surface from many different human tumours. Interfering with the PD1 ligand expressed on the tumor will avoid the immune inhibition in the tumor microenvironment and therefore blockade of the PD1 pathway using PDL1 inhibitors may enhance antitumour immune responses against the antigens released from the tumors killed by the ADC.

Combining an ADC, which targets a first target protein (FTP) with PD1 inhibitors is advantageous, because on the one hand, the ADC will directly kill the FTP positive tumor cells, while on the other hand the PD1 inhibitor will engage the patient's own immune system to eliminate the cancer cells. Next to FTP(+) tumor cells, FTP negative tumor cells in close proximity to FTP(+) tumor cells will potentially be killed by the bystander mechanism of the PBD-dimer released after cell kill of CD19(+) or CD22 (+) cells. Hence, the ADC will directly kill the tumor cells.

PD-L1 antagonists suitable for use as secondary agents in the present disclosure include PD-L1 antagonists that:
(a) are PD-L1 binding antagonists;
(b) inhibit the binding of PD-L1 to PD1;
(c) inhibit the binding of PD-L1 to B7-1;
(d) inhibit the binding of PD-L1 to both PD1 and B7-1;
(e) are anti-PD-L1 antibodies.

Specific PD-L1 antagonists suitable for use as secondary agents in the present disclosure include:
a) atezolizumab (MPDL3280A, brand name Tecentriq)
  i. CAS Number→1380723-44-3
    (see http://www.cas.org/content/chemical-substances/faqs)
  ii. DrugBank reference→DB11595
    (see https://www.drugbank.ca/)
  iii. Unique Ingredient Identifier (UNII)→52CMI0WC3Y
    (see http://www.fda.gov/ForIndustry/DataStandards/SubstanceRegistrationSystem-UniqueIngredientIdentifierUNII/default.htm)
b) BMS-936559/MDX-1105
  I. CAS Number→1422185-22-5
    (see http://www.cas.org/content/chemical-substances/faqs)
  II. see clinical trial NCT02028403, https://clinicaltrials.gov/ct2/home III. See WO2007/005874 for antibody sequences, in particular the:
  i. Antibody having:
    a. VH CDR1 = DYGFS
    b. VH CDR2 = WITAYNGNTNYAQKLQG
    c. VH CDR3 = DYFYGMDV
    d. VL CDR1 = RASQSVSSYLV
    e. VL CDR2 = DASNRAT
    f. VL CDR3 = QQRSNWPRT
  ii. Antibody having:
    a. VH CDR1 = TYAIS
    b. VH CDR2 = GIIPIFGKAHYAQKFQG
    c. VH CDR3 = KFHFVSGSPFGMDV
    d. VL CDR1 = RASQSVSSYLA
    e. VL CDR2 = DASNRAT
    f. VL CDR3 = QQRSNWPT
  iii. Antibody having:
    a. VH CDR1 = SYDVH
    b. VH CDR2 = WLHADTGITKFSQKFQG
    c. VH CDR3 = ERIQLWFDY
    d. VL CDR1 = RASQGISSWLA
    e. VL CDR2 = AASSLQS
    f. VL CDR3 = QQYNSYPYT
c) durvalumab/MEDI4736
  i. CAS Number→1428935-60-7
    (see http://www.cas.org/content/chemical-substances/faqs)
  ii. Unique Ingredient Identifier (UNII)→28X28X9OKV
    (see http://www.fda.gov/ForIndustry/DataStandards/SubstanceRegistrationSystem-UniqueIngredientIdentifierUNII/default.htm)
  iii. VH sequence EVQLVESGGGLVQPGGSLRLSCAAS<u>GFTFSRYWMS</u>WVRQAPGKGLEW
VA<u>NIKQDGSEKYYVDSVKG</u>RFTISRDNAKNSLYLQMNSLRAEDTAVYYC
AR<u>EGGWFGELAFDY</u>WGQGTLVTVSS iv. VL sequence EIVLTQSPGTLSLSPGERATLSC<u>RASQRVSSYLA</u>W
YQQKPGQAPRLLIY<u>DASSRAT</u>GIPDRFSGSGSGTDF
TLTISRLEPEDFAVYYC<u>QQYGSLPWT</u>FGQGTKVEIK d) Avelumab/MSB0010718C
  i. CAS Number→1537032-82-8
    (see http://www.cas.org/content/chemical-substances/faqs)

ii. Unique Ingredient Identifier (UNII)→KXG2PJ551I
(see http://www.fda.gov/ForIndustry/DataStandards/SubstanceRegistrationSystem-UniqueIngredientIdentifierUNII/default.htm)

In some embodiments, PD-L1 polypeptide corresponds to Genbank accession no. AAF25807, version no. AAF25807.1, record update date: Mar. 10, 2010 10:14 PM. In one embodiment, the nucleic acid encoding PD1 polypeptide corresponds to Genbank accession no. AF177937, version no. AF177937.1, record update date: Mar. 10, 2010 10:14 PM. In some embodiments, PD1 polypeptide corresponds to Uniprot/Swiss-Prot accession No. Q9NZQ7.

GITR Agonists

The term "glucocorticoid-induced TNF receptor" (abbreviated herein as "GITR"), also known as TNF receptor superfamily 18 (TNFRSF18, CD357), TEASR, and 312C2, as used herein, refers to a member of the tumor necrosis factor/nerve growth factor receptor family. GITR is a 241 amino acid type I transmembrane protein characterized by three cysteine pseudo-repeats in the extracellular domain and specifically protects T-cell receptorinduced apoptosis, although it does not protect cells from other apoptotic signals, including Fas triggering, dexamethasone treatment, or UV irradiation (Nocentini, G., et al. (1997) Proc. Natl. Acad. Sci. USA 94:6216-622).

GITR activation increases resistance to tumors and viral infections, is involved in autoimmune/inflammatory processes and regulates leukocyte extravasation (Nocentini supra; Cuzzocrea, et al. (2004) J Leukoc. Biol. 76:933-940; Shevach, et al. (2006) Nat. Rev. Immunol. 6:613-618; Cuzzocrea, et al. (2006) J Immunol. 1 77:631-641; and Cuzzocrea, et al. (2007) FASEB J 2I:I I 7-I29). In tumor mouse models, agonist GITR antibody, DTA-I, was combined with an antagonist CTLA-4 antibody, and showed synergistic results in complete tumor regression of advanced stage tumors in some test group mice (Ko, et al. (2005) J Exp. Med. 7:885-891).

The nucleic acid and amino acid sequences of human GITR (hGITR), of which there are three splice variants, are known and can be found in, for example GenBank Accession Nos. gi:40354198, gi:23238190, gi:23238193, and gi:23238196.

"GITR agonist" means any chemical compound or biological molecule that stimulates an immune reaction through activation of GITR signalling. Also contemplated are soluble GITR-L proteins, a GITR binding partner.

To examine the extent of enhancement of, e.g., GITR activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with GITR agonists is advantageous, because on the one hand the ADC will directly kill the FTP positive tumor cells, while on the other hand the GITR agonist will engage the patient's own immune system to eliminate the cancer cells. Next to FTP(+) tumor cells, target negative tumor cells in close proximity to FTP(+) tumor cells will potentially be killed by the bystander mechanism of the PBD-dimer released after cell kill of FTP(+) cells. Hence, the ADC will directly kill the tumor. The resulting release of tumor associated antigens from cells killed with the PBD dimer will trigger the immune system, which will be further enhanced by the use of a GITR agonist.

GITR (glucocorticoid-Induced TNFR-Related protein) is expressed transiently on activated T-cells and expressed constitutively at high levels on T-regs with further induction following activation. GITR ligation via its ligand GITRL stimulates both proliferation and function of both effector and regulatory CD4+ T cells. This promotes T-cell survival, and differentiation into effector cells, while abrogating suppression. Therefore it will be beneficial to target a FTP(+) tumor with the ADC, causing the antigenic cell death, while the GITR agonist induces a stronger, durable immune response.

Specific GITR agonists suitable for use as secondary agents in the present disclosure include:
a) MED11873, a GITR ligand fusion protein developed by MedImmune
   See WO2016/196792, US20160304607
   NCI thesaurus code→C124651
   (see https://ncit.nci.nih.gov/ncitbrowser)
   See also clinical trial NCT023126110 at https://clinicaltrials.gov/ct2/home
   See Tigue N J, Bamber L, Andrews J, et al. MEDI1873, a potent, stabilized hexameric agonist of human GITR with regulatory T-cell targeting potential. Oncoimmunology. 2017; 6(3):e1280645. doi: 10.1080/2162402X.2017.1280645.
b) INCAGN1876, is an agonist antibody targeting the glucocorticoid-induced TNFR-related protein, or GITR. Discovered during a collaboration with Ludwig Cancer Research. INCAGN1876 is being co-developed with
   See clinical trials NCT02583165 and NCT03277352 at https://clinicaltrials.gov/ct2/home
c) TRX518, a humanized a gylcosylated (Fc disabled) IgG1 anti-GITR mAb with immune-modulating activity developed by Leap Therapeutics
   See WO2006/105021 for sequences 58, 60-63; and EP2175884 sequences 1-7:
   VL comprising the sequence (CDR underline):

```
EIVMTQSPATLSVSPGERATLSCKASQNVGTNVAWY

QQKPGQAPRLLIYSASYRYSGIPARFSGSGSGTEFT

LTISSLQSEDFAVYYCQQYNTDPLTFGGGTKVEIK
```

VH comprising the sequence (CDR underline):

```
QVTLRESGPALVKPTQTLTLTCTFSGFSLSTSGMGVGWIRQP

PGKALEWLAHIWWDDDKYYNPSLKSRLTISKDTSKNQVVLTM

TNMDPVDTATYYCARTRRYFPFAYWGQGTLVTVS
```

QVTLRESGPALVKPTQTLTLTCTFS<u>GFSLSTSGMGVGW</u>IRQP

PGKALEWLA<u>HIWWDDDKYYQPSLKS</u>RLTISKDTSKNQVVLTM

TNMDPVDTATYYCAR<u>TRRYFPFAYW</u>GQGTLVTVS

See clinical trials NCT01239134 and NCT02628574 at https://clinicaltrials.gov/ct2/home NCI thesaurus code→C95023
(see https://ncit.nci.nih.gov/ncitbrowser)

d) GWN323, an anti-GITR agonistic monoclonal antibody, which activates GITRs found on multiple types of T-cells. GWN323 is developed by Novartis
See WO2016/196792
NCI thesaurus code→C128028
(see https://ncit.nci.nih.gov/ncitbrowser)
See clinical trial NCT02740270 at https://clinicaltrials.gov/ct2/home e) MK-1248, a humanized IgG4 anti-human glucocorticoid-induced tumor necrosis factor receptor (GITR) agonistic monoclonal antibody (MoAb) with significantly reduced effector function
See clinical trial NCT02553499 at https://clinicaltrials.gov/ct2/home
MK-1248 has the same CDR as MK4166 (see Sukumar et al., Cancer Res. 2017)

f) MK-4166, a humanized IgG1 anti-human glucocorticoid-induced tumor necrosis factor receptor (GITR) agonistic monoclonal antibody (MoAb) with potential immunomodulating activity (see Sukumar et al., Cancer Res. 2017).
See clinical trial NCT02132754 at https://clinicaltrials.gov/ct2/home
See Sukumar, et al., (2017), Cancer Research. 77. canres.1439.2016. 10.1158/0008-5472. CAN-16-1439.
NCI thesaurus code C116065
(see https://ncit.nci.nih.gov/ncitbrowser/)

g) BMS-986156, An anti-human glucocorticoid-induced tumor necrosis factor receptor (GITR; tumor necrosis factor superfamily member 18; TNFRSF18; CD357) agonistic monoclonal antibody
See clinical trial NCT02598960 at https://clinicaltrials.gov/ct2/home
NCI thesaurus code C132267
(see https://ncit.nci.nih.gov/ncitbrowser/)

Sequences of agonist anti-GITR antibodies are provided in WO2011/028683 and WO2006/105021.

In some embodiments, GITR polypeptide corresponds to Genbank accession no. AAD22635, version no. AAD22635.1, record update date: Mar. 10, 2010 09:42 PM. In one embodiment, the nucleic acid encoding GITR polypeptide corresponds to Genbank accession no. AF125304, version no. AF125304.1, record update date: Mar. 10, 2010 09:42 PM. In some embodiments, GITR polypeptide corresponds to Uniprot/Swiss-Prot accession No. Q9Y5U5.

OX40 Agonists

OX40 (CD134; TNFRSF4) is a member of the TNFR super-family and is expressed by CD4 and CD8 T cells during antigen-specific priming. OX40 expression is largely transient following TCR/CD3 cross-linking, and by the presence of inflammatory cytokines. In the absence of activating signals, relatively few mature T cell subsets express OX40 at biologically relevant levels. Generating optimal "killer" CD8 T cell responses requires T cell receptor activation plus co-stimulation, which can be provided through ligation of OX40 using a OX40 agonist. This activating mechanism augments T cell differentiation and cytolytic function leading to enhanced anti-tumor immunity. Therefore it will be beneficial to target a FTP(+) tumor with the ADC, causing the antigenic cell death, while the OX40 agonist induces a stronger, durable immune response.

The OX40 agonist may be selected from the group consisting of an OX40 agonist antibody, an OX40L agonist fragment, an OX40 oligomeric receptor, and an OX40 immunoadhesin. In some embodiments, the OX40 binding agonist is a trimeric OX40L-Fc protein.

In some embodiments, the OX40 binding agonist is an OX40L agonist fragment comprising one or more extracellular domains of OX40L. In some embodiments, the OX40 binding agonist is an OX40 agonist antibody that binds human OX40. In some embodiments, the OX40 agonist antibody depletes cells that express human OX40. In some embodiments, the OX40 agonist antibody depletes cells that express human OX40 in vitro. In some embodiments, the cells are CD4+ effector T cells. In some embodiments, the cells are Treg cells. In some embodiments, the depleting is by ADCC and/or phagocytosis. In some embodiments, the depleting is by ADCC. In some embodiments, the OX40 agonist antibody binds human OX40 with an affinity of less than or equal to about 1 nM. In some embodiments, the OX40 agonist antibody increases CD4+ effector T cell proliferation
and/or increasing cytokine production by the CD4+ effector T cell as compared to proliferation and/or cytokine production prior to treatment with anti-human OX40 agonist antibody. In some embodiments, the cytokine is gamma interferon. In some embodiments, the OX40 agonist antibody increases memory T cell proliferation and/or increasing cytokine production by the memory cell. In some embodiments, the cytokine is gamma interferon. In some embodiments, the OX40 agonist antibody inhibits Treg function. In some embodiments, the OX40 agonist antibody inhibits Treg suppression of effector T cell function. In some embodiments, effector T cell function is effector T cell proliferation and/or cytokine production. In some embodiments, the effector T cell is a CD4+ effector T cell. In some embodiments, the OX40 agonist antibody increases OX40 signal transduction in a target cell that expresses OX40. In some embodiments, OX40 signal transduction is detected by monitoring NFkB downstream signalling.

"OX40 agonist" means any chemical compound or biological molecule that stimulates an immune reaction through activation of OX40 signalling.

To examine the extent of enhancement of, e.g., OX40 activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more preferably at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with OX40 agonists is advantageous, because on the one hand the ADC will directly kill the FTP positive tumor cells, while on the other hand the OX40 agonist will engage the patient's own immune system to eliminate the cancer cells. Next to FTP(+) tumor cells, target negative tumor cells in close proximity to FTP(+) tumor cells will potentially be killed by the bystander mechanism of the PBD-dimer released after cell kill of FTP(+) cells. Hence, the ADC will directly kill the tumor. The resulting release of tumor associated antigens from cells killed with the PBD dimer will trigger the immune system, which will be further enhanced by the use of a OX40 agonist.

Specific OX40 agonists suitable for use as secondary agents in the present disclosure include:

a) MED10562 (aka Tavolixizumab, Tavolimab)
   i. CAS Number→1635395-25-3
      (see http://www.cas.org/content/chemical-substances/faqs)
   ii. Unique Ingredient Identifier (UNII)→ 4LU9B48U4D
      (see http://www.fda.gov/ForIndustry/DataStandards/SubstanceRegistrationSystem-UniqueIngredientIdentifierUNII/default.htm)
   See clinical trial NCT02318394 at https://clinicaltrials.gov/ct2/home
   As described in WO2015/095423, WO2015/153514, WO2016/073380 & WO2016/081384
   NCI thesaurus code→C120041
      (see https://ncit.nci.nih.gov/ncitbrowser/)
   Heavy Chain sequence:

QVQLQESGPGLVKPSQTLSLTCAVYGGSFSSGYWNW

IRKHPGKGLEYIGYISYNGITYHNPSLKSRITINRD

TSKNQYSLQLNSVTPEDTAVYYCARYKYDYDGGHAM

DYWGQGTLVTVSSASTKGPSVFPLAPSSKSTSGGTA

ALGCLVKDYFPEPVTVSWNSGALTSGVHTFPAVLQS

SGLYSLSSVVTVPSSSLGTQTYICNVNHKPSNTKVD

KRVEPKSCDKTHTCPPCPAPELLGGPSVFLFPPKPK

DTLMISRTPEVTCVVVDVSHEDPEVKFNWYVDGVEV

HNAKTKPREEQYNSTYRVVSVLTVLHQDWLNGKEYK

CKVSNKALPAPIEKTISKAKGQPREPQVYTLPPSRE

EMTKNQVSLTCLVKGFYPSDIAVEWESNGQPENNYK

TTPPVLDSDGSFFLYSKLTVDKSRWQQGNVFSCSVM

HEALHNHYTQKSLSLSPG

Light chain sequence:

DIQMTQSPSSLSASVGDRVTITCRASQDISNYLNWY

QQKPGKAPKLLIYYTSKLHSGVPSRFSGSGSGTDYT

LTISSLQPEDFATYYCQQGSALPWTFGQGTKVEIKR

TVAAPSVFIFPPSDEQLKSGTASVVCLLNNFYPREA

KVQWKVDNALQSGNSQESVTEQDSKDSTYSLSSTLT

LSKADYEKHKVYACEVTHQGLSSPVTKSFN RGEC b) MED16383 (Efizonerimod alfa)
   i. CAS Number→1635395-27-5
      (see http://www.cas.org/content/chemical-substances/faqs)
   ii. Unique Ingredient Identifier (UNII)→ 1MH7C2X8KE
      (see http://www.fda.gov/ForIndustry/DataStandards/SubstanceRegistrationSystem-UniqueIngredientIdentifierUNII/default.htm)
   See clinical trial NCT02221960 at https://clinicaltrials.gov/ct2/home
   As described in WO2015/095423, WO2016/081384, and WO2016/189124
   NCI thesaurus code→C118282
      (see https://ncit.nci.nih.gov/ncitbrowser/)
   Amino acid sequence (Seq ID no.17 from WO2016/189124):

ESKYGPPCPPCPAPEFLGGPSVFLFPPKPKDTLMIS

RTPEVTCVVVDVSQEDPEVQFNWYVDGVEVHNAKTK

PREEQFNSTYRVVSVLTVLHQDWLNGKEYKCKVSNK

GLPSSIEKTISKAKGQPREPQVYTLPPSQEEMTKNQ

VSLTCLVKGFYPSDIAVEWESNGQPENNYKTTPPVL

DSDGSFFLYSRLTVDKSRWQEGNVFSCSVMHEALHN

HYTQKSLSLSLGKDQDKIEALSSKVQQLERSIGLKD

LAMADLEQKVLEMEASTQVSHRYPRIQSIKVQFTEY

KKEKGFILTSQKEDEIMKVQNNSVIINCDGFYLISL

KGYFSQEVNISLHYQKDEEPLFQLKKVRSVNSLMVA

SLTYKDKVYLNVTTDNTSLDDFHVNGGELILIHQNP

GEFCVL c) MOXR0916 (also known as RG7888, Pogalizumab), a humanized anti-OX40 monoclonal antibody
   i. CAS Number→1638935-72-4
      (see http://www.cas.org/content/chemical-substances/faqs)
   ii. Unique Ingredient Identifier (UNII)→C78148TF1D
      (see http://www.fda.gov/ForIndustry/DataStandards/SubstanceRegistrationSystem-UniqueIngredientIdentifierUNII/default.htm)
   iii. NCI thesaurus code→C121376
      (see https://ncit.nci.nih.gov/ncitbrowser/)

d) OX40mAb24 (9B12)
   i. OX40mAb24 is a humanised version of 9B12. 9B12 is a murine IgGI, anti-OX40 mAb directed against the extracellular domain of human OX40 (CD134) (Weinberg, A. D., et al. J Immunother 29, 575-585 (2006)).
   ii. See WO2016/057667 Seq ID no.59 for OX40mAb24 VH sequence, no.29 for VL sequence (no.32 is an alternative VL):

VH sequence

```
QVQLQESGPGLVKPSQTLSLTCAVYGGSFSSGYWN

WIRKHPGKGLEYIGYISYNGITYHNPSLKSRITIN

RDTSKNQYSLQLNSVTPEDTAVYYCARYKYDYDGG

HAMDYWGQGTLVTVSS
```

VL sequence

```
DIQMTQSPSSLSASVGDRVTITCRASQDISNYLNWYQQKP

GKAPKLLIYYTSKLHSGVPSRFSGSGSGTDYTLTISSLQP

EDFATYYCQQGSALPWTFGQGTKVEIK
``` e) INCAGN1949
  i. See Gonzalez et al. 2016, DOI: 10.1158/1538-7445.AM2016-3204
  ii. See clinical trial NCT02923349 at https://clinicaltrials.gov/ct2/home
  iii. Antibody sequences are disclosed in WO2016/179517 A1:
    i. In particular, an antibody comprising the sequences:

```
VH CDR1 → GSAMH

VH CDR2 → RIRSKANSYATAYAASVKG

VH CDR3 → GIYDSSGYDY

VL CDR1 → RSSQSLLHSNGYNYLD

VL CDR2 → LGSNRAS

VL CDR3 → MQALQTPLT
``` ii. Such as, an antibody comprising the sequences:

```
VH →
EVQLVESGGGLVQPGGSLKLSCAASGFTFSGSAMHWVR

QASGKGLEWVGRIRSKANSYATAYAASVKGRFTISRDD

SKNTAYLQMNSLKTEDTAVYYCTSGIYDSSGYDYWGQG

TLVTVSS

VL →
DIVMTQSPLSLPVTPGEPASISCRSSQSLLHSNGYNYL

DWYLQKPGQSPQLLIYLGSNRASGVPDRFSGSGSGTDF

TLKISRVEAEDVGVYYCMQALQTPLTFGGGTKVEIK
``` g) GSK3174998, a humanized IgG1 agonistic anti-OX40 monoclonal antibody (mAb)
  See clinical trial NCT02528357 at https://clinicaltrials.gov/ct2/home
h) PF-04518600 (PF-8600) is an investigational, fully human, monoclonal antibody (mAb) that targets OX40 protein
  See patent WO 2017/130076 A1
  See clinical trial NCT02315066 at https://clinicaltrials.gov/ct2/home-NCI thesaurus code→C121927 (see https://ncit.nci.nih.gov/ncitbrowser/)

In some embodiments, OX40 polypeptide corresponds to Genbank accession no. CAA53576, version no. CAA53576.1, record update date: Feb. 2, 2011 10:10 AM. In one embodiment, the nucleic acid encoding OX40 polypeptide corresponds to Genbank accession no. X75962, version no. X75962.1, record update date: Feb. 2, 2011 10:10 AM. In some embodiments, OX40 polypeptide corresponds to Uniprot/Swiss-Prot accession No. P43489.

CTLA Antagonist

CTLA4 (CD152) is expressed on activated T cells and serves as a co-inhibitor to keep T cell responses in check following CD28-mediated T cell activation. CTLA4 is believed to regulate the amplitude of the early activation of naive and memory T cells following TCR engagement and to be part of a central inhibitory pathway that affects both antitumor immunity and autoimmunity. CTLA4 is expressed exclusively on T cells, and the expression of its ligands CD80 (B7.1) and CD86 (B7.2), is largely restricted to antigen-presenting cells, T cells, and other immune mediating cells. Antagonistic anti-CTLA4 antibodies that block the CTLA4 signalling pathway have been reported to enhance T cell activation. One such antibody, ipilimumab, was approved by the FDA in 2011 for the treatment of metastatic melanoma. Another anti-CTLA4 antibody, tremelimumab, was tested in phase III trials for the treatment of advanced melanoma, but did not significantly increase the overall survival of patients compared to the standard of care (temozolomide or dacarbazine) at that time.

"CTLA4 agonist" means any chemical compound or biological molecule that stimulates an immune reaction through inhibition of CTLA4 signalling.

To examine the extent of enhancement of, e.g., CTLA4 activity, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with CTLA4 inhibitors is advantageous, because on the one hand, the ADC will directly kill the FTP positive tumor cells, while on the other hand the CTLA4 inhibitor will engage the patient's own immune system to eliminate the cancer cells. Next to FTP(+) tumor cells, target negative tumor cells in close proximity to FTP(+) tumor cells will potentially be killed by the bystander mechanism of the PBD-dimer released after cell kill of FTP(+) cells. Hence, the ADC will directly kill the tumor. The resulting release of tumor associated antigens from cells killed with the PBD dimer will trigger the immune system, which will be further enhanced by the use of CTLA4 inhibitors expressed on a large proportion of tumour infiltrating lymphocytes (TILs) from many different tumour types.

The major function of CTLA4 (CD152) is to regulate the amplitude of the early stages of T cell activation, and as such it counteracts the activity of the T cell co-stimulatory receptor, CD28, In the tumor microenvironment. Blockade of the CTLA4 pathway may therefore enhance enhancement of effector CD4+ T cell activity, while it inhibits TReg cell-dependent immunosuppression. Therefore it will be beneficial to target a FTP(+) tumor with the ADC, causing the antigenic cell death, while the CTLA4 blockade induces a stronger immune, durable response.

Specific CTLA4 antagonists suitable for use as secondary agents in the present disclosure include:
a) ipilimumab
  i. CAS Number 477202-00-9
    (see http://www.cas.org/content/chemical-substances/faqs)
  ii. Unique Ingredient Identifier (UNII)→6T8C155666
    (see http://www.fda.gov/ForIndustry/DataStandards/SubstanceRegistrationSystem-UniqueIngredientIdentifierUNII/default.htm)
b) Tremelimumab
  i. CAS Number→745013-59-6
    (see http://www.cas.org/content/chemical-substances/faqs)
  ii. Unique Ingredient Identifier (UNII)→QEN1X95CIX
    (see http://www.fda.gov/ForIndustry/DataStandards/SubstanceRegistrationSystem-UniqueIngredientIdentifierUNII/default.htm)
  iii. VH sequence

```
                                           [SEQ ID NO. 1]
GVVQPGRSLRLSCAASGFTFSSYGMHWVRQAPGKGLE

WVAVIWYDGSNKYYADSVKGRFTISRDNSKNTLYLQM

NSLRAEDTAVYYCARDPRGATLYYYYGMDVWGQGTT

VTVSSASTKGPSVFPLAPCSRSTSESTAALGCLVKDY

FPEPVTVSWNSGALTSGVH
``` iv. VL sequence

```
                                           [SEQ ID NO. 2]
PSSLSASVGDRVTITCRASQSINSYLDWYQQKPGKA

PKLLIYAASSLQSGVPSRFSGSGSGTDFTLTISSLQ

PEDFATYYCQQYYSTPFTFGPGTKVEIKRTVAAPSV

FIFPPSDEQLKSGTASVVCLLNNFYPREAKV
```

In some embodiments, CTLA polypeptide corresponds to Genbank accession no. AAL07473, version no. AAL07473.1, record update date: Mar. 11, 2010 01:28 AM. In one embodiment, the nucleic acid encoding CTLA4 polypeptide corresponds to Genbank accession no. AF414120, version no. AF414120.1, record update date: Mar. 11, 2010 01:28 AM. In some embodiments, OX40 polypeptide corresponds to Uniprot/Swiss-Prot accession No. P16410.

Fludarabine and Cytarabine

Combination of agents with different action mechanisms is an established therapeutic principle for combating cancer. It can be a way of increasing anti-tumour activity when a synergic effect is shown and/or when reduced toxicity is observed. Antibody-drug conjugates, including those with a PBD warhead, may be particularly suited as combination partners because they are more targeted compared to conventional chemotherapy. As PBD dimers cross-link DNA in a covalent fashion, combining them with other agents that interfere with DNA synthesis via a different mechanism is likely to provide a benefit. Examples of such potential combinations are Fludarabine and Cytarabine.

Fludarabine

Fludarabine or fludarabine phosphate (Fludara) is a chemotherapy drug used in the treatment of hematological malignancies such as leukemias and lymphomas. It is a purine analog, which interferes with DNA by interfering with ribonucleotide reductase (RNAR) and DNA polymerase. It is active against both dividing and resting cells. Fludarabine has also been shown to suppress ERCC1 transcription and this may explain the observed synergy between Fludarabine and the PBD Dimer SJG136 (SG2000) against chronic lymphocytic leukaemia cells. CLAG/CLAG-M—Cladribine is another purine analogue that inhibits RNR.

Combining the ADC, which targets First Target Protein (FTP) positive lymphomas and leukemias, with Fludarabine is advantageous, because on the one hand, the ADC will directly kill the FTP positive tumor cells via a mechanisms depending on DNA cross-linking resulting in apoptosis, while on the other hand the Fludarabine will inhibit the cells RNA and DNA polymerase, while also suppressing the DNA repair enzymes needed to resolve the DNA cross-links induced by the PBD dimer.

To show that the ADC works synergistically with Fludarabine, a panel of FTP(+) cell lines will be co-treated with a range of concentration of both the ADC and Fludarabine. As negative controls, the same panel of cell lines will be co-treated with a range of concentrations of Fludarabine and a non-targeted control ADC or with a range of concentration of the ADC and vehicle. After incubation, two parameters will be measured: the amount of surface FTP (as determined by flow cytometry) and the in vitro cytotoxicity of the combinations (as determined by CellTiter-Glo® or MTS assays). Cytotoxic synergy is calculated by transforming the cell viability data into fraction affected, and calculating the combination index using the CalcuSyn analysis program.

CAS Number→21679-14-1
  (see http://www.cas.org/content/chemical-substances/faqs)
ii. NCBI Pubchem reference→657237
  (see https://pubchem.ncbi.nlm.nih.gov/)
iii. IUPHAR/BPS reference→4802
  (see http://www.guidetopharmacology.org/)
iv. Unique Ingredient Identifier (UNII)→1X9VK9O1SC
  (see http://www.fda.gov/ForIndustry/DataStandards/SubstanceRegistrationSystemUniqueIngredientIdentifierUNII/default.htm)

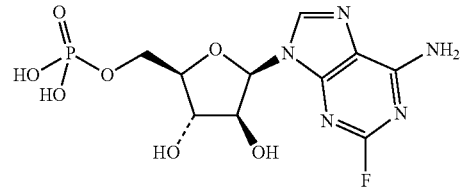 [SMILES: Nc1nc(F)nc2c1ncn2[C@@H]1O[C@H](COP(=O)(O)O)[C@@H](O)[C@@H]1O]

Formula VII, Fludarabine: [(2R,3R,4S,5R)-5-(6-amino-2-fluoro-purin-9-yl)-3,4-dihydroxy-oxolan-2-yl]methoxyphosphonic acid Cytarabine Cytarabine or cytosine arabinoside (Cytosar-U or Depocyt) is a antimetabolic chemotherapy drug used in the treatment of hematological malignancies such as acute myeloid leukemia (AML) and non-Hodgkin lymphoma. It is also known as ara-C (arabinofuranosyl cytidine). It kills cancer cells by interfering with DNA synthesis. It is actively metabolized to cytosine arabinoside triphosphate, which damages DNA when the cell cycle holds in the S phase (synthesis of DNA). Rapidly dividing cells, which require DNA replication for mitosis, are therefore most affected. Cytosine arabinoside also inhibits both DNA and RNA polymerases and nucleotide reductase enzymes needed for DNA synthesis.

Combining the ADC, which targets First Target Protein (FTP) positive lymphomas and leukemias, with Cytarabine is advantageous, because on the one hand, the ADC will directly kill the FTP positive tumor cells via a mechanisms depending on DNA cross-linking resulting in apoptosis, while on the other hand the Cytarabine will inhibit the cells RNA and DNA polymerase, while also suppressing DNA synthesis.

To show that the ADC works synergistically with Cytarabine, a panel of FTP(+) cell lines will be co-treated with a range of concentration of both the ADC and Cytarabine. As negative controls, the same panel of cell lines will be co-treated with a range of concentrations of Cytarabine and a non-targeted control ADC or with a range of concentration of the ADC and vehicle. After incubation, two parameters will be measured: the amount of surface FTP (as determined by flow cytometry) and the in vitro cytotoxicity of the combinations (as determined by CellTiter-Glo® or MTS assays). Cytotoxic synergy is calculated by transforming the cell viability data into fraction affected, and calculating the combination index using the CalcuSyn analysis program (see example 4).

CAS Number→147-94-4
(see http://www.cas.org/content/chemical-substances/faqs)
ii. NCBI Pubchem reference→6253
(see https://pubchem.ncbi.nlm.nih.gov/)
iii. IUPHAR/BPS reference→4827
(see http://www.guidetopharmacology.org/)
iv. Unique Ingredient Identifier (UNII)→04079A1RDZ
(see http://www.fda.gov/ForIndustry/DataStandards/SubstanceRegistrationSystemUniqueIngredientIdentifierUNII/default.htm)

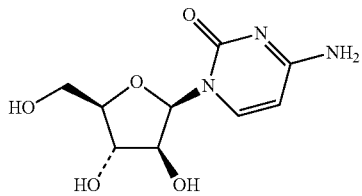 [SMILES: Nc1ccn([C@@H]2O[C@H](CO)[C@@H](O)[C@@H]2O)c(=O)n1]

Formula VIII, Cytarabine: 4-amino-1-[(2R,3S,4R,5R)-3,4-dihydroxy-5-(hydroxymethyl)oxolan-2-yl] pyrimidin-2-one Hypomethylating Agent The term "hypomethylating agent" refers to a class of compounds that interfere with DNA methylation which is the addition of a methyl group to the 5-position of the cytosine pyrimidine ring or the nitrogen in position 6 of the adenine purine ring. DNA methylation stably alters the gene expression pattern in cells i.e. decrease gene expression (i.e. for the Vitamin D receptor). Hypomethylating agent are compounds that can inhibit methylation, resulting in the expression of the previously hypermethylated silenced genes. Cytidine analogs such as 5-azacytidine (azacitidine) and 5-aza-2'-deoxycytidine (decitabine are the most commonly used Hypomethylating agent. These compounds work by binding to the enzymes that catalyse the methylation reaction, i.e. DNA methyltransferases.

To examine the extent of hypomethylation, samples or assays comprising a given, e.g., protein, gene, cell, or organism, are treated with a potential activating or inhibiting agent and are compared to control samples treated with an inactive control molecule. Control samples are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 20%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Combining an ADC, which targets a first target protein (FTP) positive lymphomas and leukemias with a hypomethylating agent is advantageous, because on the one hand the ADC will directly kill the FTP positive tumor cells, while on the other hand the a hypomethylating agent will interfere with DNA methylation. This interference is by way of causing demethylation in that sequence, which adversely affects the way that cell regulatory proteins are able to bind to the DNA/RNA substrate. This activity synergises with the ADC because PBD dimers cross-link DNA in a covalent fashion, so combining them with other agents that interfere with DNA synthesis via a different mechanism provides a benefit.

Specific Hypomethylating agents suitable for use as secondary agents in the present disclosure include:
a) 5-azacytidine (azacitidine)
i. CAS Number→320-67-2
(see http://www.cas.org/content/chemical-substances/faqs)
ii. NCBI Pubchem reference→9444
(see https://pubchem.ncbi.nlm.nih.gov/)
iii. IUPHAR/BPS reference→6796
(see http://www.guidetopharmacology.org/)
iv. Unique Ingredient Identifier (UNII)→M801H13NRU
(see http://www.fda.gov/ForIndustry/DataStandards/SubstanceRegistrationSystem-UniqueIngredientIdentifierUNII/default.htm)

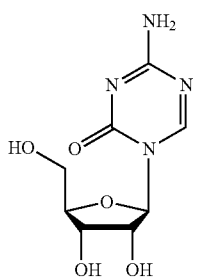

Formula IX, 5-azacytidine: 4-Amino-1-β-D-ribofurano-syl-1,3,5-triazin-2(1H)-one
  b) 5-aza-2'-deoxycytidine (decitabine)
    i. CAS Number→2353-33-5
       (see http://www.cas.org/content/chemical-substances/faqs)
    ii. NCBI Pubchem reference→451668
       (see https://pubchem.ncbi.nlm.nih.gov/)
    iii. IUPHAR/BPS reference→6805
       (see http://www.guidetopharmacology.org/)
    iv. Unique Ingredient Identifier (UNII)→776B62CQ27
       (see http://www.fda.gov/ForIndustry/DataStandards/SubstanceRegistrationSystem-UniqueIngredientIdentifierUNII/default.htm)

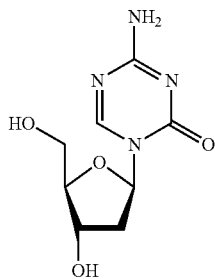

Formula X, b) 5-aza-2'-deoxycytidine: 4-Amino-1-(2-deoxy-β-D-erythro-pentofuranosyl)-1,3,5-triazin-2(1H)-one Advantageous Properties of the Described Combinations Both the ADC and secondary agent when used as a single agent in isolation have demonstrated clinical utility—for example, in the treatment of cancer. However, as described herein, combination of the ADC and secondary agent is expected to provide one or more of the following advantages over treatment with either ADC or secondary agent alone:
  1) effective treatment of a broader range of cancers;
  2) effective treatment of resistant or refractory forms of disorders such as cancer, and individuals with disorders such as cancer who have relapsed after a period of remission;
  3) increased response rate to treatment; and/or
  4) Increased durability of treatment.

Effective treatment of a broader range of cancers as used herein means that following treatment with the combination a complete response is observed with a greater range of recognised cancer types. That is, a complete response is seen from cancer types not previously reported to completely respond to either ADC or secondary agent alone.

Effective treatment of a resistant, refractory, or relapsed forms as used herein means that following treatment with the combination a complete response is observed in individuals that are either partially or completely resistant or refractory to treatment with either ADC or secondary agent alone (for example, individuals who show no response or only partial response following treatment with either agent alone, or those with relapsed disorder). In some embodiments, a complete response following treatment with the ADC/secondary agent combination is observed at least 10% of individuals that are either partially or completely resistant or refractory to treatment with either ADC or secondary agent alone. In some embodiments, a complete response following treatment with the ADC/secondary agent combination is observed at least 20%, at least 30%, at least 40%, at least 50%, at least 60%, at least 70%, at least 80%, at least 90%, at least 95%, at least 98%, or at least 99% of individuals that are either partially or completely resistant or refractory to treatment with either ADC or secondary agent alone.

Increased response rate to treatment as used herein means that following treatment with the combination a complete response is observed in a greater proportion of individuals than is observed following treatment with either ADC or secondary agent alone. In some embodiments, a complete response following treatment with the ADC/secondary agent combination is observed at least 10% of treated individuals. In some embodiments, a complete response following treatment with the ADC/secondary agent combination is observed at least 20%, at least 30%, at least 40%, at least 50%, at least 60%, at least 70%, at least 80%, at least 90%, at least 95%, at least 98%, or at least 99% of treated individuals.

Increased durability of treatment as used herein means that average duration of complete response in individuals treated with the combination is longer than in individuals who achieve complete response following treatment with either ADC or secondary agent alone. In some embodiments, the average duration of a complete response following treatment with the ADC/secondary agent combination is at least 6 months. In some embodiments, the average duration of a complete response following treatment with the ADC/secondary agent combination is at least 12 months, at least 18 months, at least 24 months, at least 3 years, at least 4 years, at least 5 years, at least 6 years, at least 7 years, at least 8 years, at least 9 years, at least 10 years, at least 15 years, or at least 20 years.

'Complete response' is used herein to mean the absence of any clinical evidence of disease in an individual. Evidence may be assessed using the appropriate methodology in the art, for example CT or PET scanning, or biopsy where appropriate. The number of doses required to achieve complete response may be one, two, three, four, five, ten or more. In some embodiments the individuals achieve complete response no more than a year after administration of the first dose, such as no more than 6 months, no more than 3 months, no more than a month, no more than a fortnight, or no more than a week after administration of the first dose.

Treated Disorders

The combined therapies described herein include those with utility for anticancer activity. In particular, in certain aspects the therapies include an antibody conjugated, i.e. covalently attached by a linker, to a PBD drug moiety, i.e. toxin. When the drug is not conjugated to an antibody, the PBD drug has a cytotoxic effect. The biological activity of the PBD drug moiety is thus modulated by conjugation to an antibody. The antibody-drug conjugates (ADC) of the disclosure selectively deliver an effective dose of a cytotoxic agent to tumor tissue whereby greater selectivity, i.e. a lower efficacious dose, may be achieved.

Thus, in one aspect, the present disclosure provides combined therapies comprising administering an ADC which binds a first target protein for use in therapy, wherein the method comprises selecting a subject based on expression of the target protein.

In one aspect, the present disclosure provides a combined therapy with a label that specifies that the therapy is suitable for use with a subject determined to be suitable for such use. The label may specify that the therapy is suitable for use in a subject has expression of the first target protein, such as overexpression of the first target protein. The label may specify that the subject has a particular type of cancer.

The first target protein is preferably CD25. The cancer may be lymphoma, such as AML. The label may specify that the subject has a CD25+lymphoma.

In a further aspect there is also provided a combined therapy as described herein for use in the treatment of a proliferative disease. Another aspect of the present disclosure provides the use of a conjugate compound in the manufacture of a medicament for treating a proliferative disease.

One of ordinary skill in the art is readily able to determine whether or not a candidate combined therapy treats a proliferative condition for any particular cell type. For example, assays which may conveniently be used to assess the activity offered by a particular compound are described below.

The combined therapies described herein may be used to treat a proliferative disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), lymphomas, leukemias, psoriasis, bone diseases, fibroproliferative disorders (e.g. of connective tissues), and atherosclerosis. Cancers of interest include, but are not limited to, leukemias and ovarian cancers.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Proliferative disorders of particular interest include, but are not limited to, Hodgkin's and non-Hodgkin's Lymphoma, including diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL) and leukemias such as Hairy cell leukemia (HCL), Hairy cell leukemia variant (HCL-v), Acute Myeloid Leukaemia (AML), and Acute Lymphoblastic Leukaemia (ALL) such as Philadelphia chromosome-positive ALL (Ph+ALL) or Philadelphia chromosome-negative ALL (Ph−ALL) [Fielding A., Haematologica. 2010 January; 95(1): 8-12].

The proliferative disease may be characterised by the presence of a neoplasm comprising both CD25+ve and CD25−ve cells.

The proliferative disease may be characterised by the presence of a neoplasm composed of CD25−ve neoplastic cells, optionally wherein the CD25−ve neoplastic cells are associated with CD25+ve non-neoplastic cells such as CD25+ve T-cells.

The target neoplasm or neoplastic cells may be all or part of a solid tumour.

"Solid tumor" herein will be understood to include solid haematological cancers such as lymphomas (Hodgkin's lymphoma or non-Hodgkin's lymphoma) which are discussed in more detail herein.

Solid tumors may be neoplasms, including non-haematological cancers, comprising or composed of CD25+ve neoplastic cells. Solid tumors may be neoplasms, including non-haematological cancers, infiltrated with CD25+ve cells, such as CD25+ve T-cells; such solid tumours may lack expression of CD25 (that is, comprise or be composed of CD25-ve neoplastic cells).

For example, the solid tumour may be a tumour with high levels of infiltrating T-cells, such as infiltrating regulatory T-cells (Treg; Ménétrier-Caux, C., et al., Targ Oncol (2012) 7:15-28; Arce Vargas et al., 2017, Immunity 46, 1-10; Tanaka, A., et al., Cell Res. 2017 January; 27(1):109-118). Accordingly, the solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

It is contemplated that the combined therapies of the present disclosure may be used to treat various diseases or disorders, e.g. characterized by the overexpression of a tumor antigen. Exemplary conditions or hyperproliferative disorders include benign or malignant tumors; leukemia, haematological, and lymphoid malignancies. Others include neuronal, glial, astrocytal, hypothalamic, glandular, macrophagal, epithelial, stromal, blastocoelic, inflammatory, angiogenic and immunologic, including autoimmune disorders and graft-versus-host disease (GVHD).

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

Autoimmune diseases for which the combined therapies may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g. ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, graft-versus-host disease (GVHD), and autoimmune endocrine disorders (such as, for example, diabetic-related autoimmune diseases such as insulin-dependent diabetes mellitus (IDDM), Addison's disease, and autoimmune thyroid disease (e.g. Graves' disease and thyroiditis)). More preferred such diseases include, for example, rheumatoid arthritis, ulcerative colitis, ANCA-associated vasculitis, lupus, multiple sclerosis, Sjogren's syndrome, Graves' disease, IDDM, pernicious anemia, thyroiditis, and glomerulonephritis.

In some aspects, the subject has a proliferative disorder selected from (classical) Hodgkin lymphomas, with mixed cellularity type (Hodgkin-/Reed-Sternbert-Cells: CD25+/−), or non-Hodgkin lymphoma, including B-cell chronic lymphatic leukemia, diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL) and leukemias such as Hairy cell leukemia (HCL), Hairy cell leukemia variant (HCL-v), Acute Myeloid Leukaemia (AML), Acute Lymphoblastic Leukaemia (ALL) such as Philadelphia chromosome-positive ALL (Ph+ALL) or Philadelphia chromosome-negative ALL (Ph− ALL) [Fielding A., Haematologica. 2010 January; 95(1): 8-12], small cell lymphocytic lymphoma, adult T-cell leukemia/lymphoma, or anaplastic large cell lymphoma.

In some aspects, the subject has a proliferative disease characterised by the presence of a neoplasm comprising both CD25+ve and CD25−ve cells.

The proliferative disease may be characterised by the presence of a neoplasm composed of CD25−ve neoplastic cells, optionally wherein the CD25−ve neoplastic cells are associated with CD25+ve non-neoplastic cells such as CD25+ve T-cells.

The target neoplasm or neoplastic cells may be all or part of a solid tumour.

Solid tumors may be neoplasms, including non-haematological cancers, comprising or composed of CD25+ve neoplastic cells. Solid tumors may be neoplasms, including non-haematological cancers, infiltrated with CD25+ve cells, such as CD25+ve T-cells; such solid tumours may lack expression of CD25 (that is, comprise or be composed of CD25-ve neoplastic cells).

For example, the solid tumour may be a tumour with high levels of infiltrating T-cells, such as infiltrating regulatory T-cells (Treg; Ménétrier-Caux, C., et al., Targ Oncol (2012) 7:15-28; Arce Vargas et al., 2017, Immunity 46, 1-10; Tanaka, A., et al., Cell Res. 2017 January; 27(1):109-118). Accordingly, the solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

Classical Hodgkins lymphoma includes the subtypes nodular sclerosing, lymphocyte predominant, lymphocyte depleted and mixed cellularity. The Hodgkins lymphoma subtype may not be defined. In certain aspects, the patients tested according to the methods here have Hodgkins lymphoma of the nodular sclerosing and mixed cellularity subtypes.

In certain aspects, the subject has diffuse large B cell lymphoma or peripheral T cell lymphoma, including the anaplastic large cell lymphoma and angioimmunoblastic T cell lymphoma subtypes.

Patient Selection

In certain aspects, the individuals are selected as suitable for treatment with the combined treatments before the treatments are administered.

As used herein, individuals who are considered suitable for treatment are those individuals who are expected to benefit from, or respond to, the treatment. Individuals may have, or be suspected of having, or be at risk of having cancer. Individuals may have received a diagnosis of cancer. In particular, individuals may have, or be suspected of having, or be at risk of having, lymphoma. In some cases, individuals may have, or be suspected of having, or be at risk of having, a solid cancer that has tumour associated non-tumor cells that express a first target protein, such as infiltrating T-cells that express a first target protein.

In some aspects, individuals are selected on the basis of the amount or pattern of expression of a first target protein. In some aspects, the selection is based on expression of a first target protein at the cell surface. So, in some cases, individuals are selected on the basis they have, or are suspected of having, are at risk of having cancer, or have received a diagnosis of a proliferative disease characterised by the presence of a neoplasm comprising cells having a low level of surface expression of a first target protein (such as CD25). The neoplasm may be composed of cells having a low level of surface expression of a first target protein (such as CD25). In some cases, low levels of surface expression means that mean number of anti-FTP antibodies bound per neoplastic cell is less than 20000, such as less than 10000, less than 5000, less than 2000, less than 1000, less than 500, less than 400, less than 300, less than 200, or less than 100. In some cases, the mean number of bound antibodies per cell is measured using the assay described in Example 9.

In some aspects, individuals are selected on the basis they have a neoplasm comprising both CD25+ve and CD25−ve cells. The neoplasm may be composed of CD25−ve neoplastic cells, optionally wherein the CD25−ve neoplastic cells are associated with CD25+ve non-neoplastic cells such as CD25+ve T-cells. The neoplasm or neoplastic cells may be all or part of a solid tumour. The solid tumour may be partially or wholly CD25−ve, and may be infiltrated with CD25+ve cells, such as CD25+ve T-cells.

In certain aspects, the target is a second target protein. In some aspects, the selection is based on expression of a second target protein at the cell surface.

In some aspects, the selection is based on levels of both a first target protein and a second target protein at the cell surface.

In some cases, expression of the target in a particular tissue of interest is determined. For example, in a sample of lymphoid tissue or tumor tissue. In some cases, systemic expression of the target is determined. For example, in a sample of circulating fluid such as blood, plasma, serum or lymph.

In some aspects, the individual is selected as suitable for treatment due to the presence of target expression in a sample. In those cases, individuals without target expression may be considered not suitable for treatment.

In other aspects, the level of target expression is used to select a individual as suitable for treatment. Where the level of expression of the target is above a threshold level, the individual is determined to be suitable for treatment.

In some aspects, the presence of a first target protein and/or a second target protein in cells in the sample indicates that the individual is suitable for treatment with a combination comprising an ADC and a secondary agent. In other aspects, the amount of first target protein and/or a second target protein expression must be above a threshold level to indicate that the individual is suitable for treatment. In some aspects, the observation that first target protein and/or a second target protein localisation is altered in the sample as compared to a control indicates that the individual is suitable for treatment.

In some aspects, an individual is indicated as suitable for treatment if cells obtained from lymph node or extra nodal sites react with antibodies against first target protein and/or a second target protein as determined by IHC.

In some aspects, a patient is determined to be suitable for treatment if at least 5%, 10%, 15%, 20%, 25%, 30%, 35%, 40%, 45%, 50%, 55%, 60%, 65%, 70%, 75%, 80%, 85%, 90% or more of all cells in the sample express a first target protein. In some aspects disclosed herein, a patient is determined to be suitable for treatment if at least at least 10% of the cells in the sample express a first target protein.

In some aspects, a patient is determined to be suitable for treatment if at least 5%, 10%, 15%, 20%, 25%, 30%, 35%, 40%, 45%, 50%, 55%, 60%, 65%, 70%, 75%, 80%, 85%, 90% or more of all cells in the sample express a second target protein. In some aspects disclosed herein, a patient is determined to be suitable for treatment if at least at least 10% of the cells in the sample express a second target protein.

The first target protein is preferably CD25.

The second target protein may be BTK, PD1, PDL1, GITR, OX40, or CTLA. The second target protein is preferably PD-L1.

Samples

The sample may comprise or may be derived from: a quantity of blood; a quantity of serum derived from the individual's blood which may comprise the fluid portion of the blood obtained after removal of the fibrin clot and blood cells; a quantity of pancreatic juice; a tissue sample or biopsy; or cells isolated from said individual.

A sample may be taken from any tissue or bodily fluid. In certain aspects, the sample may include or may be derived from a tissue sample, biopsy, resection or isolated cells from said individual.

In certain aspects, the sample is a tissue sample. The sample may be a sample of tumor tissue, such as cancerous tumor tissue. The sample may have been obtained by a tumor biopsy. In some aspects, the sample is a lymphoid tissue sample, such as a lymphoid lesion sample or lymph node biopsy. In some cases, the sample is a skin biopsy.

In some aspects the sample is taken from a bodily fluid, more preferably one that circulates through the body. Accordingly, the sample may be a blood sample or lymph sample. In some cases, the sample is a urine sample or a saliva sample.

In some cases, the sample is a blood sample or blood-derived sample. The blood derived sample may be a selected fraction of a individual's blood, e.g. a selected cell-containing fraction or a plasma or serum fraction.

A selected cell-containing fraction may contain cell types of interest which may include white blood cells (WBC), particularly peripheral blood mononuclear cells (PBC) and/or granulocytes, and/or red blood cells (RBC). Accordingly, methods according to the present disclosure may involve detection of a first target polypeptide or nucleic acid in the blood, in white blood cells, peripheral blood mononuclear cells, granulocytes and/or red blood cells.

The sample may be fresh or archival. For example, archival tissue may be from the first diagnosis of an individual, or a biopsy at a relapse. In certain aspects, the sample is a fresh biopsy.

The first target polypeptide is preferably CD25.

Individual Status

The individual may be an animal, mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orang-utang, gibbon), or a human.

Furthermore, the individual may be any of its forms of development, for example, a foetus. In one preferred embodiment, the individual is a human. The terms "subject", "patient" and "individual" are used interchangeably herein.

In some aspects disclosed herein, an individual has, or is suspected as having, or has been identified as being at risk of, cancer. In some aspects disclosed herein, the individual has already received a diagnosis of cancer. The individual may have received a diagnosis of (classical) Hodgkins lymphoma (including nodular sclerosing, lymphocyte predominant, lymphocyte, or mixed cellularity type, or where the type is unspecified), diffuse large B cell lymphoma (DLBCL) or peripheral T cell lymphoma (PTCL) (including the subtypes ALCL: anaplastic large cell lymphoma or AITL: angioimmunoblastic T cell lymphoma). In some cases, the individual has received a diagnosis of nodular sclerosing or mixed cellularlity classical Hodgkins lymphoma, diffuse large B cell lymphoma, or angioimmunoblastic T cell lymphoma.

In some cases the individual has, or is suspected of having, a proliferative disease characterised by the presence of a neoplasm comprising both CD25+ve and CD25−ve cells. The neoplasm may be composed of CD25−ve neoplastic cells, optionally wherein the CD25−ve neoplastic cells are associated with CD25+ve non-neoplastic cells such as CD25+ve T-cells. The neoplasm or neoplastic cells may be all or part of a solid tumour.

The solid tumor may be a neoplasm, including a non-haematological cancer, comprising or composed of CD25+ve neoplastic cells. The solid tumor may be a neoplasm, including a non-haematological cancer, infiltrated with CD25+ve cells, such as CD25+ve T-cells; such solid tumours may lack expression of CD25 (that is, comprise or be composed of CD25−ve neoplastic cells).

In some cases the individual has, or is suspected of having, a solid tumour with high levels of infiltrating T-cells, such as infiltrating regulatory T-cells (Treg; Ménétrier-Caux, C., et al., Targ Oncol (2012) 7:15-28; Arce Vargas et al., 2017, Immunity 46, 1-10; Tanaka, A., et al., Cell Res. 2017 January; 27(1):109-118). The some or all of the neoplastic cells in the tumour may be CD25−ve. The solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

In some cases, the individual has received a diagnosis of (classical) Hodgkins lymphoma (mixed cellularity type), or non-Hodgkins lymphoma (including B-cell chronic lymphatic leukemia, diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL) and leukemias such as Hairy cell leukemia (HCL), Hairy cell leukemia variant (HCL-v), Acute Myeloid Leukaemia (AML), Acute Lymphoblastic Leukaemia (ALL) such as Philadelphia chromosome-positive ALL (Ph+ALL) or Philadelphia chromosome-negative ALL (Ph−ALL) [Fielding A., Haematologica. 2010 January; 95(1): 8-12], small cell lymphocytic lymphoma, adult T-cell leukemia/lymphoma, and anaplastic large cell lymphoma.

In some cases, the individual has received a diagnosis of cutaneous T-cell lymphoma, mycosis fungoides, Sezary syndrome, systemic mastocytosis, B-cell lymphoma, non-hematopoietic tumors, peripheral T cell lymphoma and histiocytic proliferation.

In some cases, the individuals has, or is suspected of having, or has received a diagnosis of a proliferative disease characterised by the presence of a neoplasm comprising cells having a low level of surface expression of a first target protein (such as CD25). The neoplasm may be composed of cells having a low level of surface expression of a first target protein (such as CD25). In some cases, low levels of surface expression means that mean number of anti-FTP antibodies bound per neoplastic cell is less than 20000, such as less than 10000, less than 5000, less than 2000, less than 1000, less than 500, less than 400, less than 300, less than 200, or less than 100. In some cases, the mean number of bound antibodies per cell is measured using the assay described in Example 9.

In some cases, the individual has received a diagnosis of a proliferative disease characterised by the presence of a neoplasm comprising both CD25+ve and CD25−ve cells. The neoplasm may be composed of CD25−ve neoplastic cells, optionally wherein the CD25−ve neoplastic cells are associated with CD25+ve non-neoplastic cells such as CD25+ve T-cells. The neoplasm or neoplastic cells may be all or part of a solid tumour.

The solid tumor may be a neoplasm, including a non-haematological cancer, comprising or composed of CD25+ve neoplastic cells. The solid tumor may be a neoplasm, including a non-haematological cancer, infiltrated with CD25+ve cells, such as CD25+ve T-cells; such solid tumours may lack expression of CD25 (that is, comprise or be composed of CD25−ve neoplastic cells).

In some cases, the individual has received a diagnosis of a solid tumour with high levels of infiltrating T-cells, such as infiltrating regulatory T-cells (Treg; Ménétrier-Caux, C., et al., Targ Oncol (2012) 7:15-28; Arce Vargas et al., 2017, Immunity 46, 1-10; Tanaka, A., et al., Cell Res. 2017 January; 27(1):109-118). The some or all of the neoplastic cells in the tumour may be CD25−ve. The solid tumour may be pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

In some cases, the individual has received a diagnosis of a solid cancer containing CD25+expressing infiltrating T-cells.

The Individual may be undergoing, or have undergone, a therapeutic treatment for that cancer. The subject may, or may not, have previously received ADCX25. In some cases the cancer is lymphoma, including Hodgkins or non-Hodgkins lymphoma.

Controls

In some aspects, target expression in the individual is compared to target expression in a control. Controls are useful to support the validity of staining, and to identify experimental artefacts.

In some cases, the control may be a reference sample or reference dataset. The reference may be a sample that has been previously obtained from a individual with a known degree of suitability. The reference may be a dataset obtained from analyzing a reference sample.

Controls may be positive controls in which the target molecule is known to be present, or expressed at high level, or negative controls in which the target molecule is known to be absent or expressed at low level.

Controls may be samples of tissue that are from individuals who are known to benefit from the treatment. The tissue may be of the same type as the sample being tested. For example, a sample of tumor tissue from a individual may be compared to a control sample of tumor tissue from a individual who is known to be suitable for the treatment, such as a individual who has previously responded to the treatment.

In some cases the control may be a sample obtained from the same individual as the test sample, but from a tissue known to be healthy. Thus, a sample of cancerous tissue from a individual may be compared to a non-cancerous tissue sample.

In some cases, the control is a cell culture sample.

In some cases, a test sample is analyzed prior to incubation with an antibody to determine the level of background staining inherent to that sample.

In some cases an isotype control is used. Isotype controls use an antibody of the same class as the target specific antibody, but are not immunoreactive with the sample. Such controls are useful for distinguishing non-specific interactions of the target specific antibody.

The methods may include hematopathologist interpretation of morphology and immunohistochemistry, to ensure accurate interpretation of test results. The method may involve confirmation that the pattern of expression correlates with the expected pattern. For example, where the amount of a first target protein and/or a second target protein expression is analyzed, the method may involve confirmation that in the test sample the expression is observed as membrane staining, with a cytoplasmic component. The method may involve confirmation that the ratio of target signal to noise is above a threshold level, thereby allowing clear discrimination between specific and non-specific background signals.

The first target protein is preferably CD25.

The second target protein may be BTK, PD1, PDL1, GITR, OX40, or CTLA. The second target protein is preferably PD-L1.

Methods of Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount" or "effective amount" as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

Similarly, the term "prophylactically-effective amount," as used herein, pertains to that amount of an active compound, or a material, composition or dosage from comprising an active compound, which is effective for producing some desired prophylactic effect, commensurate with a reasonable benefit/risk ratio, when administered in accordance with a desired treatment regimen.

Disclosed herein are methods of therapy. Also provided is a method of treatment, comprising administering to a subject in need of treatment a therapeutically-effective amount of an ADC and a secondary agent. The term "therapeutically effective amount" is an amount sufficient to show benefit to a subject. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors. The subject may have been tested to determine their eligibility to receive the treatment according to the methods disclosed herein. The method of treatment may comprise a step of determining whether a subject is eligible for treatment, using a method disclosed herein.

The ADC may comprise an anti-CD25 antibody. The anti-CD25 antibody may be HuMax-TAC™. The ADC may comprise a drug which is a PBD dimer. The ADC may be a anti-CD25-ADC, and in particular, ADCX25. The ADC may be an ADC disclosed in WO2014/057119.

The secondary agent may be:
(a) a Bruton's Tyrosine Kinase inhibitor (BTKi), such as Ibrutinib (Imbruvica), Acalabrutinib/ACP-196, ONO/GS-4059, Spebrutinib/AVL-292/CC-292, HM71224 (Poseltinib) or BGB-3111 (Zanubrutinib);
(b) a PD1 antagonist, such as pembrolizumab, nivolumab, MEDI0680, PDR001 (spartalizumab), Camrelizumab, AUNP12, Pidilizumab, Cemiplimab (REGN-2810), AMP-224, BGB-A317 (Tisleizumab), or BGB-108;
(c) a PD-L1 antagonist, such as atezolizumab (Tecentriq), BMS-936559/MDX-1105, durvalumab/MED14736, or MSB0010718C (Avelumab);
(d) a GITR (Glucocorticoid-Induced TNFR-Related protein) agonist, such as MED11873, TRX518, GWN323, MK-1248, MK-4166, BMS-986156 or INCAGN1876;
(e) an OX40 agonist, such as MEDI0562, MEDI6383, MOXR0916, RG7888, OX40mAb24, INCAGN1949, GSK3174998, or PF-04518600;
(f) a CTLA-4 antagonist, such as ipilimumab (brand name Yervoy) or Tremelimumab (Originally developed by Pfizer, now Medimmune);
(g) Fludarabine or Cytarabine; or
(h) a hypomethylating agent, such as cytidine analogs—for example, 5-azacytidine (azacitidine) and 5-aza-2'-deoxycytidine (decitabine).

The treatment may involve administration of the ADC/secondary agent combination alone or in further combination with other treatments, either simultaneously or sequentially dependent upon the condition to be treated. Examples of treatments and therapies include, but are not limited to, chemotherapy (the administration of active agents, including, e.g. drugs, such as chemotherapeutics); surgery; and radiation therapy.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: Lenalidomide (REVLIMID®, Celgene), Vorinostat (ZOLINZA®, Merck), Panobinostat (FARYDAK®, Novartis), Mocetinostat (MGCD0103), Everolimus (ZORTRESS®, CERTICAN®, Novartis), Bendamustine (TREAKISYM®, RIBOMUSTIN®, LEVACT®, TREANDA®, Mundipharma International), erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo [4.3.0] nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omegal1 (*Angew Chem. Intl. Ed.*

*Engl.* (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above. Combinations of agents may be used, such as CHP (doxorubicin, prednisone, cyclophosphamide), or CHOP (doxorubicin, prednisone, cyclophopsphamide, vincristine).

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), ofatumumab (ARZERRA®, GSK), pertuzumab (PERJETA™, OMNITARG™, 2C4, Genentech), trastuzumab (HERCEPTIN®, Genentech), tositumomab (Bexxar, Corixia), MDX-060 (Medarex) and the antibody drug conjugate, gemtuzumab ozogamicin (MYLOTARG®, Wyeth).

Humanized monoclonal antibodies with therapeutic potential as chemotherapeutic agents in combination with the conjugates of the disclosure include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Compositions according to the present disclosure are preferably pharmaceutical compositions. Pharmaceutical compositions according to the present disclosure, and for use in accordance with the present disclosure, may comprise, in addition to the active ingredient, i.e. a conjugate compound, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Dosage

It will be appreciated by one of skill in the art that appropriate dosages of the ADC and/or the secondary agent, and compositions comprising these active elements, can vary from subject to subject. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the subject. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

In certain aspects, the dosage of ADC is determined by the expression of a first target protein observed in a sample obtained from the subject. Thus, the level or localisation of expression of the first target protein in the sample may be indicative that a higher or lower dose of ADC is required. For example, a high expression level of the first target protein may indicate that a higher dose of ADC would be suitable. In some cases, a high expression level of the first target protein may indicate the need for administration of another agent in addition to the ADC. For example, administration of the ADC in conjunction with a chemotherapeutic agent. A high expression level of the first target protein may indicate a more aggressive therapy.

In certain aspects, the dosage level is determined by the expression of a first target protein on neoplastic cells in a sample obtained from the subject. For example, when the target neoplasm is composed of, or comprises, neoplastic cells expressing the first target protein.

In certain aspects, the dosage level is determined by the expression of a first target protein on cells associated with the target neoplasm. For example, the target neoplasm may be a solid tumour composed of, or comprising, neoplastic cells that express the first target protein. For example, the target neoplasm may be a solid tumour composed of, or comprising, neoplastic cells that do not express the first target protein. The cells expressing the first target protein may be non-neoplastic cells infiltrating the solid tumour, such as infiltrating T-cells.

In certain aspects, the dosage of the secondary agent is determined by the expression of a second target protein observed in a sample obtained from the subject. Thus, the level or localisation of expression of the second target protein in the sample may be indicative that a higher or lower dose of secondary agent is required. For example, a high expression level of the second target protein may indicate that a higher dose of secondary agent would be suitable. In some cases, a high expression level of the second target protein may indicate the need for administration of another agent in addition to the secondary agent. For example, administration of the secondary agent in conjunction with a chemotherapeutic agent. A high expression level of the second target protein may indicate a more aggressive therapy.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of each active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

In one embodiment, each active compound is administered to a human subject according to the following dosage regime: about 100 mg, 3 times daily.

In one embodiment, each active compound is administered to a human subject according to the following dosage regime: about 150 mg, 2 times daily.

In one embodiment, each active compound is administered to a human subject according to the following dosage regime: about 200 mg, 2 times daily.

However in one embodiment, each conjugate compound is administered to a human subject according to the following dosage regime: about 50 or about 75 mg, 3 or 4 times daily.

In one embodiment, each conjugate compound is administered to a human subject according to the following dosage regime: about 100 or about 125 mg, 2 times daily.

For the ADC, where it is a PBD bearing ADC, the dosage amounts described above may apply to the conjugate (including the PBD moiety and the linker to the antibody) or to the effective amount of PBD compound provided, for example the amount of compound that is releasable after cleavage of the linker.

The first target protein is preferably CD25. The ADC may comprise an anti-CD25 antibody. The anti-CD25 antibody may be HuMax-TACT™. The ADC may comprise a drug which is a PBD dimer. The ADC may be an anti-CD25-ADC, and in particular, is preferably ADCX25. The ADC may be an ADC disclosed in WO2014/057119.

The second target protein may be BTK, PD1, PDL1, GITR, OX40, or CTLA. The second target protein is preferably PD-L1. The secondary agent may be:
  (a) a Bruton's Tyrosine Kinase inhibitor (BTKi), such as Ibrutinib (Imbruvica), Acalabrutinib/ACP-196, ONO/GS-4059, Spebrutinib/AVL-292/CC-292, HM71224 (Poseltinib) or BGB-3111 (Zanubrutinib);
  (b) a PD1 antagonist, such as pembrolizumab, nivolumab, MED10680, PDR001 (spartalizumab), Camrelizumab, AUNP12, Pidilizumab, Cemiplimab (REGN-2810), AMP-224, BGB-A317 (Tisleizumab), or BGB-108;
  (c) a PD-L1 antagonist, such as atezolizumab (Tecentriq), BMS-936559/MDX-1105, durvalumab/MEDI4736, or MSB0010718C (Avelumab);

(d) a GITR (Glucocorticoid-Induced TNFR-Related protein) agonist, such as MEDI1873, TRX518, GWN323, MK-1248, MK-4166, BMS-986156 or INCAGN1876;
(e) an OX40 agonist, such as MEDI0562, MEDI6383, MOXR0916, RG7888, OX40mAb24, INCAGN1949, GSK3174998, or PF-04518600;
(f) a CTLA-4 antagonist, such as ipilimumab (brand name Yervoy) or Tremelimumab (Originally developed by Pfizer, now Medimmune);
(g) Fludarabine or Cytarabine; or
(h) a hypomethylating agent, such as cytidine analogs—for example, 5-azacytidine (azacitidine) and 5-aza-2'-deoxycytidine (decitabine).

Antibodies

The term "antibody" herein is used in the broadest sense and specifically covers monoclonal antibodies, polyclonal antibodies, dimers, multimers, multispecific antibodies (e.g., bispecific antibodies), intact antibodies (also described as "full-length" antibodies) and antibody fragments, so long as they exhibit the desired biological activity, for example, the ability to bind a first target protein (Miller et al (2003) *Jour. of Immunology* 170:4854-4861). Antibodies may be murine, human, humanized, chimeric, or derived from other species such as rabbit, goat, sheep, horse or camel.

An antibody is a protein generated by the immune system that is capable of recognizing and binding to a specific antigen. (Janeway, C., Travers, P., Walport, M., Shlomchik (2001) *Immuno Biology, 5th Ed.*, Garland Publishing, New York). A target antigen generally has numerous binding sites, also called epitopes, recognized by Complementarity Determining Regions (CDRs) on multiple antibodies. Each antibody that specifically binds to a different epitope has a different structure. Thus, one antigen may have more than one corresponding antibody. An antibody may comprise a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass, or allotype (e.g. human G1m1, G1m2, G1m3, non-G1m1 [that, is any allotype other than G1m1], G1m17, G2m23, G3m21, G3m28, G3m11, G3m5, G3m13, G3m14, G3m10, G3m15, G3m16, G3m6, G3m24, G3m26, G3m27, A2m1, A2m2, Km1, Km2 and Km3) of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', F(ab')$_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler et al (1975) *Nature* 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies include "primatized" antibodies comprising variable domain antigen-binding sequences derived from a non-human primate (e.g. Old World Monkey or Ape) and human constant region sequences.

An "intact antibody" herein is one comprising VL and VH domains, as well as a light chain constant domain (CL) and heavy chain constant domains, CH1, CH2 and CH3. The constant domains may be native sequence constant domains (e.g. human native sequence constant domains) or amino acid sequence variant thereof. The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

Anti-CD25 antibodies are known in the art and are useful in the methods disclosed herein. These include antibodies 4C9 (obtainable from Ventana Medical Systems, Inc.). Other suitable antibodies include antibody AB12 described in WO 2004/045512 (Genmab A/S), IL2R.1 (obtainable from Life Technologies, catalogue number MA5-12680) and RFT5 (described in U.S. Pat. No. 6,383,487). Other suitable antibodies include 8489 (143-13) (obtainable from Life Technologies, catalogue number MA1-91221), SP176 (obtainable from Novus, catalogue number NBP2-21755), 1B5D12 (obtainable from Novus, catalogue number NBP2-37349), 2R12 (obtainable from Novus, catalogue number NBP2-21755), or BC96 (obtainable from BioLegend, catalogue number V T-072) and M-A251 (obtainable from BioLegend, catalogue number IV A053). Other suitable anti-CD25 antibodies are daclizumab (Zenapax™) and basiliximab (Simulect™), both of which have been approved for clinical use.

Anti-PD-L1 antibodies are known in the art and are useful in the methods disclosed herein. These antibodies include Atezolizumab (MPDL3280; CAS number 1380723-44-3), Avelumab (MSB0010718C; CAS number 1537032-82-8), and Durvalumab (CAS number 1428935-60-7).

BRIEF DESCRIPTION OF THE FIGURES

Embodiments and experiments illustrating the principles of the disclosure will now be discussed with reference to the accompanying figures in which:

FIG. 1. Sequences

FIG. 4. In vitro cytotoxicity data against the Karpas299 cell line of Cytarabine alone (top graph) or in combination with ADCx25 (bottom graph).

FIG. 5. In vitro cytotoxicity data against the KG-1 cell line of cytarabine alone (top graph) or in combination with ADCx25 (bottom graph).

FIG. 6. Surface CD25 levels on the Karpas299 cell line (left graph) and KG-1 cell line (right graph) incubated with or without Cytarabine.

Figure 2:
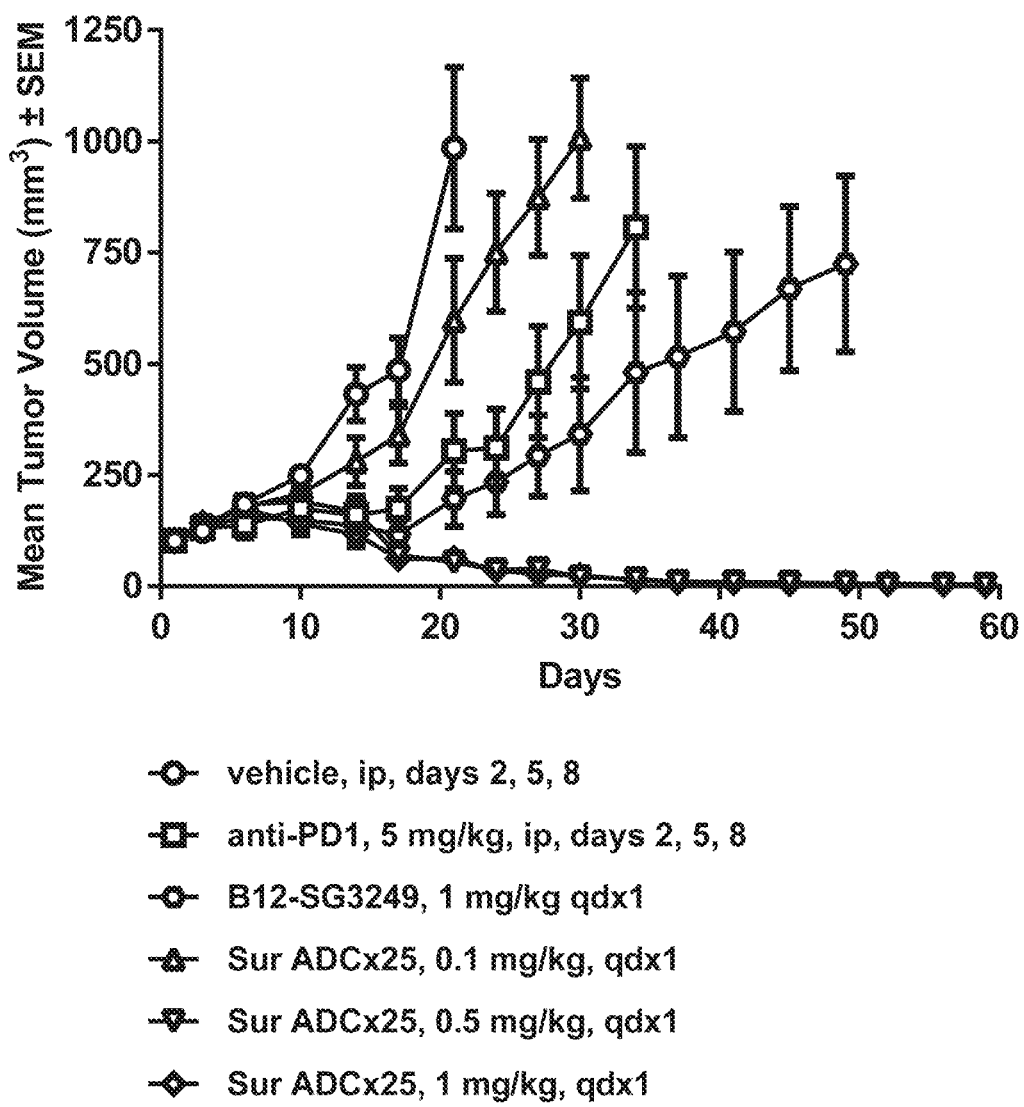
FIG. 2. In vivo tumour volume following mono-treatment with surrogate ADCx25, anti-PD1 treatment, or control ADC (as per Example 4)

The disclosure includes the combination of the aspects and preferred features described except where such a combination is clearly impermissible or expressly avoided.

The section headings used herein are for organizational purposes only and are not to be construed as limiting the subject matter described.

Aspects and embodiments of the present disclosure will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

SOME EMBODIMENTS

The following paragraphs describe some specific embodiments of the present disclosure:

1. A method for treating cancer in an individual, the method comprising administering to the individual an effective amount of ADCX25 and a secondary agent.

2. A first composition comprising ADCX25 for use in a method of treating cancer in an individual, wherein the treatment comprises administration of the first composition in combination with a second composition comprising a secondary agent.

3. A first composition comprising a secondary agent for use in a method of treating a disorder in an individual, wherein the treatment comprises administration of the first composition in combination with a second composition comprising ADCX25.

4. Use of ADCX25 in the manufacture of a medicament for treating cancer in an individual, wherein the medicament comprises ADCX25, and wherein the treatment comprises administration of the medicament in combination with a composition comprising a secondary agent.

5. Use of a PD1 antagonist in the manufacture of a medicament for treating cancer in an individual, wherein the medicament comprises a secondary agent, and wherein the treatment comprises administration of the medicament in combination with a composition comprising ADCX25.

6. A kit comprising:
   a first medicament comprising ADCX25;
   a second medicament comprising a secondary agent; and, optionally,
   a package insert comprising instructions for administration of the first medicament to an individual in combination with the second medicament for the treatment of cancer.

7. A kit comprising a medicament comprising ADCX25 and a package insert comprising instructions for administration of the medicament to an individual in combination with a composition comprising a secondary agent for the treatment of cancer.

8. A kit comprising a medicament comprising a secondary agent and a package insert comprising instructions for administration of the medicament to an individual in combination with a composition comprising ADCX25 for the treatment of cancer.

9. A pharmaceutical composition comprising ADCX25 and a secondary agent.

10. A method of treating cancer in an individual, the method comprising administering to the individual an effective amount of the composition of paragraph 9.

11. The composition of paragraph 9 for use in a method of treating cancer in an individual.

12. The use of the composition of paragraph 9 in the manufacture of a medicament for treating cancer in an individual.

13. A kit comprising the composition of paragraph 9 and a set of instructions for administration of the medicament to an individual for the treatment of cancer.

14. The composition, method, use, or kit according to any previous paragraph, wherein the treatment comprises administering ADCX25 before the secondary agent, simultaneous with the secondary agent, or after the secondary agent.

15. The composition, method, use, or kit according to any previous paragraph, wherein the treatment further comprises administering a chemotherapeutic agent.

16. The composition, method, use, or kit according to any previous paragraph, wherein the individual is human.

17. The composition, method, use, or kit according to any previous paragraph, wherein the individual has, or has been determined to have, cancer.

18. The composition, method, use, or kit according any previous paragraph, wherein the individual has, or has been has been determined to have, a cancer characterised by the presence of a neoplasm comprising both CD25+ve and CD25−ve cells.

19. The composition, method, use, or kit according any previous paragraph, wherein the individual has, or has been has been determined to have, a cancer characterised by the presence of a neoplasm comprising, or composed of, CD25−ve neoplastic cells.

20. The composition, method, use, or kit according to any previous paragraph, wherein the cancer or neoplasm is all or part of a solid tumour.

21. The composition, method, use, or kit according to any previous paragraph, wherein the individual has, or has been has been determined to have, a cancer which expresses CD25 or CD25+ tumour-associated non-tumour cells, such as CD25+infiltrating T-cells.

22. The composition, method, use, or kit according to any previous paragraph, wherein the individual has, or has been has been determined to have, a cancer which expresses a low level of surface expression of CD25.

23. The composition, method, use, or kit according to any preceding paragraph, wherein the individual has, or has been has been determined to have, a cancer which expresses a second target protein.

24. The composition, method, use, or kit according to any one of the preceding paragraphs, wherein the treatment:
a) effectively treats a broader range of disorders,
b) effectively treats resistant, refractory, or relapsed disorders,
c) has an increased response rate, and/or
d) has increased durability;
as compared to treatment with either ADCX25 or the secondary agent alone.

25. The composition, method, use, or kit according to any one of the preceding paragraphs, wherein the cancer is selected from the group comprising:
Hodgkin's and non-Hodgkin's Lymphoma, including diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL);
leukemias such as Hairy cell leukemia (HCL), Hairy cell leukemia variant (HCL-v), Acute Myeloid Leukaemia (AML), Acute Lymphoblastic Leukaemia (ALL) such as Philadelphia chromosome-positive ALL (Ph+ALL) or Philadelphia chromosome-negative ALL (Ph−ALL);
pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

26. A composition, method, use, or kit according to any one of the preceding paragraphs, wherein the secondary agent is a Bruton's Tyrosine Kinase inhibitor (BTKi).

27. A composition, method, use, or kit according to paragraph 26, wherein the Bruton's Tyrosine Kinase inhibitor (BTKi) is selected from Ibrutinib (Imbruvica), Acalabrutinib/ACP-196, ONO/GS-4059, Spebrutinib/AVL-292/CC-292, HM71224 (Poseltinib) and BGB-3111 (Zanubrutinib).

28. A composition, method, use, or kit according to any one of paragraphs 1 to 25, wherein the secondary agent is a PD1 antagonist.

29. A composition, method, use, or kit according to paragraph 28, wherein the PD1 antagonist is selected from pembrolizumab, nivolumab, MEDI0680, PDR001 (spartalizumab), Camrelizumab, AUNP12, Pidilizumab Cemiplimab (REGN-2810), AMP-224, BGB-A317 (Tisleizumab), and BGB-108.

30. A composition, method, use, or kit according to any one of paragraphs 1 to 25, wherein the secondary agent is a PD-L1 antagonist.

31. A composition, method, use, or kit according to paragraph 30, wherein the PD-L1 antagonist is selected from atezolizumab (Tecentriq), BMS-936559/MDX-1105, durvalumab/MEDI4736, and MSB0010718C (Avelumab).

32. A composition, method, use, or kit according to any one of paragraphs 1 to 25, wherein the secondary agent is a GITR (glucocorticoid-Induced TNFR-Related protein) agonist.

33. A composition, method, use, or kit according to paragraph 32, wherein the GITR (Glucocorticoid-Induced TNFR-Related protein) agonist is selected from MEDI1873, TRX518, GWN323, MK-1248, MK 4166, BMS-986156 and INCAGN1876.

34. A composition, method, use, or kit according to any one of paragraphs 1 to 25, wherein the secondary agent is a OX40 agonist.

35. A composition, method, use, or kit according to paragraph 34, wherein the OX40 agonist is selected from MEDI0562, MEDI6383, MOXR0916, RG7888, OX40mAb24, INCAGN1949, GSK3174998, and PF-04518600.

36. A composition, method, use, or kit according to any one of paragraphs 1 to 25, wherein the secondary agent is a CTLA-4 antagonist.

37. A composition, method, use, or kit according to paragraph 36, wherein the CTLA-4 antagonist is selected from ipilimumab and Tremelimumab.

38. A composition, method, use, or kit according to any one of paragraphs 1 to 25, wherein the secondary agent is Fludarabine.

39. A composition, method, use, or kit according to any one of paragraphs 1 to 25, wherein the secondary agent is Cytarabine.

40. A composition, method, use, or kit according to any one of paragraphs 1 to 25, wherein the secondary agent is a hypomethylating agent.

41. A composition, method, use, or kit according to paragraph 40, wherein the hypomethylating agent is selected from 5-azacytidine (azacitidine) and 5-aza-2'-deoxycytidine (decitabine).

42. A composition, method, use, or kit according to paragraph 40, wherein the hypomethylating agent is decitabine.

STATEMENTS OF INVENTION

1. A method for treating a disorder in an individual, the method comprising administering to the individual an effective amount of an ADC and a secondary agent.

2. A first composition comprising an ADC for use in a method of treating a disorder in an individual, wherein the treatment comprises administration of the first composition in combination with a second composition comprising a secondary agent.

3. A first composition comprising a secondary agent for use in a method of treating a disorder in an individual, wherein the treatment comprises administration of the first composition in combination with a second composition comprising an ADC.

4. Use of an ADC in the manufacture of a medicament for treating a disorder in an individual, wherein the medicament comprises an ADC, and wherein the treatment comprises administration of the medicament in combination with a composition comprising a secondary agent.

5. Use of a secondary agent in the manufacture of a medicament for treating a disorder in an individual, wherein the medicament comprises a secondary agent, and wherein the treatment comprises administration of the medicament in combination with a composition comprising an ADC.

6. A kit comprising:
a first medicament comprising an ADC;
a second medicament comprising a secondary agent; and, optionally,
a package insert comprising instructions for administration of the first medicament to an individual in combination with the second medicament for the treatment of a disorder.

7. A kit comprising a medicament comprising an ADC and a package insert comprising instructions for administration of the medicament to an individual in combination with a composition comprising a secondary agent for the treatment of a disorder.

8. A kit comprising a medicament comprising a secondary agent and a package insert comprising instructions for administration of the medicament to an individual in combination with a composition comprising an ADC for the treatment of a disorder.

9. A pharmaceutical composition comprising an ADC and a secondary agent.

10. A method of treating a disorder in an individual, the method comprising administering to the individual an effective amount of the composition of paragraph 9.

11. The composition of paragraph 9 for use in a method of treating a disorder in an individual.

12. The use of the composition of paragraph 9 in the manufacture of a medicament for treating a disorder in an individual.

13. A kit comprising the composition of paragraph 9 and a set of instructions for administration of the medicament to an individual for the treatment of a disorder.

14. The composition,' method, use, or kit according to any previous paragraph, wherein the treatment comprises administering the ADC before the secondary agent, simultaneous with the secondary agent, or after the secondary agent.

15. The composition, method, use, or kit according to any previous paragraph, wherein the treatment further comprises administering a chemotherapeutic agent.

16. The composition, method, use, or kit according to any previous paragraph, wherein the individual is human.

17. The composition, method, use, or kit according to any preceding paragraph, wherein the individual has a disorder or has been determined to have a disorder.

18. The composition, method, use, or kit according to paragraph 17, wherein the individual has, or has been has been determined to have, a cancer which expresses a first target protein (FTP) or FTP+ tumour-associated non-tumour cells, such as FTP+infiltrating T-cells.

19. The composition, method, use, or kit according to any preceding paragraph, wherein the individual has, or has been has been determined to have, a cancer which expresses a second target protein (STP).

20. The composition, method, use, or kit according to any one of the preceding paragraphs, wherein the treatment:
a) effectively treats a broader range of disorders,
b) effectively treats resistant, refractory, or relapsed disorders,
c) has an increased response rate, and/or
d) has increased durability;
as compared to treatment with either the ADC or the secondary agent alone.

21. A composition, method, use, or kit according to any previous paragraph, wherein the ADC is an anti-CD25 ADC.

22. A composition, method, use, or kit according to paragraph 21, wherein the anti-CD25 ADC is ADCX25.

23. A composition, method, use, or kit according to any previous paragraph, wherein the FTP is CD25.

24. A composition, method, use, or kit according to any previous paragraph, wherein the disorder is a proliferative disease.

25. The composition, method, use, or kit of paragraph 24, wherein the disorder is cancer.

26. The composition, method, use, or kit according any previous paragraph, wherein the individual has, or has been has been determined to have, a disorder characterised by the presence of a neoplasm comprising both CD25+ve and CD25−ve cells.

27. The composition, method, use, or kit according any previous paragraph, wherein the individual has, or has been has been determined to have, a disorder characterised by the presence of a neoplasm comprising, or composed of, CD25−ve neoplastic cells.

28. The composition, method, use, or kit according to either of paragraphs 26 or 27, wherein the neoplasm is all or part of a solid tumour.

29. The composition, method, use, or kit of any previous paragraph, wherein the disorder is selected from the group comprising:
Hodgkin's and non-Hodgkin's Lymphoma, including diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL);
leukemias such as Hairy cell leukemia (HCL), Hairy cell leukemia variant (HCL-v), Acute Myeloid Leukaemia (AML), and Acute Lymphoblastic Leukaemia (ALL) such as Philadelphia chromosome-positive ALL (Ph+ALL) or Philadelphia chromosome-negative ALL (Ph−ALL);

pancreatic cancer, breast cancer, colorectal cancer, gastric and oesophageal cancer, leukemia and lymphoma, melanoma, non-small cell lung cancer, ovarian cancer, hepatocellular carcinoma, renal cell carcinoma, and head and neck cancer.

30. A composition, method, use, or kit according to any one of the preceding paragraphs, wherein the secondary agent is a Bruton's Tyrosine Kinase inhibitor (BTKi).

31. A composition, method, use, or kit according to paragraph 30, wherein the Bruton's Tyrosine Kinase inhibitor (BTKi) is selected from Ibrutinib (Imbruvica), Acalabrutinib/ACP-196, ONO/GS-4059, Spebrutinib/AVL-292/CC-292, HM71224 (Poseltinib) and BGB-3111 (Zanubrutinib).

32. A composition, method, use, or kit according to any one of paragraphs 1 to 29, wherein the secondary agent is a PD1 antagonist.

33. A composition, method, use, or kit according to paragraph 32, wherein the PD1 antagonist is selected from pembrolizumab, nivolumab, MEDI0680, PDR001 (spartalizumab), Camrelizumab, AUNP12, Pidilizumab Cemiplimab (REGN-2810), AMP-224, BGB-A317 (Tisleizumab), and BGB-108.

34. A composition, method, use, or kit according to any one of paragraphs 1 to 29, wherein the secondary agent is a PD-L1 antagonist.

35. A composition, method, use, or kit according to paragraph 34, wherein the PD-L1 antagonist is selected from atezolizumab (Tecentriq), BMS-936559/MDX-1105, durvalumab/MED14736, and MSB0010718C (Avelumab).

36. A composition, method, use, or kit according to any one of paragraphs 1 to 29, wherein the secondary agent is a GITR (glucocorticoid-Induced TNFR-Related protein) agonist.

37. A composition, method, use, or kit according to paragraph 36, wherein the GITR (glucocorticoid-Induced TNFR-Related protein) agonist is selected from MEDI1873, TRX518, GWN323, MK-1248, MK 4166, BMS-986156 and INCAGN1876.

38. A composition, method, use, or kit according to any one of paragraphs 1 to 29, wherein the secondary agent is a OX40 agonist.

39. A composition, method, use, or kit according to paragraph 38, wherein the OX40 agonist is selected from MEDI0562, MED16383, MOXR0916, RG7888, OX40mAb24, INCAGN1949, GSK3174998, and PF-04518600.

40. A composition, method, use, or kit according to any one of paragraphs 1 to 29, wherein the secondary agent is a CTLA-4 antagonist.

41. A composition, method, use, or kit according to paragraph 40, wherein the CTLA-4 antagonist is selected from ipilimumab and Tremelimumab.

42. A composition, method, use, or kit according to any one of paragraphs 1 to 29, wherein the secondary agent is Fludarabine or Cytarabine.

43. A composition, method, use, or kit according to any one of paragraphs 1 to 29, wherein the secondary agent is a hypomethylating agent.

44. A composition, method, use, or kit according to paragraph 43, wherein the hypomethylating agent is selected from 5-azacytidine (azacitidine) and 5-aza-2'-deoxycytidine (decitabine).

A composition, method, use, or kit according to any previous paragraph, wherein the STP is BTK, PD1, PDL1, GITR, OX40, or CTLA.

46. A composition, method, use, or kit according to paragraph 33, wherein the STP is PD-L1.

EXAMPLES

In the following examples:
the FTP is preferably CD25.
Cell lines expressing CD25 suitable for use in the examples include L540, Karpas299, Sudhl1, HDLM-2 cells.

Disease A—Diffuse Large B-cell Lymphoma/DLBC is an aggressive type of non-Hodgkin lymphoma that develops from the B-cells in the lymphatic system. It constitutes the largest subgroup of non-Hodgkin lymphoma.

Disease B—Mantle Cell Lymphoma/MCL is a rare B-cell NHL that most often affects men over the age of 60. The disease may be aggressive (fast growing) but it can also behave in a more indolent (slow growing) fashion in some patients. MCL comprises about five percent of all NHLs.

Disease C—Follicular lymphoma/FL is a fairly indolent type of NHL with long survival time but for which it is very difficult to achieve a cure; it can also transform into more aggressive forms of lymphoma.

Example 1

To show that a PBD-ADC can induce ICD and therefore can be a suitable combination agent with immune-oncology (IO) drugs, cell lines expressing a first target protein (FTP), will be incubated for 0, 6, 24 and 48 hours with etoposide (negative control) and oxaliplatin (positive control), 1 pg/mL ADC, 1 pg/mL anti-FTP (the antibody in ADC) and 1 pg/mL of B12-SG3249 (a non-binding control ADC with the same PBD payload as ADC).

After Incubation, the amount of AnnexinV−/P1+ (early apoptotic cells) will be measured by Flow cytometry together with the upregulation of surface calreticulin and HSP-70. ER stress will be measured by Northern blot analyses of IRE1 phosphorylation, ATF4 and JNK phosphorylation.

Example 2

In a separate experiment, cell lines expressing FTPs will be incubated for 0, 6, 24 and 48 hours with etoposide (negative control) and oxaliplatin (positive control), 1 μg/mL ADC (ADC targeting FTP with a PBD dimer warhead), 1 pg/mL anti-FTP (the antibody in ADC) and 1 μg/mL of B12-SG3249 (a non-binding control ADC with the same PBD payload as ADC).

After incubation, the cells are washed, and fed to human Dendritic cells (DCs) for an additional 24 h. Activation of the DCs is subsequently measured by increased surface expression of CD86 on the DC population (as determined by Flow cytometry) and by measuring DC mediated release of IL-8 and MIP2.

Example 3

The purpose of this study is to preliminarily assess the safety, tolerability, pharmacological and clinical activity of this combination The following cancer types have been chosen for study: Disease A, Disease B, and Disease C Evidence for efficacy as single agents exists for both drugs:
ADC (see, for example, WO2014/057119, WO2016/083468, and WO2016/166341)

Secondary agent (see KS Peggs et al. 2009, Clinical and Experimental Immunology, 157: 9-19 [doi:10.1111/j.1365-2249.2009.03912.x])

This primary purpose of this study is to explore whether these agents can be safely combined, and if so, will identify the dose(s) and regimens appropriate for further study. The study will also assess whether each combination induces pharmacologic changes in tumor that would suggest potential clinical benefit.

In addition, it will provide preliminary evidence that a combination may increase the response rate and durability of response compared with published data for treatment with single agent ADC or secondary agent.

Each disease group may include a subset of patients previously treated with the secondary agent to explore whether combination therapy might overcome resistance to secondary agent therapy. For each disease, it is not intended to apply specific molecular selection as the data available at present generally do not support excluding patients on the basis of approved molecular diagnostic tests.

Rationale for ADC Starting Dose

The RDE for already established for ADC (in ug/kg administered every three weeks) will be used for all patients in this study. To ensure patient safety, a starting dose below the RDE will be used; the starting dose level will be one where patient benefit could still be demonstrated in study ADC1, suggesting that patients enrolled at such dose level will gain at least some benefit by taking part.

Rationale for Secondary Agent Starting Dose

The RDE for already established for the secondary agent (in ug/kg administered every three weeks) will be used for all patients in this study. To ensure patient safety, a starting dose below the RDE will be used; the starting dose level will be one where patient benefit could still be demonstrated in study SA1, suggesting that patients enrolled at such dose level will gain at least some benefit by taking part.

Objectives and Related Endpoints

Study Design

This phase Ib, multi-center, open-label study to characterize the safety, tolerability, pharmacokinetics (PK), pharmacodynamics (PD) and antitumor activity of the ADC in combination with the secondary agent, in patients with disease A, disease B, and disease C.

The study is comprised of a dose escalation part followed by a dose expansion part.

Figure 11:
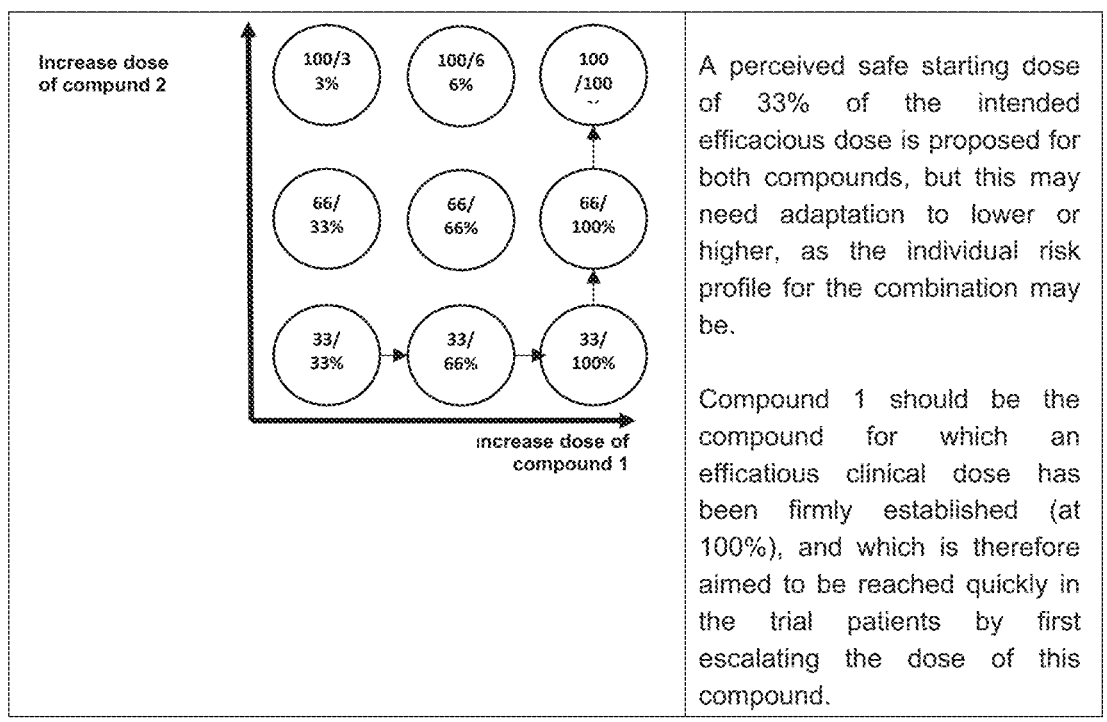
FIG. 11. Diagram of dose escalation for both ADC and the secondary agent.

Dose escalation will start with reduced starting doses (compared to their respective recommended phase 2 or licensed dose levels), for both ADC and the secondary agent, to guarantee patient safety. Starting doses will be 33% (or 50%) of the RDE for each compound. Subsequently, doses will be first escalated for the secondary agent until the RDE or licensed dose has been reached, or a lower dose if necessary for tolerability reasons. Then, the dose for ADC will be escalated, until the RDE for combination treatment is reached. This is visualized in FIG. 11.

If the dose combination is determined to be safe, it may be tested in additional patients to confirm the safety and tolerability at that dose level. Further tailoring of the dose of each compound may be conducted, and/or the regimen may be modified.

The dose escalation of the combination will be guided by a Bayesian Logistic Regression Model (BLRM) based on any Dose Limiting Toxicities (DLTs) observed in the first (or first two, TBC) cycles of therapy. Use of a BLRM is a well-established method to estimate the maximum tolerated dose (MTD)/recommended dose for expansion (ROE) in cancer patients. The adaptive BLRM will be guided by the Escalation With Overdose Control (EWOC) principle to control the risk of DLT in future patients on the study. The use of Bayesian response adaptive models for small datasets has been accepted by FDA and EMEA ("Guideline on clinical trials in small populations", Feb. 1, 2007) and endorsed by numerous publications (Babb et al. 1998, Neuenschwander et at 2008).

| Objective | Endpoint |
| --- | --- |
| Primary Objective | |
| To characterize the safety and tolerability of ADC in combination with the secondary agent, and to identify the recommended dose and schedules for future studies | Frequency and severity of treatment-emergent AEs and SAEs Changes between baseline and post-baseline laboratory parameters and vital signs Incidence of dose limiting toxicities (DLTs) during the first cycle of treatment (dose escalation only) Frequency of dose interruptions and dose reductions |
| Secondary Objectives | ORR, DOR, PFS, OS |
| To evaluate the clinical activity of the combination of ADC with the secondary agent | AUC and Cmax for each compound Anti-Drug-Antibodies (ADAs) before, during and after treatment with ADC |
| To characterize the pharmacokinetic (PK) profile of each of the two compounds ADC and the secondary agent | |
| Evidence for immunogenicity and ADAs to ADC | |
| Exploratory Objectives | Correlation coefficients between AUC and/or Cmax of each compound or a compound measure and any of the safety or efficacy variables Immunohistochemistry of pre- and on-treatment tumor biopsies, Measurements (e.g. via ELISA) of immunologically relevant cytokines in plasma or serum; staining levels for activation markers of circulating immune cells (e.g. FACS) |
| To examine potential correlation of PK profiles with safety/tolerability and efficacy | |
| To characterize changes in the immune infiltrate in tumors | |
| To characterize changes in circulating levels of cytokines in plasma and markers of activation in circulating immune cells | |

The decisions on new dose combinations are made by the Investigators and sponsor study personnel in a dose escalation safety call (DESC) based upon the review of patient tolerability and safety information (including the BLRM summaries of DLT risk, if applicable) along with PK, PD and preliminary activity information available at the time of the decision.

Once the MTD(s)/RDE is determined for the combination, the expansion part of the study may be initiated to further assess the safety, tolerability and preliminary efficacy.

For combinations with IO, changes in the immune infiltrate in tumors will also be characterized following combination treatment in the target disease indications.

Given the available prior clinical experience with the agents in this study, it is expected that in most cases a combination dose can be identified without testing a large number of dose levels or schedules. To assess the pharmacodynamic activity of the combinations, patients will be asked to undergo a tumor biopsy at baseline and again after approximately two cycles of therapy.

R For IO combo: The extent of the change in tumor infiltration by immune cells including lymphocytes and macrophages will contribute to a decision on any potential benefit.

Dose Escalation Part

During the dose escalation part of the study, patients will be treated with a fixed dose of ADC administered i.v., and increasing doses of the secondary agent until the RDE for the secondary agent has been reached. Subsequently, doses of ADC are increased (in different cohorts) while the dose for the secondary agent is kept constant.

Two to approximately 3 or 4 patients with disease A, disease B or disease C will be treated in each escalation cohort until the determination of MTD(s)/RDE(s) is determined.

There will be a 24-hour observation before enrolling the second patient at Dose Level 1. The DLT observation period at each dose level is either 1 cycle (3 weeks) or 2 cycles (6 weeks) as mandated by the appropriate authorities for IO therapies, after which it will be determined whether to escalate to the next dose level, stay at the current dose level, or de-escalate to the previous dose level for the next cohort. There will be no de-escalation from Dose Level 1. Intrapatient dose escalation is not permitted.

Dose escalation is not permitted unless 2 or more patients have complete DLT information through the first cycle in any given dose level. Dose escalation will be determined by using a mCRM with a target DLT rate of 30% and an equivalence interval of 20% to 35%, and with dose escalation-with-overdose-control (EWOC) and no dose skipping.

Patients will be assigned to a cohort that is actively enrolling. Dose escalation will be performed in each combination following the completion of one cycle of treatment. Safety assessments including adverse events (AEs) and laboratory values will be closely monitored for all enrolled patients in order to identify any DLTs. A single MTD/RDE will be defined; a disease-specific MTD/RDE will not be established.

The mCRM will be implemented for DE under the oversight of a Dose Escalation Steering Committee (DESC). The DESC will confirm each escalating dose level after reviewing all available safety data. PK data from patients in that dose level and prior dose levels may also inform decision making. The DESC may halt dose escalation prior to determining the MTD based on emerging PK, PD, toxicity or response data.

Additional patients may be included at any dose level to further assess the safety and tolerability if at least 1 patient in the study has achieved a partial response or better, or if further evaluation of PK or PD data is deemed necessary by the DESC to determine the RDE.

Dose Escalation will be stopped after 3 cohorts (or at least 6 patients) are consecutively assigned to the same dose level. If the MTD is not reached, the recommended dose for expansion (RDE) will be determined. Prior to the determination of the MTD/RDE a minimum of 6 patients must have been treated with the combination.

It is intended that paired tumor biopsies will be obtained from patients during dose escalation. Analysis of these biopsies will contribute to a better understanding of the relationship between the dose and the pharmacodynamic activity of the combination.

Safety Oversight by the Dose Escalation Steering Committee

A DESC comprised of ADC Therapeutics and the investigators will review patient safety on an ongoing basis during the DE to determine if the dose escalation schedule prescribed by the mCRM warrants modification. In addition to safety observations, PK and/or PD data may also inform decision making. Intermediate doses may be assigned after agreement between ADC Therapeutics and investigators. The DESC may continue to provide oversight during Part 2. No formal Data Safety Monitoring Board (DSMB) will be used.

Dose Expansion Part

Once the MTD/RDE has been declared, dose expansion part may begin. The main objective of the expansion part is to further assess the safety and tolerability of the study treatment at the MTD/RDE and to gain a preliminary understanding of the efficacy of the combination compared to historical single agent efficacy data.

An important exploratory objective is to assess changes in the immune infiltrate in tumor in response to treatment. This will be assessed in paired tumor biopsies collected from patients, with a minimum of ten evaluable biopsy pairs (biopsy specimens must contain sufficient tumor for analysis) in patients treated at the MTD/RDE. If this is not feasible, collection of these biopsies may be stopped. A minimum of 10 to 20 patients are planned to be treated in each investigational arm, Several different investigational arms will open, one per disease. A total of nine investigational arms may be run in the dose expansion. Should enrollment for any of these groups not be feasible, then enrollment to that group may be closed before the 10 to 20 patients target is met.

In each treatment group a maximum of approximately six patients who have received and progressed on prior single administration (i.e. not in combination) secondary agent therapy will be allowed to be treated. This number may be increased if a combination shows promise of overcoming resistance to prior treatment with single administration secondary agent.

Patient Population

The study will be conducted in adult patients with advanced Disease A, Disease B or Disease C as outlined above. The investigator or designee must ensure that only patients who meet all the following inclusion and none of the exclusion criteria are offered treatment in the study.

Inclusion Criteria

Patients eligible for inclusion in this study have to meet all of the following criteria:

1. Written informed consent must be obtained prior to any procedures

2. Age 18 years.
3. Patients with advanced/metastatic cancer, with measurable disease as determined by RECIST version 1.1, who have progressed despite standard therapy or are intolerant to standard therapy, or for whom no standard therapy exists. Patients must fit into one of the following groups:
   Disease A
   Disease B
   Disease C
4. ECOG Performance Status 0-1 (or 2 TBC)
5. TBC: Patient must have a site of disease amenable to biopsy, and be a candidate for tumor biopsy according to the treating institution's guidelines. Patient must be willing to undergo a new tumor biopsy at baseline, and again during therapy on this study.
6. Prior therapy with the secondary agent or related compounds (i.e. same MOA) is allowed Exclusion Criteria Patients eligible for this study must not meet any of the following criteria:
1. History of severe hypersensitivity reactions to other mAbs (OR to same backbone mAb as in ADC OR to same IO mAb if applicable)
2. Known history of positive serum human ADA to backbone of mAb as in ADC
3. Central Nervous System (CNS) disease only (if applicable)
4. Symptomatic CNS metastases or evidence of leptomeningeal disease (brain MRI or previously documented cerebrospinal fluid (CSF) cytology)
   Previously treated asymptomatic CNS metastases are permitted provided that the last treatment (systemic anticancer therapy and-or local radiotherapy) was completed >=8 weeks prior to $1^{st}$ day of dosing, except usage of low dose steroids on a taper is allowed)
   Patients with discrete dural metastases are eligible.
5. Patient having out of range laboratory values defined as:
   Serum creatinine <=1.5xULN. If serum creatinine >1.5, the creatinine clearance (calculated using Cockcroft-Gault formula, or measured) must be >60 mL/min/1.73m2 for a patient to be eligible
   Total bilirubin >1.5xULN, except for patients with Gilbert's syndrome who are excluded if total bilirubin >3.0xULN or direct bilirubin >1.5xULN
   Alanine aminotransferase (ALT)>3xULN, except for patients that have tumor involvement of the liver, who are excluded if ALT >5xULN
   Aspartate aminotransferase (AST)>3xULN, except for patients that have tumor involvement of the liver, who are excluded if AST >5xULN
   Absolute neutrophil count<1.0x10e9/L
   Platelet count<75x10e9/L
   Hemoglobin (Hgb)<8 g/dL
   Potassium, magnesium, calcium or phosphate abnormality >CTCAE grade 1 despite appropriate replacement therapy
6. Impaired cardiac function or clinically significant cardiac disease, including any of the following:
   Clinically significant and/or uncontrolled heart disease such as congestive heart failure requiring treatment (NYHA grade III or IV) or uncontrolled hypertension defined by a Systolic Blood Pressure (SBP) 160 mm Hg and/or Diastolic Blood Pressure (DBP) 100 mm Hg, with or without anti-hypertensive medication.
   QTcF >470 msec for females or >450 msec for males on screening ECG using Fridericia's correction, congenital long QT syndrome
   Acute myocardial infarction or unstable angina pectoris <3 months (months prior to study entry
   Clinically significant valvualr disease with documented compromise in cardiac function
   Symptomatic pericarditis
   History of or ongoing documented cardiomyopathy
   Left Ventricular Ejection Fraction (LVEF) <40%, as determined by echocardiogram (ECHO) or Multi gated acquisition (MUGA) scan
   History or presence of any clinically significant cardiac arrhythmias, e.g.
   ventricular, supraventricular, nodal arrhythmias, or conduction abnormality (TBC qualifier: . . . requiring a pacemaker or not controlled with medication)
   Presence of unstable atrial fibrillation (ventricular response rate >100 bpm).
      NOTE: Patients with stable atrial fibrillation can be enrolled provided they do not meet other cardiac exclusion criteria.
   Complete left bundle branch block (LBBB), bifascicular block
   Any clinically significant ST segment and/or T-wave abnormalities
7. Toxicity attributed to prior IO therapy that led to discontinuation of therapy. Adequately treated patients for drug-related skin rash or with replacement therapy for endocrinopathies are not excluded, provided these toxicities did not lead to the discontinuation of prior treatment.
8. Patients with active, known or suspected autoimmune disease. Subjects with vitiligo, type I diabetes mellitus, residual hypothyroidism due to autoimmune condition only requiring hormone replacement, psoriasis not requiring systemic treatment, or conditions not expected to recur in the absence of an external trigger are permitted to enroll, provided the trigger can be avoided.
9. Human Immunodeficiency Virus (HIV), or active Hepatitis B (HBV) or Hepatitis C (HCV) virus infection
   Testing is not mandatory to be eligible. Testing for HCV should be considered if the patient is at risk for having undiagnosed HCV (e.g. history of injection drug use).
10. Malignant disease, other than that being treated in this study. Exceptions to this exclusion include the following: malignancies that were treated curatively and have not recurred within 2 years prior to study treatment; completely resected basal cell and squamous cell skin cancers; any malignancy considered to be indolent and that has never required therapy; and completely resected carcinoma in situ of any type.
11. Systemic anti-cancer therapy within 2 weeks of the first dose of study treatment. For cytotoxic agents that have major delayed toxicity, e.g. mitomycin C and nitrosoureas, 4 weeks is indicated as washout period. For patients receiving anticancer immunotherapies such as CTLA-4 antagonists, 6 weeks is indicated as the washout period.
12. Active diarrhea CTCAE grade 2 or a medical condition associated with chronic diarrhea (such as irritable bowel syndrome, inflammatory bowel disease)
13. Presence of 2: CTCAE grade 2 toxicity (except alopecia, peripheral neuropathy and ototoxicity, which are excluded if >=CTCAE grade 3) due to prior cancer therapy.
14. Active infection requiring systemic antibiotic therapy.
15. Active ulceration of the upper GI tract or GI bleeding
16. Active bleeding diathesis or on oral anti-vitamin K medication (except low-dose warfarin and aspirin or equivalent, as long as the INR <=2.0)

17. Active autoimmune disease, motor neuropathy considered of autoimmune origin, and other CNS autoimmune disease
18. Patients requiring concomitant immunosuppressive agents or chronic treatment with corticoids except:
    replacement dose steroids in the setting of adrenal insufficiency
    topical, inhaled, nasal and ophthalmic steroids are allowed
19. Use of any live vaccines against infectious diseases (e.g. influenza, varicella, pneumococcus) within 4 weeks of initiation of study treatment (NB the use of live vaccines is not allowed through the whole duration of the study)
20. Use of hematopoietic colony-stimulating growth factors (e.g. G-CSF, GMCSF, M-CSF)<2 weeks prior start of study drug. An erythroid stimulating agent is allowed as long as it was initiated at least 2 weeks prior to the first dose of study treatment.
21. Major surgery within 2 weeks of the first dose of study treatment (NB mediastinoscopy, insertion of a central venous access device, or insertion of a feeding tube are not considered major surgery).
22. Radiotherapy within 2 weeks of the first dose of study drug, except for palliative radiotherapy to a limited field, such as for the treatment of bone pain or a focally painful tun1or mass. To allow for assessment of response to treatment, patients must have remaining measurable disease that has not been irradiated
23. Participation in an interventional, investigational study within 2 weeks of the first dose of study treatment.
24. Any medical condition that would, in the investigator's judgment, prevent the patient's participation in the clinical study due to safety concerns, compliance with clinical study procedures or interpretation of study results.
25. Sexually active males unless they use a condom during intercourse while taking drug and for 90 days after stopping study treatment and should not father a child in this period. A condom is required to be used also by vasectomized men in order to prevent delivery of the drug via seminal fluid.
26. Pregnant or lactating women, where pregnancy is defined as the state of a female after conception and until the termination of gestation, confirmed by a positive hCG laboratory test. In rare cases of an endocrine-secreting tumor, hCG levels may be above normal limits but with no pregnancy in the patient. In these cases, there should be a repeat serum hCG test (with a non-rising result) and a vaginal/pelvic ultrasound to rule out pregnancy. Upon confirmation of results and discussion with the Medical representative, these patients may enter the study.
27. Women of child-bearing potential, defined as all women physiologically capable of becoming pregnant, unless they are using highly effective methods of contraception during study treatment and for 90 days after the last any dose of study treatment. Highly effective contraception methods include:
    Total abstinence (when this is in line with the preferred and usual lifestyle of the patient. Periodic abstinence (e.g., calendar, ovulation, symptothermal, post-ovulation methods) and withdrawal are not acceptable methods of contraception
    Female sterilization (have had surgical bilateral oophorectomy with or without hysterectomy), total hysterectomy or tubal ligation at least 6 weeks before taking study treatment. In case of oophorectomy alone, only when the reproductive status of the woman has been confirmed by follow up hormone level assessment
    Male sterilization (at least 6 months prior to screening). For female patients on the study the vasectomized male partner should be the sole partner for that patient.
    Use of oral (estrogen and progesterone), injected or implanted combined hormonal methods of contraception or placement of an intrauterine device (IUD) or intrauterine system (IUS) or other forms of hormonal contraception that have comparable efficacy (failure rate <1%), for example hormone vaginal ring or transdermal hormone contraception.
        In case of use of oral contraception, women should have been stable on the same pill for a minimum of 3 months before taking study treatment.
        Women are considered post-menopausal and not of child bearing potential if they have had 12 months of natural (spontaneous) amenorrhea with an appropriate clinical profile (e.g. age appropriate, history of vasomotor symptoms) or have had surgical bilateral oophorectomy (with or without hysterectomy) or tubal ligation at least 6 weeks ago. In the case of oophorectomy alone, only when the reproductive status of the woman has been confirmed by follow up hormone level assessment is she considered not of child bearing potential.

Dose-Limiting Toxicities and Dose Modification Guidelines

A dose-limiting toxicity (DLT) is defined as any of the following events thought to be at least possibly related to ADC per investigator judgment that occurs during the 21-day DLT evaluation period. Toxicity that is clearly and directly related to the primary disease or to another etiology is excluded from this definition.

DLT Definitions

A hematologic DLT is defined as:

Grade 3 or 4 febrile neutropenia or neutropenic infection

Grade 4 neutropenia lasting >7 days

Grade 4 thrombocytopenia

Grade 3 thrombocytopenia with clinically significant bleeding, or Grade 3 thrombocytopenia requiring a platelet transfusion Grade 3 anemia that requires transfusion Grade 4 anemia A non-hematologic DLT is defined as:

Grade 4 non-hematologic toxicity

Grade 3 non-hematologic toxicity lasting >3 days despite optimal supportive care or medical intervention A case of Hy's law (AST and/or ALT>3xULN and bilirubin >2xULN, and without initial findings of cholestasis (serum alkaline phosphatase (ALP) activity <2xULN) and no other reason that could explain the combination of increased transaminases and serum total bilirubin, such as viral hepatitis A, B, or C, preexisting or acute liver disease, or another drug capable of causing the observed injury)

Grade 3 or higher hypersensitivity/infusion-related reaction (regardless of premedication). A grade 3 hypersensitivity/infusion-related reaction that resolves within 8 hours after onset with appropriate clinical management does not qualify as a DLT.

LVEF decrease to <40% or >20% decrease from baseline

Grade 4 tumor lysis syndrome (Grade 3 TLS will not constitute DLT unless it leads to irreversible end-organ damage)

The following conditions are not considered non-hematologic DLT:
- Grade 3 fatigue for 5 7 days
- Grade 3 diarrhea, nausea, or vomiting in the absence of premedication that responds to therapy and improves by at least 1 grade within 3 days for Grade 3 events or to 5 Grade 1 within 7 days.
- AST or ALT elevation 5×ULN but 5 8×ULN, without concurrent elevation in bilirubin, that downgrades to 5 Grade 2 within 5 days after onset.
- Grade 3 serum lipase or serum amylase for 5 7 days if without clinical signs or symptoms of pancreatitis Patients who experience a DLT that resolves or stabilizes with appropriate medical management may continue treatment at the discretion of the investigator in consultation with the sponsor.

Dose Modifications

Guidelines for management of specific toxicities are detailed in the table below. For management of events not specified in the tables, the following may serve as a guidance to investigators:

| AE Grade | ADC Management Guideline |
|---|---|
| 1 | No dose adjustment is required. |
| 2 | First occurrence: Consider holding one or both drugs until improvement to ≤ Grade 1 or baseline. Up to 1 dose of one or both drugs may be skipped to permit improvement. If improvement to ≤ Grade 1 or baseline occurs within 21 days from the last scheduled (but missed) dose of one or both drugs, continue one or both drugs at the original assigned dose level in subsequent treatment cycles. If improvement to ≤ Grade 1 or baseline does not occur within 21 days from the last scheduled (but missed) dose, permanently discontinue one or both drugs. Second occurrence: Hold one or both drugs until improvement to ≤ Grade 1 or baseline. Up to 1 dose of one or both drugs may be skipped to permit resolution. If improvement to ≤ Grade 1 or baseline occurs within 21 days from the last scheduled (but missed) dose, continue one or both drugs at 1 dose level below the original assigned dose in subsequent treatment cycles. If improvement to ≤ Grade 1 or baseline does not occur within 21 days from the last scheduled (but missed) dose, permanently discontinue one or both drugs. Third occurrence: Permanently discontinue one or both drugs. |
| 3 | First occurrence: Hold one or both drugs until improvement to ≤ Grade 1 or baseline. Up to 1 dose of one or both drugs may be skipped to permit improvement, then continue at 1 dose level below the original assigned dose in subsequent treatment cycles. Second occurrence: Permanently discontinue one or both drugs |
| 4 | Permanently discontinue one or both drugs. |

Example 4

In Vivo Efficacy Study of Surrogate-301 in an Immuno-Competent Syngeneic Mouse Model Using Mouse Colon Cancer MC38 Cells Introduction MC38 is a mouse colon cancer-derived model used preclinically in immunotherapy-type studies which is known to have infiltration of Treg and Teff cells.

In Arce Vargas et al., 2017, Immunity 46, 1-10, Apr. 18, 2017 (http://dx.doi.org/10.1016/j.immuni.2017.03.013) selective depletion of tumor infiltrating Treg cells in the MC38 model was shown using an Fc enhanced version of PC61, a rat antibody directed against mouse CD25 and synergy with PD1 was described. The wild-type PC61 was conjugated to the PBD dimer SG3249 and designated as Surrogate-ADCx25. The efficacy of Surrogate-ADCx25 was studied as monotherapy or in combination with anti-PD1 (Anti-PD1, clone RPM1-14, BioXcell cat #BE0146) in the MC38 syngeneic mouse model.

Study Design

Surrogate-ADCx25 was administered as single dose (0.1, 0.5 and 1 mg/kg) on day 1 either alone or in combination with anti-PD1 antibody (given at standard dosing regime, i.e. 5 mg/kg at day 2, 5 and 8). As a control, Isotype Control ADC (B12-SG3249) was administered as single dose (1 mg/kg) on day 1 either alone or in combination with anti-PD1 antibody (given at standard dosing regime), while anti-PD1 antibody was administered alone at standard dosing regimen.

Results

Figure 3:
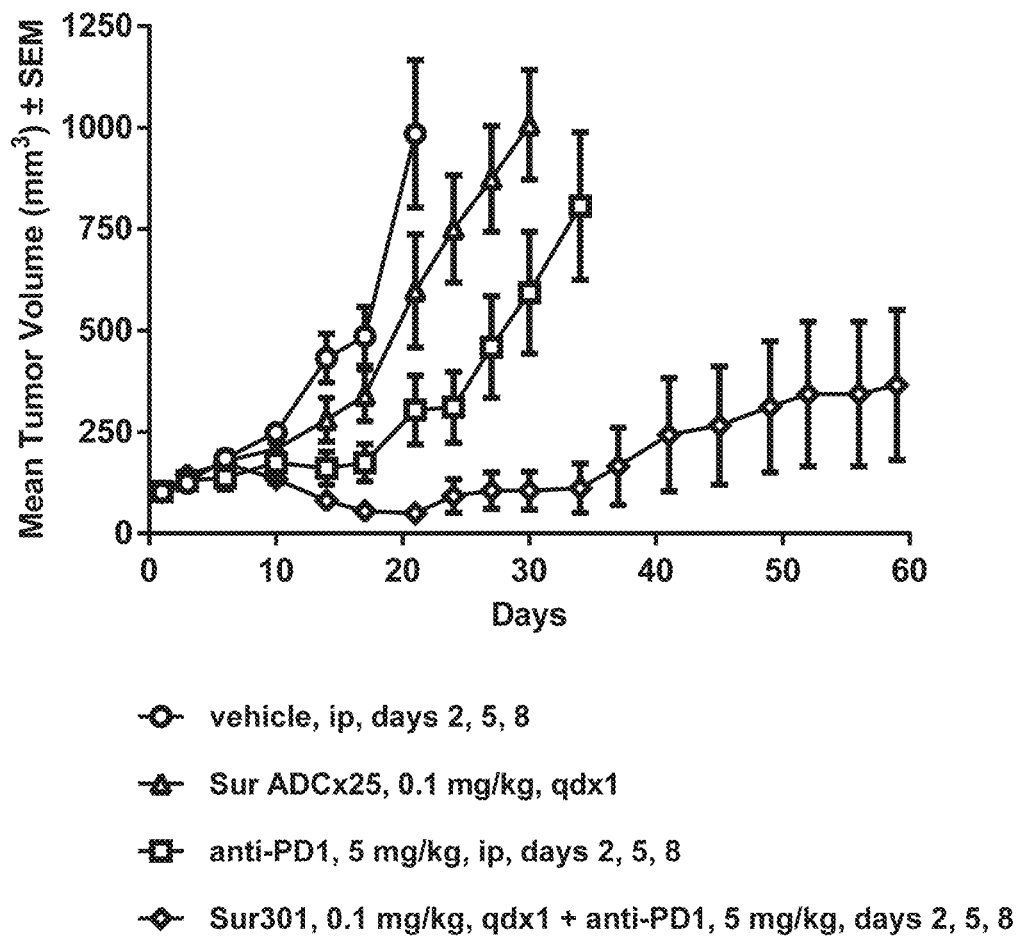
FIG. 3. In vivo tumour volume showing synergy between low-dose surrogate ADCx25 and anti-PD1 treatment (as per Example 4)

Surrogate-ADCx25 had strong and dose-dependent antitumor activity per se in the MC38 syngeneic model. The isotype control ADC had significant lower activity than surrogate-ADCx25 at 1 mg/kg. (FIG. 2). A strong synergy was observed when combining a low single dose of surrogate-ADCx25 with anti-PD1 antibody (FIG. 3). High efficacy of higher doses of surrogate-ADCx25 in the present model prevented assessment of synergy at higher doses.

Example 5

To show that ADCx25 works synergistically with Cytarabine, a panel of CD25(+) cell lines including, but not limited to Karpas and SUDHL1, were co-treated with a range of concentration of both ADCx25 and Cytarabine. As negative controls, the same panel of cell lines was co-treated with a range of concentrations of Cytarabine and a non-targeted control ADC or with a range of concentration of ADC and vehicle.

After incubation, two parameters were measured: the amount of surface CD25 (as determined by flow cytometry) and the in vitro cytotoxicity of the combinations (as determined by CellTiter-Glo® or MTS assays). Cytotoxic synergy was calculated by transforming the cell viability data into fraction affected, and calculating the combination index (Table 1) using the CalcuSyn analysis program.

TABLE 1

| CI value | | Synergism/antagonism |
|---|---|---|
| <0.1 | +++++ | Very strong synergism |
| 0.1-0.3 | ++++ | Strong synergism |
| 0.3-0.7 | +++ | Synergism |
| 0.7-0.85 | ++ | Moderate synergism |
| 0.85-0.9 | + | Slight synergism |
| 0.9-1.1 | | Nearly additive |
| 1.1-1.2 | − | Slight antagonism |
| 1.2-1.45 | −− | Moderate antagonism |
| 1.45-3.3 | −−− | Antagonism |
| 3.3-10 | −−−− | Strong antagonism |
| >10 | −−−−− | Very strong antagonism |

FIG. 4 shows the in vitro cytotoxicity data against the Karpas299 cell line of Cytarabine alone (left graph) or in combination with ADCx25 (right graph). Calcusyn analysis (Table 2) showed there is clear synergy, especially at higher concentrations of the ADC.

TABLE 2

CI for experimental values

| ADCx25 (ng/ml) | Decitabine (nm) | Fa | CI |
|---|---|---|---|
| 0.1 | 30 | 0.016 | 2.846 |
| 0.4 | 30 | 0.019 | 4.966 |
| 1.2 | 30 | 0.156 | 0.928 |
| 3.7 | 30 | 0.358 | 0.747 |
| 11.1 | 30 | 0.662 | 0.522 |
| 33.3 | 30 | 0.821 | 0.589 |
| 100 | 30 | 0.836 | 1.563 |
| 0.1 | 100 | 0.145 | 0.505 |
| 0.4 | 100 | 0.172 | 0.580 |
| 1.2 | 100 | 0.313 | 0.433 |
| 3.7 | 100 | 0.437 | 0.568 |
| 11.1 | 100 | 0.669 | 0.522 |
| 33.3 | 100 | 0.823 | 0.587 |
| 100 | 100 | 0.832 | 1.622 |

FIG. 5 shows the in vitro cytotox data against KG-1 cell line of cytarabine alone (left graph) or in combination with ADCx25 (right graph). Calcusyn analysis (Table 3) showed there is clear synergy, especially with 10 nM cytarabine.

TABLE 3

CI for experimental values

| ADCx25 (ng/ml) | Decitabine (nm) | Fa | CI |
|---|---|---|---|
| 0.005 | 1 | 0.078 | 1.296 |
| 0.05 | 1 | 0.022 | 15.593 |
| 0.5 | 1 | 0.120 | 3.690 |
| 5 | 1 | 0.393 | 1.596 |
| 50 | 1 | 0.883 | 0.136 |
| 0.05 | 10 | 0.044 | 27.002 |
| 0.5 | 10 | 0.205 | 4.241 |
| 5 | 10 | 0.597 | 0.747 |
| 50 | 10 | 0.906 | 0.131 |

KG-1 express low levels of CD25. FIG. 6 shows that the synergy of Cytarabine and ADCx25 against the KG-1 cell line may be explained by an increase in surface CD25, as incubating CD25(+) KG-1 cells with Cytarabine resulted in a two-fold increase in surface CD25 levels (as determined by FACS analysis). No increase in surface CD25 was observed when the Karpas299 cell line, which is high in CD25, was incubated with Cytarabine.

Example 6

To show that ADCx25 works synergistically with Decitabine, a panel of CD25(+) cell lines were co-treated with a range of concentration of both ADCx25 and Decitabine. As negative controls, the same panel of cell lines were co-treated with a range of concentrations of Decitabine or with a range of concentration of ADCx25 and vehicle.

After incubation, two parameters were measured: the amount of surface CD25 (as determined by flow cytometry) and the in vitro cytotoxicity of the combinations (as determined by MTS assays). To determine the cytotoxicity, Cell viability is measured by adding MTS per well and incubating for 4 hours at 37 C. Percentage cell viability is calculated compared to the untreated control. Cytotoxic synergy is calculated by transforming the cell viability data into fraction affected, and calculating the combination index (Table 3) using the CalcuSyn analysis program.

TABLE 3

| CI value | | Synergism/antagonism |
|---|---|---|
| <0.1 | +++++ | Very strong synergism |
| 0.1-0.3 | ++++ | Strong synergism |
| 0.3-0.7 | +++ | Synergism |
| 0.7-0.85 | ++ | Moderate synergism |
| 0.85-0.9 | + | Slight synergism |
| 0.9-1.1 | | Nearly additive |
| 1.1-1.2 | − | Slight antagonism |
| 1.2-1.45 | −− | Moderate antagonism |
| 1.45-3.3 | −−− | Antagonism |
| 3.3-10 | −−−− | Strong antagonism |
| >10 | −−−−− | Very strong antagonism |

Figure 7:
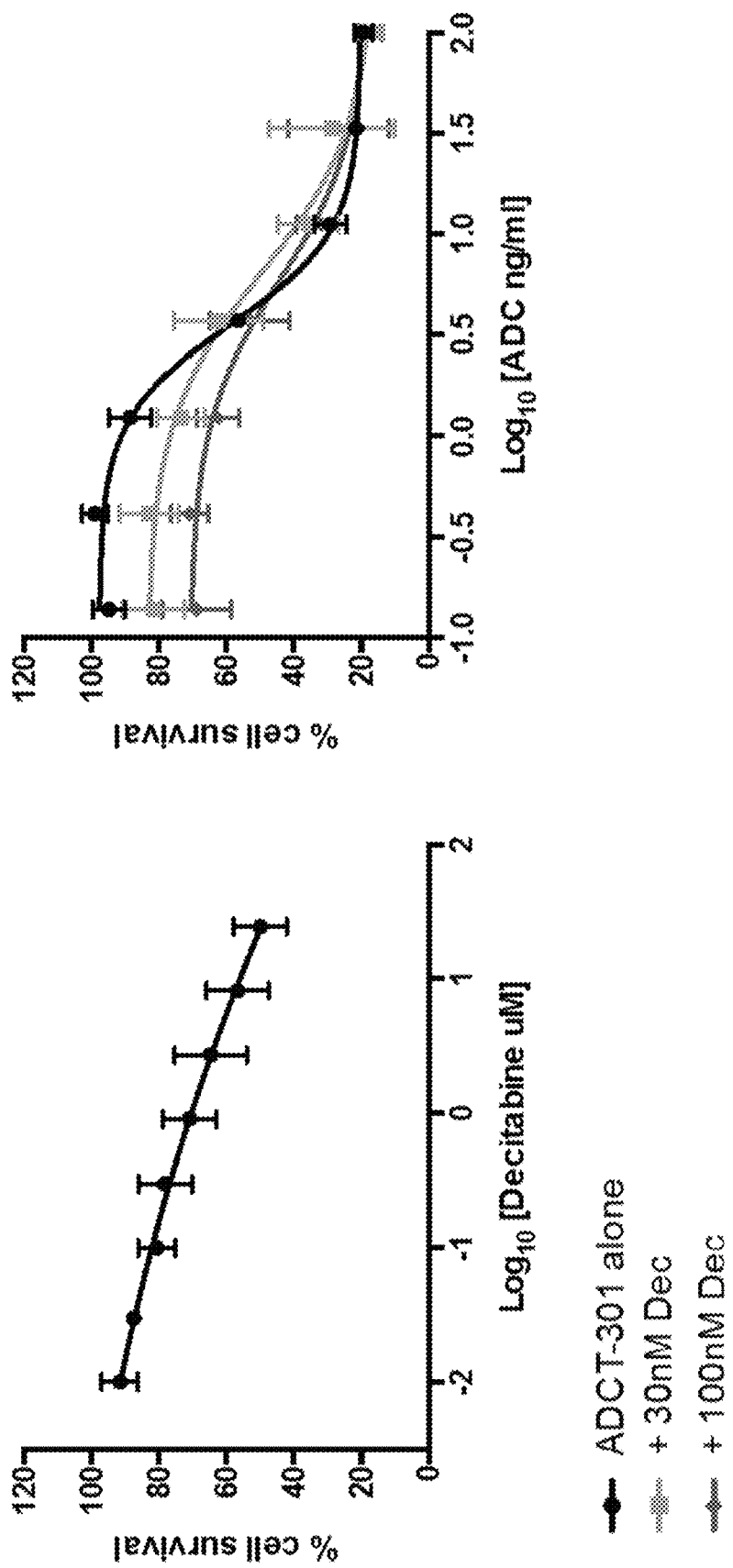
FIG. 7. In vitro cytotoxicity of decitabine alone (left graph) or ADCx25 in combination with decitabine (right graph).
Figure 8:
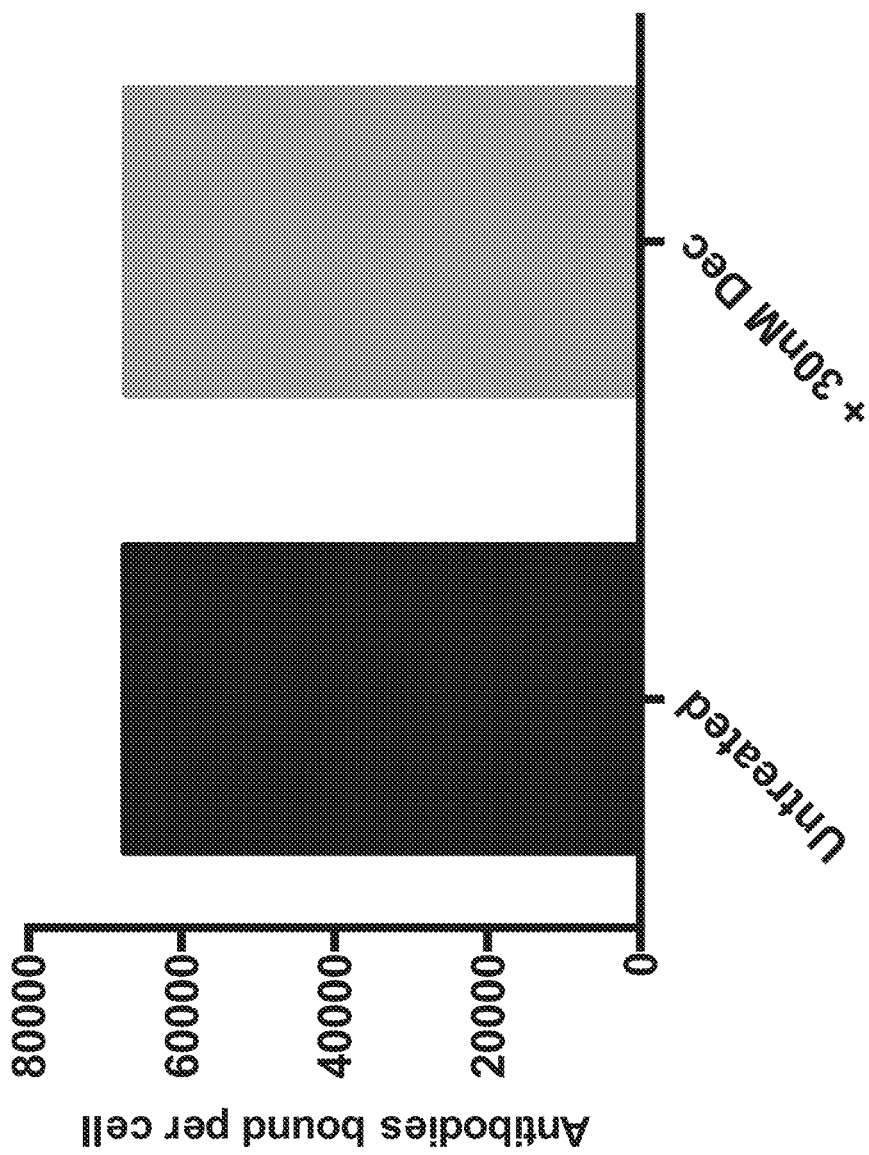
FIG. 8. Cell surface levels of CD25 on cells (untreated or after incubation with 30 mM decitabine)

FIG. 7 shows the in vitro cytotox data against the Karpas299 cell line of decitabine alone or in combination with ADCx25 Calcusyn analysis. Table 4 shows there is clear synergy, especially at lower concentrations of the ADC. There was no difference on the amount of CD25 on the cells in the presence of 30 mM decitabine (see FIG. 8).

TABLE 4

CI for experimental values

| ADCx25 (ng/ml) | Decitabine (nm) | Fa | CI |
|---|---|---|---|
| 0.1 | 30 | 0.183 | 0.265 |
| 0.4 | 30 | 0.171 | 0.514 |
| 1.2 | 30 | 0.264 | 0.426 |
| 3.7 | 30 | 0.377 | 0.658 |
| 11.1 | 30 | 0.645 | 0.559 |
| 33.3 | 30 | 0.712 | 1.182 |
| 100 | 30 | 0.836 | 1.560 |
| 0.1 | 100 | 0.311 | 0.095 |
| 0.4 | 100 | 0.290 | 0.207 |
| 1.2 | 100 | 0.374 | 0.2472 |
| 3.7 | 100 | 0.468 | 0.433 |
| 11.1 | 100 | 0.682 | 0.463 |
| 33.3 | 100 | 0.731 | 1.062 |
| 100 | 100 | 0.824 | 1.718 |

Example 7

To evaluate the cytotoxic synergy between ADCx25 and the secondary agents Cytarabine and Decitabine in the CD25 high expressing cell line Karpas299, $1 \times 10^4$ Karpas 299 cells were seeded in 50 µl, in each well of a 96 well flat bottom plate with either 30 or 100 nM Cytarabine/Decitabine. After 24 hours a serial dilution series of ADCx25 was prepared in a separate plate, and 50 µl of ADC was added to the Karpas 299 cells and incubated for 96 hours, along with untreated controls, to allow for at least 3 cell doublings.

After 120 hours 20 µl MTS was added to each well, and incubated for 2-3 hours under normal cell culture conditions. The OD was measured at 492 nm using a plate reader, and % growth calculated compared to the untreated control cells.

Growth curves were plotted using GraphPad Prism using the sigmoidal, 4PL, X is log (concentration) equation. IC50 values (dose of drug that inhibits growth by 50%) were determined. Percentage cell survival was converted into fraction affected (Fa) and the combination index (CI) for each dose calculated using CalcuSyn v2.11.

Figure 9:
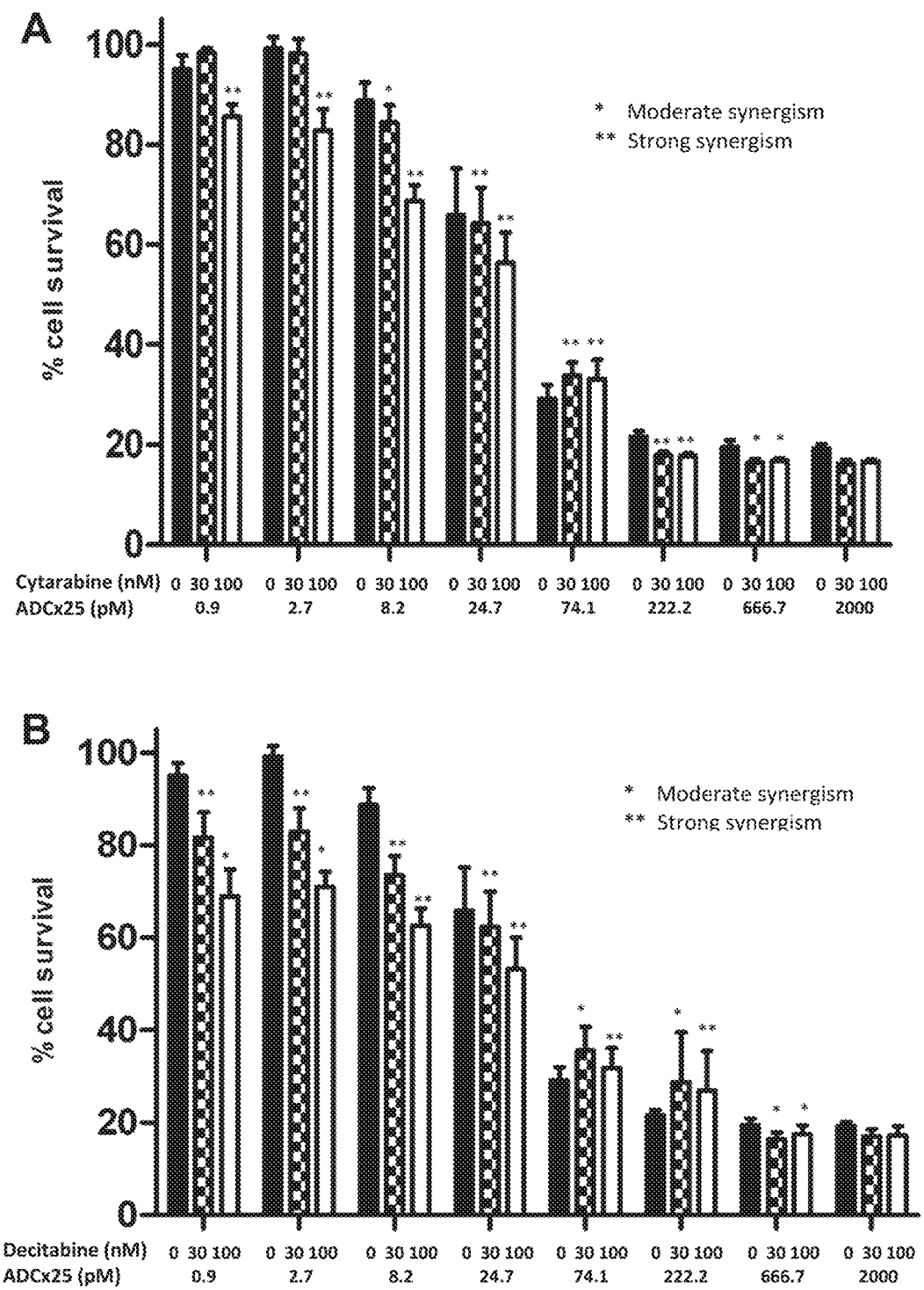
FIG. 9. In vitro cytotoxicity against Karpas299 cells of ADCx25 in combination with Cytarabine (9A) or decitabine (9B).

Results are shown in FIGS. 9A (Cytarabine) and 9B (Decitabine), where * indicates moderate synergism and ** strong synergism as determined by CalcuSyn.

Example 8

To evaluate the cytotoxic synergy between ADCx25 and the secondary agents Cytarabine and Decitabine in the CD25 low expressing cell line KG-1, the protocol of Example 7 was followed using KG-1 cell in place of the Karpas299 cells of Example 7.

Figure 10:
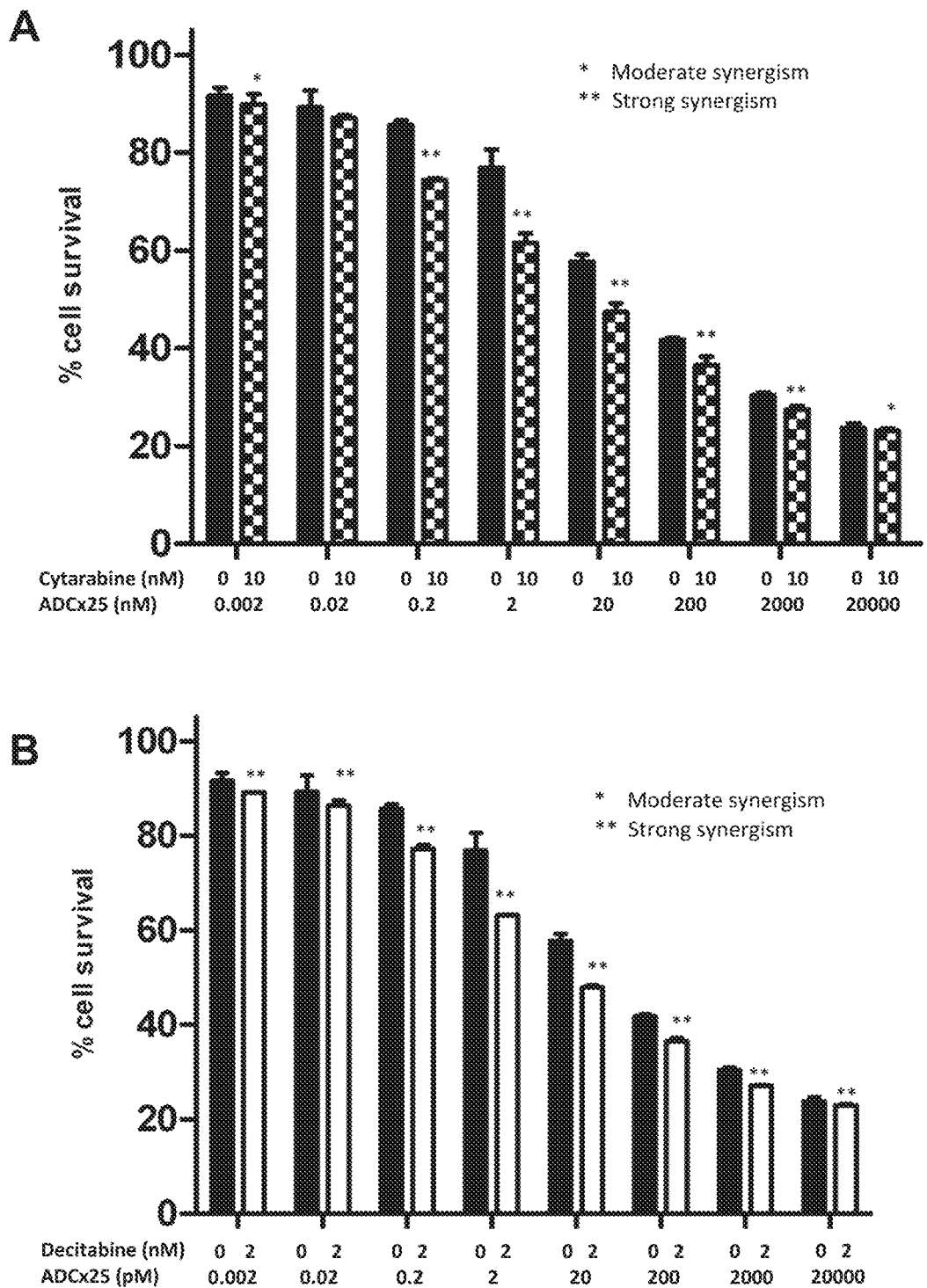
FIG. 10. In vitro cytotoxicity against KG-1 cells of ADCx25 in combination with Cytarabine (10A) or decitabine (10B).

Results are shown in FIGS. 10A (Cytarabine) and 10B (Decitabine), where * indicates moderate synergism and ** strong synergism as determined by CalcuSyn.

Example 9

Measuring the Expression Level of CD25—mRNA

Karpas-299, EOL-1 or KG-1 cells were incubated with 30 nM Cytarabine for 24 hours before mRNA was isolated and reverse-transcribed. cDNA was probed for IL2Ralpha (CD25) by TaqMan qRT-PCR. Mean fold change in expression compared to the untreated control was calculated using the ddCT method using the reference gene abl-1. A time-course to measure expression change over 3-4 days was also done in Karpas-299 (high CD25 expressing) and KG-1 cells (low CD25 expressing) under the same conditions, only extending incubation time with Cytarabine.

Results: Incubation with 30 nM Cytarabine was found to have little effect on CD25 mRNA expression in Karpas299 cells over the 72 hour period of the assay. In contrast, the KG-1 cells showed a 2-fold increase in CD25 mRNA expression after 24 hours incubation with Cytarabine, rising to a 4-fold increase in CD25 expression after 48 hours incubation, then gradually falling back to a 3-fold increase after 96 hours incubation.

Measuring the Expression Level of CD25— Surface Protein

Karpas-299 and KG-1 cells were collected after 30 nM Cytarabine treatment for 24 hours, then blocked and stained with directly labelled anti-CD25-PE mAb for 1 hour. Cells were then washed and run on a Fortessa X20 flow cytometer. The mean number of CD25 antibodies bound per cell was calculated using QuantiBRITE-PE reference beads from BD using directly labelled monoclonal mouse anti-human CD25-PE Ab from BD (cat #555432).

Results: Incubation with 30 nM Cytarabine was found to have little effect on CD25 surface protein expression in Karpas299 cells over the 24 hour period of the assay, with both untreated and treated Karpas299 cells binding a mean average of ~60000 antibodies per cell. In contrast, KG-1 cells incubated with 30 nM Cytarabine were found to have significantly increased levels of CD25 surface expression, with untreated KG-1 cells binding a mean average of ~200 antibodies per cell compared to a mean average of ~400 antibodies per cell bound by treated KG-1 cells.

Example 10: Synergy Against CD25+Ve Neoplastic Cells Between ADCxCD25 and Each of the Immunooncology (I/O) Secondary Agents PD1 Antagonists, PDL1 Antagonists, CTLA4 Antagonists, OX40 Agonists, and GITR Agonists PD1 Antagonists To test whether a PBD-based ADC against CD25 combined with a PD1 antagonist shows additive or synergistic effect, the combination is tested in vivo in a syngeneic tumor model in immunocompetent mice (for CD25, potentially suitable models include YAC1, MC38, B16F10, CT26). For this purpose, an antibody cross reactive with mouse CD25 is conjugated to a PBD warhead and this ADC is administered with the PD1 antagonist to mice grafted with a mouse tumor cell line expressing CD25. The ADC is administered before the PD1 antagonist, concomitantly with the PD1 antagonist, or after the PD1 antagonist, as decided by the experimenter.

Typically, the ADC is dosed as a single dose between 0.1 and 1 mg/kg, while the PD1 antagonist is dosed Q3d×3 at doses between 1 and 10 mg/kg. Control groups include the ADC or PD1 antagonist alone. Tumor volumes and body weight is subsequently measured up to 60 days for all groups and the number of partially responding (PR), completely responding (CR) tumor free surviving (TFS mice is determined in each group. Statistical analysis (typically a log-rank test) is performed to determine whether the mice treated with the combination have outperformed the mice treated with either ADC or PD1 antagonist alone.

PDL1 Antagonists

To test whether a PBD-based ADC against CD25 combined with a PDL1 antagonist shows additive or synergistic effect, the combination is tested in vivo in a syngeneic tumor model in immunocompetent mice. For this purpose, an antibody cross reactive with mouse CD25 is conjugated to a PBD warhead and this ADC is administered with the PDL1 antagonist to mice grafted with a mouse tumor cell line expressing CD25. The ADC is administered before the PDL1 antagonist, concomitantly with the PDL1 antagonist, or after the PDL1 antagonist, as decided by the experimenter.

Typically, the ADC is dosed as a single dose between 0.1 and 1 mg/kg, while the PD1 antagonist is dosed Q3d×3 at doses between 1 and 10 mg/kg. Control groups include the ADC or PDL1 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or PDL1 antagonist alone.

CTLA4 Antagonists

To test whether a PBD-based ADC against CD25 combined with a CTLA4 antagonist shows additive or synergistic effect, the combination is tested in vivo in a syngeneic tumor model in immunocompetent mice. For this purpose, an antibody cross reactive with mouse CD25 is conjugated to a PBD warhead and this ADC is administered with the CTLA4 antagonist to mice grafted with a mouse tumor cell line expressing CD25. The ADC is administered before the CTLA4 antagonist, concomitantly with the CTLA4 antagonist, or after the CTLA4 antagonist, as decided by the experimenter.

Typically, the ADC is dosed as a single dose between 0.1 and 1 mg/kg, while the CLTA4 antagonist is dosed Q3d×3 at doses between 1 and 10 mg/kg. Control groups include the ADC or CTLA4 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or CTLA4 antagonist alone.

OX40 Agonists

To test whether a PBD-based ADC against CD25 combined with a OX40 agonist shows additive or synergistic effect, the combination is tested in vivo in a syngeneic tumor model in immunocompetent mice. For this purpose, an antibody cross reactive with mouse CD25 is conjugated to a PBD warhead and this ADC is administered with the OX40 agonist to mice grafted with a mouse tumor cell line expressing CD25. The ADC is administered before the OX40 agonist, concomitantly with the OX40 agonist, or after the OX40 agonist, as decided by the experimenter.

Typically, the ADC is dosed as a single dose between 0.1 and 1 mg/kg, while the OX40 agonist is dosed Q3d×3 at doses between 1 and 10 mg/kg. Control groups include the ADC or OX40 agonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or OX40 agonist alone.

GITR Agonists

To test whether a PBD-based ADC against CD25 combined with a GITR agonist shows additive or synergistic effect, the combination is tested in vivo in a syngeneic tumor model in immunocompetent mice. For this purpose, an antibody cross reactive with mouse CD25 is conjugated to a PBD warhead and this ADC is administered with the GITR agonist to mice grafted with a mouse tumor cell line expressing CD25. The ADC is administered before the GITR agonist, concomitantly with the GITR agonist, or after the GITR agonist, as decided by the experimenter.

Typically, the ADC is dosed as a single dose between 0.1 and 1 mg/kg, while the GITR agonist is dosed Q3d×3 at doses between 1 and 10 mg/kg. Control groups include the ADC or GITR agonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or GITR agonist alone.

Example 11: Synergy Against CD25-Ve Neoplastic Cells Between ADCxCD25 and Each of the Immunoonclogy (I/O) Secondary Agents PD1 Antagonists, PDL1 Antagonists, CTLA4 Antagonists, OX40 Agonists, and GITR Agonists CD25 is also expressed on immune cells that infiltrate the local tumor environment and which can have a suppressive impact on the innate immune response against the tumor. Examples of such cells are T-cells, such as regulatory T-cells. ADCxCD25 can be used to target these immune cells, which will kill the immune suppressive cells, boosting the immune response.

In addition to this 'release of immune suppression' effect, killing of the immune cells by ADCxCD25 will release local PBD warhead will kill neighbouring neoplastic cells via bystander kill.

Accordingly, through these two mechanisms, tumors not expressing CD25 can be killed by targeting immune cells in the local tumor environment. Also, CD25−ve tumor cells killed by PBD released from neighbouring immune cells will induce additional immunogenic cell death, further strengthening the anti-tumor immune response.

PD1 Antagonist

To test whether a PBD-based ADC against CD25 combined with a PD1 antagonist shows additive or synergistic effect against tumors not expressing CD25, the combination is tested in vivo in a syngeneic tumor model in immunocompetent mice. For this purpose, an antibody cross reactive with mouse CD25 is conjugated to a PBD warhead and this ADC is administered with the PD1 antagonist to mice grafted with a mouse tumor cell line know to have high levels of infiltrating lymphocytes, such as but not limited to MC38 and CT26. The ADC is administered before the PD1 antagonist, concomitantly with the PD1 antagonist, or after the PD1 antagonist, as decided by the experimenter.

Typically, the ADC is dosed as a single dose between 0.1 and 1 mg/kg, while the PD1 antagonist is dosed Q3d×3 at doses between 1 and 10 mg/kg. Control groups include the ADC or PD1 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or PD1 antagonist alone PD-L1 Antagonists To test whether a PBD-based ADC against CD25 combined with a PDL1 antagonist shows additive or synergistic effect against tumors not expressing CD25, the combination is tested in vivo in a syngeneic tumor model in immunocompetent mice. For this purpose, an antibody cross reactive with mouse CD25 is conjugated to a PBD warhead and this ADC is administered with the PDL1 antagonist to mice grafted with a mouse tumor cell line know to have high levels of infiltrating lymphocytes, such as but not limited to MC38 and CT26. The ADC is administered before the PDL1 antagonist, concomitantly with the PDL1 antagonist, or after the PDL1 antagonist, as decided by the experimenter.

Typically, the ADC is dosed as a single dose between 0.1 and 1 mg/kg, while the PDL1 antagonist is dosed Q3d×3 at doses between 1 and 10 mg/kg. Control groups include the ADC or PDL1 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or PDL1 antagonist alone.

CTLA4 Antagonists

To test whether a PBD-based ADC against CD25 combined with a CTLA4 antagonist shows additive or synergistic effect against tumors not expressing CD25, the combination is tested in vivo in a syngeneic tumor model in immunocompetent mice. For this purpose, an antibody cross reactive with mouse CD25 is conjugated to a PBD warhead and this ADC is administered with the CTLA4 antagonist to mice grafted with a mouse tumor cell line know to have high levels of infiltrating lymphocytes, such as but not limited to MC38 and CT26. The ADC is administered before the CTLA4 antagonist, concomitantly with the CTLA4 antagonist, or after the CTLA4 antagonist, as decided by the experimenter.

Typically, the ADC is dosed as a single dose between 0.1 and 1 mg/kg, while the CTLA4 antagonist is dosed Q3d×3 at doses between 1 and 10 mg/kg. Control groups include the ADC or CTLA4 antagonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or CTLA4 antagonist alone.

OX40 Agonists

To test whether a PBD-based ADC against CD25 combined with a OX40 agonist shows additive or synergistic effect against tumors not expressing CD25, the combination is tested in vivo in a syngeneic tumor model in immunocompetent mice. For this purpose, an antibody cross reactive with mouse CD25 is conjugated to a PBD warhead and this ADC is administered with the OX40 agonist to mice grafted with a mouse tumor cell line know to have high levels of infiltrating lymphocytes, such as but not limited to MC38 and CT26. The ADC is administered before the OX40 agonist, concomitantly with the OX40 agonist, or after the OX40 agonist, as decided by the experimenter.

Typically, the ADC is dosed as a single dose between 0.1 and 1 mg/kg, while the OX40 agonist is dosed Q3d×3 at doses between 1 and 10 mg/kg. Control groups include the ADC or OX40 agonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or OX40 agonist alone.

GITR Agonists

To test whether a PBD-based ADC against CD25 combined with a GITR agonist shows additive or synergistic effect against tumors not expressing CD25, the combination is tested in vivo in a syngeneic tumor model in immunocompetent mice. For this purpose, an antibody cross reactive with mouse CD25 is conjugated to a PBD warhead and this ADC is administered with the GITR agonist to mice grafted with a mouse tumor cell line know to have high levels of infiltrating lymphocytes, such as but not limited to MC38 and CT26. The ADC is administered before the GITR agonist, concomitantly with the GITR agonist, or after the GITR agonist, as decided by the experimenter.

Typically, the ADC is dosed as a single dose between 0.1 and 1 mg/kg, while the GITR agonist is dosed Q3d×3 at doses between 1 and 10 mg/kg. Control groups include the ADC or GITR agonist alone. Tumor volumes and body weight is subsequently measured up to 60 days for all groups and the number of partially responding (PR), completely responding (CR) tumor free surviving (TFS mice is determined in each group.

Statistical analysis (typically a log-rank test) is performed to determine whether the mice treated with the combination have outperformed the mice treated with either ADC or GITR agonist alone.

The invention claimed is:

1. A method for treating cancer in an individual, the method comprising administering to the individual an effective amount of ADCX25 and a PD1 antagonist; wherein ADCX25 has the following chemical structure:

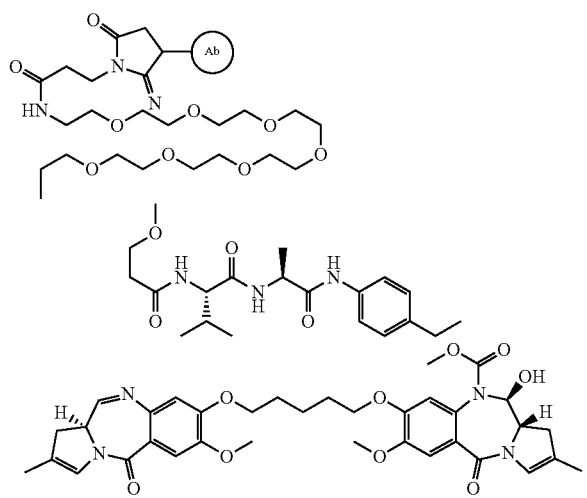

and wherein Ab is an antibody that binds to CD25 which comprises (a) a heavy chain having the amino acid sequence of SEQ ID NO. 1, and (b) a light chain having the amino acid sequence of SEQ ID NO. 2.

2. The method of claim 1, wherein the treatment comprises administering ADCX25 before the PD1 antagonist, simultaneous with the PD1 antagonist, or after the PD1 antagonist.

3. The method of claim 1, wherein the treatment further comprises administering a chemotherapeutic agent.

4. The method of claim 1, wherein the individual is a human.

5. The method of claim 1, wherein the individual has cancer.

6. The method of claim 5, wherein the cancer is characterised by the presence of a neoplasm comprising both CD25+ and CD25− cells.

7. The method of claim 5, wherein the cancer is characterised by the presence of a neoplasm comprising CD25− neoplastic cells.

8. The method of claim 5, wherein the cancer or neoplasm is all or part of a solid tumour.

9. The method of claim 5, wherein the cancer expresses CD25 or CD25+ tumour-associated non-tumour cells.

10. The method of claim 5, wherein the cancer exhibits a low level of surface expression of CD25.

11. The method of claim 5, wherein the cancer is selected from: Hodgkin's and non-Hodgkin's Lymphoma, diffuse large B-cell lymphoma (DLBCL), follicular lymphoma, (FL), Mantle Cell lymphoma (MCL), chronic lymphatic lymphoma (CLL), Marginal Zone B-cell lymphoma (MZBL); Hairy cell leukemia (HCL), Hairy cell leukemia variant (HCL-v), Acute Myeloid Leukaemia (AML), Acute Lymphoblastic Leukaemia (ALL), Philadelphia chromosome-positive ALL (Ph+ALL), Philadelphia chromosome-negative ALL (Ph−ALL); pancreatic cancer, breast cancer, colorectal cancer, gastric cancer, oesophageal cancer, melanoma, non-small cell lung cancer, ovarian cancer, hepatocellular carcinoma, renal cell carcinoma, and head and neck cancer.

12. The method of claim 1, wherein the PD1 antagonist is selected from pembrolizumab, nivolumab, MEDI0680, PDR001 (spartalizumab), Camrelizumab, AUNP12, Pidilizumab Cemiplimab (REGN-2810), AMP-224, BGB-A317 (Tisleizumab), and BGB-108.

13. The method of claim 1, wherein the PD1 antagonist is pembrolizumab.

* * * * *

SEQUENCE LISTING

```
<160> NUMBER OF SEQ ID NOS: 701

<210> SEQ ID NO 1
<211> LENGTH: 122
<212> TYPE: PRT
<213> ORGANISM: Artificial Sequence
<220> FEATURE:
<223> OTHER INFORMATION: AB12 VH

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Arg His Pro Ile Tyr Tyr Thr Tyr Asp Asp Thr Met Asp Tyr Trp
            100                 105                 110

Gly Gln Gly Thr Thr Val Thr Val Ser Ser
        115                 120

<210> SEQ ID NO 2
<211> LENGTH: 119
<212> TYPE: PRT
<213> ORGANISM: Artificial Sequence
<220> FEATURE:
<223> OTHER INFORMATION: AB12 VL

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro
        115

<210> SEQ ID NO 3
<211> LENGTH: 5
<212> TYPE: PRT
<213> ORGANISM: Artificial Sequence
<220> FEATURE:
<223> OTHER INFORMATION: VH CDR1

<400> SEQUENCE: 3

Arg Tyr Ile Ile Asn
1               5

<210> SEQ ID NO 4
<211> LENGTH: 17
<212> TYPE: PRT
<213> ORGANISM: Artificial Sequence
<220> FEATURE:
<223> OTHER INFORMATION: VH CDR2

<400> SEQUENCE: 4

Arg Ile Ile Pro Ile Leu Gly Val Glu Asn Tyr Ala Gln Lys Phe Gln
1               5                   10                  15

Gly

<210> SEQ ID NO 5
<211> LENGTH: 6
<212> TYPE: PRT
<213> ORGANISM: Artificial Sequence
<220> FEATURE:
<223> OTHER INFORMATION: VH CDR3

```
<400> SEQUENCE: 5

Lys Asp Trp Phe Asp Tyr
1               5

<210> SEQ ID NO 6
<211> LENGTH: 11
<212> TYPE: PRT
<213> ORGANISM: Artificial Sequence
<220> FEATURE:
<223> OTHER INFORMATION: VL CDR1

<400> SEQUENCE: 6

Arg Ala Ser Gln Ser Val Ser Ser Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: VL CDR2

<400> SEQUENCE: 7

Gly Ala Ser Ser Arg Ala Thr
1               5

<210> SEQ ID NO 8
<211> LENGTH: 9
<212> TYPE: PRT
<213> ORGANISM: Artificial Sequence
<220> FEATURE:
<223> OTHER INFORMATION: VL CDR3

<400> SEQUENCE: 8

Gln Gln Tyr Gly Ser Ser Pro Leu Thr
1               5

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000
```

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

```
<210> SEQ ID NO 25
<400> SEQUENCE: 25
000

<210> SEQ ID NO 26
<400> SEQUENCE: 26
000

<210> SEQ ID NO 27
<400> SEQUENCE: 27
000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000
```

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

```
<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000
```

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

-continued

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112

<400> SEQUENCE: 112

000

```
<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118
<400> SEQUENCE: 118
000

<210> SEQ ID NO 119
<400> SEQUENCE: 119
000

<210> SEQ ID NO 120
<400> SEQUENCE: 120
000

<210> SEQ ID NO 121
<400> SEQUENCE: 121
000

<210> SEQ ID NO 122
<400> SEQUENCE: 122
000

<210> SEQ ID NO 123
<400> SEQUENCE: 123
000
```

<210> SEQ ID NO 124

<400> SEQUENCE: 124

000

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129

<400> SEQUENCE: 129

000

<210> SEQ ID NO 130

<400> SEQUENCE: 130

000

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151

<400> SEQUENCE: 151

000

<210> SEQ ID NO 152

<400> SEQUENCE: 152

000

<210> SEQ ID NO 153

<400> SEQUENCE: 153

000

<210> SEQ ID NO 154

<400> SEQUENCE: 154

000

<210> SEQ ID NO 155

<400> SEQUENCE: 155

000

<210> SEQ ID NO 156

<400> SEQUENCE: 156

000

```
<210> SEQ ID NO 157
<400> SEQUENCE: 157
000

<210> SEQ ID NO 158
<400> SEQUENCE: 158
000

<210> SEQ ID NO 159
<400> SEQUENCE: 159
000

<210> SEQ ID NO 160
<400> SEQUENCE: 160
000

<210> SEQ ID NO 161
<400> SEQUENCE: 161
000

<210> SEQ ID NO 162
<400> SEQUENCE: 162
000

<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000
```

<210> SEQ ID NO 168

<400> SEQUENCE: 168

000

<210> SEQ ID NO 169

<400> SEQUENCE: 169

000

<210> SEQ ID NO 170

<400> SEQUENCE: 170

000

<210> SEQ ID NO 171

<400> SEQUENCE: 171

000

<210> SEQ ID NO 172

<400> SEQUENCE: 172

000

<210> SEQ ID NO 173

<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

<210> SEQ ID NO 214

<400> SEQUENCE: 214

000

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

```
<210> SEQ ID NO 223
<400> SEQUENCE: 223
000

<210> SEQ ID NO 224
<400> SEQUENCE: 224
000

<210> SEQ ID NO 225
<400> SEQUENCE: 225
000

<210> SEQ ID NO 226
<400> SEQUENCE: 226
000

<210> SEQ ID NO 227
<400> SEQUENCE: 227
000

<210> SEQ ID NO 228
<400> SEQUENCE: 228
000

<210> SEQ ID NO 229
<400> SEQUENCE: 229
000

<210> SEQ ID NO 230
<400> SEQUENCE: 230
000

<210> SEQ ID NO 231
<400> SEQUENCE: 231
000

<210> SEQ ID NO 232
<400> SEQUENCE: 232
000

<210> SEQ ID NO 233
<400> SEQUENCE: 233
000
```

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

```
<210> SEQ ID NO 245
<400> SEQUENCE: 245
000

<210> SEQ ID NO 246
<400> SEQUENCE: 246
000

<210> SEQ ID NO 247
<400> SEQUENCE: 247
000

<210> SEQ ID NO 248
<400> SEQUENCE: 248
000

<210> SEQ ID NO 249
<400> SEQUENCE: 249
000

<210> SEQ ID NO 250
<400> SEQUENCE: 250
000

<210> SEQ ID NO 251
<400> SEQUENCE: 251
000

<210> SEQ ID NO 252
<400> SEQUENCE: 252
000

<210> SEQ ID NO 253
<400> SEQUENCE: 253
000

<210> SEQ ID NO 254
<400> SEQUENCE: 254
000

<210> SEQ ID NO 255
<400> SEQUENCE: 255
000
```

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

-continued

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

```
<210> SEQ ID NO 289
<400> SEQUENCE: 289
000

<210> SEQ ID NO 290
<400> SEQUENCE: 290
000

<210> SEQ ID NO 291
<400> SEQUENCE: 291
000

<210> SEQ ID NO 292
<400> SEQUENCE: 292
000

<210> SEQ ID NO 293
<400> SEQUENCE: 293
000

<210> SEQ ID NO 294
<400> SEQUENCE: 294
000

<210> SEQ ID NO 295
<400> SEQUENCE: 295
000

<210> SEQ ID NO 296
<400> SEQUENCE: 296
000

<210> SEQ ID NO 297
<400> SEQUENCE: 297
000

<210> SEQ ID NO 298
<400> SEQUENCE: 298
000

<210> SEQ ID NO 299
<400> SEQUENCE: 299
000

<210> SEQ ID NO 300
<211> LENGTH: 7
```

```
<212> TYPE: PRT
<213> ORGANISM: Artificial Sequence
<220> FEATURE:
<223> OTHER INFORMATION: AUNP12 peptide

<400> SEQUENCE: 300

Phe Ser Glu Ser Thr Asn Ser
1               5

<210> SEQ ID NO 301
<211> LENGTH: 7
<212> TYPE: PRT
<213> ORGANISM: Artificial Sequence
<220> FEATURE:
<223> OTHER INFORMATION: AUNP12 peptide

<400> SEQUENCE: 301

Ser Asn Thr Ser Glu Ser Phe
1               5

<210> SEQ ID NO 302
<211> LENGTH: 14
<212> TYPE: PRT
<213> ORGANISM: Artificial Sequence
<220> FEATURE:
<223> OTHER INFORMATION: AUNP12 peptide

<400> SEQUENCE: 302

Phe Arg Val Thr Gln Leu Ala Pro Lys Ala Gln Ile Lys Glu
1               5                   10

<210> SEQ ID NO 303
<211> LENGTH: 22
<212> TYPE: PRT
<213> ORGANISM: Artificial Sequence
<220> FEATURE:
<223> OTHER INFORMATION: AUNP12 peptide

<400> SEQUENCE: 303

Ser Asn Thr Ser Glu Ser Phe Lys Phe Arg Val Thr Gln Leu Ala Pro
1               5                   10                  15

Lys Ala Gln Ile Lys Glu
            20

<210> SEQ ID NO 304

<400> SEQUENCE: 304

000

<210> SEQ ID NO 305

<400> SEQUENCE: 305

000

<210> SEQ ID NO 306

<400> SEQUENCE: 306

000

<210> SEQ ID NO 307

<400> SEQUENCE: 307

000
```

-continued

<210> SEQ ID NO 308

<400> SEQUENCE: 308

000

<210> SEQ ID NO 309

<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

```
<210> SEQ ID NO 319
<400> SEQUENCE: 319
000

<210> SEQ ID NO 320
<400> SEQUENCE: 320
000

<210> SEQ ID NO 321
<400> SEQUENCE: 321
000

<210> SEQ ID NO 322
<400> SEQUENCE: 322
000

<210> SEQ ID NO 323
<400> SEQUENCE: 323
000

<210> SEQ ID NO 324
<400> SEQUENCE: 324
000

<210> SEQ ID NO 325
<400> SEQUENCE: 325
000

<210> SEQ ID NO 326
<400> SEQUENCE: 326
000

<210> SEQ ID NO 327
<400> SEQUENCE: 327
000

<210> SEQ ID NO 328
<400> SEQUENCE: 328
000

<210> SEQ ID NO 329
<400> SEQUENCE: 329
000
```

```
<210> SEQ ID NO 330
<400> SEQUENCE: 330
000

<210> SEQ ID NO 331
<400> SEQUENCE: 331
000

<210> SEQ ID NO 332
<400> SEQUENCE: 332
000

<210> SEQ ID NO 333
<400> SEQUENCE: 333
000

<210> SEQ ID NO 334
<400> SEQUENCE: 334
000

<210> SEQ ID NO 335
<400> SEQUENCE: 335
000

<210> SEQ ID NO 336
<400> SEQUENCE: 336
000

<210> SEQ ID NO 337
<400> SEQUENCE: 337
000

<210> SEQ ID NO 338
<400> SEQUENCE: 338
000

<210> SEQ ID NO 339
<400> SEQUENCE: 339
000

<210> SEQ ID NO 340
<400> SEQUENCE: 340
000
```

```
<210> SEQ ID NO 341
<400> SEQUENCE: 341
000

<210> SEQ ID NO 342
<400> SEQUENCE: 342
000

<210> SEQ ID NO 343
<400> SEQUENCE: 343
000

<210> SEQ ID NO 344
<400> SEQUENCE: 344
000

<210> SEQ ID NO 345
<400> SEQUENCE: 345
000

<210> SEQ ID NO 346
<400> SEQUENCE: 346
000

<210> SEQ ID NO 347
<400> SEQUENCE: 347
000

<210> SEQ ID NO 348
<400> SEQUENCE: 348
000

<210> SEQ ID NO 349
<400> SEQUENCE: 349
000

<210> SEQ ID NO 350
<400> SEQUENCE: 350
000

<210> SEQ ID NO 351
<400> SEQUENCE: 351
000
```

-continued

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

-continued

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

```
<210> SEQ ID NO 385
<400> SEQUENCE: 385
000

<210> SEQ ID NO 386
<400> SEQUENCE: 386
000

<210> SEQ ID NO 387
<400> SEQUENCE: 387
000

<210> SEQ ID NO 388
<400> SEQUENCE: 388
000

<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392
<400> SEQUENCE: 392
000

<210> SEQ ID NO 393
<400> SEQUENCE: 393
000

<210> SEQ ID NO 394
<400> SEQUENCE: 394
000

<210> SEQ ID NO 395
<400> SEQUENCE: 395
000
```

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400
<211> LENGTH: 5
<212> TYPE: PRT
<213> ORGANISM: Artificial Sequence
<220> FEATURE:
<223> OTHER INFORMATION: BMS-936559/MDX-1105 Antibody 1 VH CDR1

<400> SEQUENCE: 400

Asp Tyr Gly Phe Ser
1               5

<210> SEQ ID NO 401
<211> LENGTH: 17
<212> TYPE: PRT
<213> ORGANISM: Artificial Sequence
<220> FEATURE:
<223> OTHER INFORMATION: BMS-936559/MDX-1105 Antibody 1 VH CDR2

<400> SEQUENCE: 401

Trp Ile Thr Ala Tyr Asn Gly Asn Thr Asn Tyr Ala Gln Lys Leu Gln
1               5                   10                  15

Gly

<210> SEQ ID NO 402
<211> LENGTH: 8
<212> TYPE: PRT
<213> ORGANISM: Artificial Sequence
<220> FEATURE:
<223> OTHER INFORMATION: BMS-936559/MDX-1105 Antibody 1 VH CDR3

<400> SEQUENCE: 402

Asp Tyr Phe Tyr Gly Met Asp Val
1               5

<210> SEQ ID NO 403
<211> LENGTH: 11
<212> TYPE: PRT
<213> ORGANISM: Artificial Sequence
<220> FEATURE:
<223> OTHER INFORMATION: BMS-936559/MDX-1105 Antibody 1 VL CDR1

```
<400> SEQUENCE: 403

Arg Ala Ser Gln Ser Val Ser Ser Tyr Leu Val
1               5                   10

<210> SEQ ID NO 404
<211> LENGTH: 7
<212> TYPE: PRT
<213> ORGANISM: Artificial Sequence
<220> FEATURE:
<223> OTHER INFORMATION: BMS-936559/MDX-1105 Antibody 1 VL CDR2

<400> SEQUENCE: 404

Asp Ala Ser Asn Arg Ala Thr
1               5

<210> SEQ ID NO 405
<211> LENGTH: 9
<212> TYPE: PRT
<213> ORGANISM: Artificial Sequence
<220> FEATURE:
<223> OTHER INFORMATION: BMS-936559/MDX-1105 Antibody 1 VL CDR3

<400> SEQUENCE: 405

Gln Gln Arg Ser Asn Trp Pro Arg Thr
1               5

<210> SEQ ID NO 406
<211> LENGTH: 5
<212> TYPE: PRT
<213> ORGANISM: Artificial Sequence
<220> FEATURE:
<223> OTHER INFORMATION: BMS-936559/MDX-1105 Antibody 2 VH CDR1

<400> SEQUENCE: 406

Thr Tyr Ala Ile Ser
1               5

<210> SEQ ID NO 407
<211> LENGTH: 17
<212> TYPE: PRT
<213> ORGANISM: Artificial Sequence
<220> FEATURE:
<223> OTHER INFORMATION: BMS-936559/MDX-1105 Antibody 2  VH CDR2

<400> SEQUENCE: 407

Gly Ile Ile Pro Ile Phe Gly Lys Ala His Tyr Ala Gln Lys Phe Gln
1               5                   10                  15

Gly

<210> SEQ ID NO 408
<211> LENGTH: 14
<212> TYPE: PRT
<213> ORGANISM: Artificial Sequence
<220> FEATURE:
<223> OTHER INFORMATION: BMS-936559/MDX-1105 Antibody 2  VH CDR3

<400> SEQUENCE: 408

Lys Phe His Phe Val Ser Gly Ser Pro Phe Gly Met Asp Val
1               5                   10

<210> SEQ ID NO 409
<211> LENGTH: 11
<212> TYPE: PRT
<213> ORGANISM: Artificial Sequence
<220> FEATURE:
```

```
<223> OTHER INFORMATION: BMS-936559/MDX-1105 Antibody 2 VL CDR1

<400> SEQUENCE: 409

Arg Ala Ser Gln Ser Val Ser Ser Tyr Leu Ala
1               5                   10

<210> SEQ ID NO 410
<211> LENGTH: 7
<212> TYPE: PRT
<213> ORGANISM: Artificial Sequence
<220> FEATURE:
<223> OTHER INFORMATION: BMS-936559/MDX-1105 Antibody 2 VL CDR2

<400> SEQUENCE: 410

Asp Ala Ser Asn Arg Ala Thr
1               5

<210> SEQ ID NO 411
<211> LENGTH: 8
<212> TYPE: PRT
<213> ORGANISM: Artificial Sequence
<220> FEATURE:
<223> OTHER INFORMATION: BMS-936559/MDX-1105 Antibody 2 VL CDR3

<400> SEQUENCE: 411

Gln Gln Arg Ser Asn Trp Pro Thr
1               5

<210> SEQ ID NO 412
<211> LENGTH: 5
<212> TYPE: PRT
<213> ORGANISM: Artificial Sequence
<220> FEATURE:
<223> OTHER INFORMATION: BMS-936559/MDX-1105 Antibody 3 VH CDR1

<400> SEQUENCE: 412

Ser Tyr Asp Val His
1               5

<210> SEQ ID NO 413
<211> LENGTH: 17
<212> TYPE: PRT
<213> ORGANISM: Artificial Sequence
<220> FEATURE:
<223> OTHER INFORMATION: BMS-936559/MDX-1105 Antibody 3 VH CDR2

<400> SEQUENCE: 413

Trp Leu His Ala Asp Thr Gly Ile Thr Lys Phe Ser Gln Lys Phe Gln
1               5                   10                  15

Gly

<210> SEQ ID NO 414
<211> LENGTH: 9
<212> TYPE: PRT
<213> ORGANISM: Artificial Sequence
<220> FEATURE:
<223> OTHER INFORMATION: BMS-936559/MDX-1105 Antibody 3 VH CDR3

<400> SEQUENCE: 414

Glu Arg Ile Gln Leu Trp Phe Asp Tyr
1               5

<210> SEQ ID NO 415
<211> LENGTH: 11
<212> TYPE: PRT
<213> ORGANISM: Artificial Sequence
```

```
<220> FEATURE:
<223> OTHER INFORMATION: BMS-936559/MDX-1105 Antibody 3 VL CDR1

<400> SEQUENCE: 415

Arg Ala Ser Gln Gly Ile Ser Ser Trp Leu Ala
1               5                   10

<210> SEQ ID NO 416
<211> LENGTH: 7
<212> TYPE: PRT
<213> ORGANISM: Artificial Sequence
<220> FEATURE:
<223> OTHER INFORMATION: BMS-936559/MDX-1105 Antibody 3 VL CDR2

<400> SEQUENCE: 416

Ala Ala Ser Ser Leu Gln Ser
1               5

<210> SEQ ID NO 417
<211> LENGTH: 9
<212> TYPE: PRT
<213> ORGANISM: Artificial Sequence
<220> FEATURE:
<223> OTHER INFORMATION: BMS-936559/MDX-1105 Antibody 3 VL CDR3

<400> SEQUENCE: 417

Gln Gln Tyr Asn Ser Tyr Pro Tyr Thr
1               5

<210> SEQ ID NO 418
<211> LENGTH: 121
<212> TYPE: PRT
<213> ORGANISM: Artificial Sequence
<220> FEATURE:
<223> OTHER INFORMATION: durvalumab/MEDI4736 VH Sequence

<400> SEQUENCE: 418

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Gly Trp Phe Gly Glu Leu Ala Phe Asp Tyr Trp Gly
            100                 105                 110

Gln Gly Thr Leu Val Thr Val Ser Ser
        115                 120

<210> SEQ ID NO 419
<211> LENGTH: 108
<212> TYPE: PRT
<213> ORGANISM: Artificial Sequence
<220> FEATURE:
<223> OTHER INFORMATION: durvalumab/MEDI4736 VL Sequence
```

<400> SEQUENCE: 419

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Arg Val Ser Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Leu Pro
                85                  90                  95

Trp Thr Phe Gly Gln Gly Thr Lys Val Glu Ile Lys
            100                 105
```

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

-continued

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

```
<210> SEQ ID NO 461
<400> SEQUENCE: 461
000

<210> SEQ ID NO 462
<400> SEQUENCE: 462
000

<210> SEQ ID NO 463
<400> SEQUENCE: 463
000

<210> SEQ ID NO 464
<400> SEQUENCE: 464
000

<210> SEQ ID NO 465
<400> SEQUENCE: 465
000

<210> SEQ ID NO 466
<400> SEQUENCE: 466
000

<210> SEQ ID NO 467
<400> SEQUENCE: 467
000

<210> SEQ ID NO 468
<400> SEQUENCE: 468
000

<210> SEQ ID NO 469
<400> SEQUENCE: 469
000

<210> SEQ ID NO 470
<400> SEQUENCE: 470
000

<210> SEQ ID NO 471
<400> SEQUENCE: 471
000
```

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

```
<210> SEQ ID NO 483
<400> SEQUENCE: 483
000

<210> SEQ ID NO 484
<400> SEQUENCE: 484
000

<210> SEQ ID NO 485
<400> SEQUENCE: 485
000

<210> SEQ ID NO 486
<400> SEQUENCE: 486
000

<210> SEQ ID NO 487
<400> SEQUENCE: 487
000

<210> SEQ ID NO 488
<400> SEQUENCE: 488
000

<210> SEQ ID NO 489
<400> SEQUENCE: 489
000

<210> SEQ ID NO 490
<400> SEQUENCE: 490
000

<210> SEQ ID NO 491
<400> SEQUENCE: 491
000

<210> SEQ ID NO 492
<400> SEQUENCE: 492
000

<210> SEQ ID NO 493
<400> SEQUENCE: 493
000
```

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500
<211> LENGTH: 107
<212> TYPE: PRT
<213> ORGANISM: Artificial Sequence
<220> FEATURE:
<223> OTHER INFORMATION: TRX518 VL seuqence

<400> SEQUENCE: 500

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Thr Asn
            20                  25                  30

Val Ala Trp Tyr Gln Gln Lys Pro Gly Gln Ala Pro Arg Leu Leu Ile
        35                  40                  45

Tyr Ser Ala Ser Tyr Arg Tyr Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Thr Asp Pro Leu
                85                  90                  95

Thr Phe Gly Gly Gly Thr Lys Val Glu Ile Lys
            100                 105

<210> SEQ ID NO 501
<211> LENGTH: 118
<212> TYPE: PRT
<213> ORGANISM: Artificial Sequence

```
<220> FEATURE:
<223> OTHER INFORMATION: TRX518 VH sequence

<400> SEQUENCE: 501

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser
        115

<210> SEQ ID NO 502
<211> LENGTH: 118
<212> TYPE: PRT
<213> ORGANISM: Artificial Sequence
<220> FEATURE:
<223> OTHER INFORMATION: TRX518 VH sequence

<400> SEQUENCE: 502

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Tyr Tyr Gln Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Arg Arg Tyr Phe Pro Phe Ala Tyr Trp Gly Gln Gly
            100                 105                 110

Thr Leu Val Thr Val Ser
        115

<210> SEQ ID NO 503

<400> SEQUENCE: 503

000

<210> SEQ ID NO 504

<400> SEQUENCE: 504

000
```

```
<210> SEQ ID NO 505
<400> SEQUENCE: 505
000

<210> SEQ ID NO 506
<400> SEQUENCE: 506
000

<210> SEQ ID NO 507
<400> SEQUENCE: 507
000

<210> SEQ ID NO 508
<400> SEQUENCE: 508
000

<210> SEQ ID NO 509
<400> SEQUENCE: 509
000

<210> SEQ ID NO 510
<400> SEQUENCE: 510
000

<210> SEQ ID NO 511
<400> SEQUENCE: 511
000

<210> SEQ ID NO 512
<400> SEQUENCE: 512
000

<210> SEQ ID NO 513
<400> SEQUENCE: 513
000

<210> SEQ ID NO 514
<400> SEQUENCE: 514
000

<210> SEQ ID NO 515
<400> SEQUENCE: 515
000
```

```
<210> SEQ ID NO 516
<400> SEQUENCE: 516
000

<210> SEQ ID NO 517
<400> SEQUENCE: 517
000

<210> SEQ ID NO 518
<400> SEQUENCE: 518
000

<210> SEQ ID NO 519
<400> SEQUENCE: 519
000

<210> SEQ ID NO 520
<400> SEQUENCE: 520
000

<210> SEQ ID NO 521
<400> SEQUENCE: 521
000

<210> SEQ ID NO 522
<400> SEQUENCE: 522
000

<210> SEQ ID NO 523
<400> SEQUENCE: 523
000

<210> SEQ ID NO 524
<400> SEQUENCE: 524
000

<210> SEQ ID NO 525
<400> SEQUENCE: 525
000

<210> SEQ ID NO 526
<400> SEQUENCE: 526
000
```

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

-continued

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

```
<210> SEQ ID NO 560
<400> SEQUENCE: 560
000

<210> SEQ ID NO 561
<400> SEQUENCE: 561
000

<210> SEQ ID NO 562
<400> SEQUENCE: 562
000

<210> SEQ ID NO 563
<400> SEQUENCE: 563
000

<210> SEQ ID NO 564
<400> SEQUENCE: 564
000

<210> SEQ ID NO 565
<400> SEQUENCE: 565
000

<210> SEQ ID NO 566
<400> SEQUENCE: 566
000

<210> SEQ ID NO 567
<400> SEQUENCE: 567
000

<210> SEQ ID NO 568
<400> SEQUENCE: 568
000

<210> SEQ ID NO 569
<400> SEQUENCE: 569
000

<210> SEQ ID NO 570
<400> SEQUENCE: 570
000
```

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600
<211> LENGTH: 450
<212> TYPE: PRT
<213> ORGANISM: Artificial Sequence
<220> FEATURE:
<223> OTHER INFORMATION: MEDI0562 Heavy chain sequence

<400> SEQUENCE: 600

```
Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
                85                  90                  95
```

```
Arg Tyr Lys Tyr Asp Tyr Asp Gly Gly His Ala Met Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
            210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly
    450

<210> SEQ ID NO 601
<211> LENGTH: 214
<212> TYPE: PRT
<213> ORGANISM: Artificial Sequence
<220> FEATURE:
<223> OTHER INFORMATION: MEDI0562 Light Chain sequence
```

```
<400> SEQUENCE: 601

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 602
<211> LENGTH: 402
<212> TYPE: PRT
<213> ORGANISM: Artificial Sequence
<220> FEATURE:
<223> OTHER INFORMATION: MEDI6383

<400> SEQUENCE: 602

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125
```

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Asp Gln Asp Lys Ile Glu Ala Leu Ser Ser Lys
225                 230                 235                 240

Val Gln Gln Leu Glu Arg Ser Ile Gly Leu Lys Asp Leu Ala Met Ala
                245                 250                 255

Asp Leu Glu Gln Lys Val Leu Glu Met Glu Ala Ser Thr Gln Val Ser
            260                 265                 270

His Arg Tyr Pro Arg Ile Gln Ser Ile Lys Val Gln Phe Thr Glu Tyr
        275                 280                 285

Lys Lys Glu Lys Gly Phe Ile Leu Thr Ser Gln Lys Glu Asp Glu Ile
290                 295                 300

Met Lys Val Gln Asn Asn Ser Val Ile Ile Asn Cys Asp Gly Phe Tyr
305                 310                 315                 320

Leu Ile Ser Leu Lys Gly Tyr Phe Ser Gln Glu Val Asn Ile Ser Leu
                325                 330                 335

His Tyr Gln Lys Asp Glu Glu Pro Leu Phe Gln Leu Lys Lys Val Arg
            340                 345                 350

Ser Val Asn Ser Leu Met Val Ala Ser Leu Thr Tyr Lys Asp Lys Val
        355                 360                 365

Tyr Leu Asn Val Thr Thr Asp Asn Thr Ser Leu Asp Asp Phe His Val
370                 375                 380

Asn Gly Gly Glu Leu Ile Leu Ile His Gln Asn Pro Gly Glu Phe Cys
385                 390                 395                 400

Val Leu

<210> SEQ ID NO 603
<211> LENGTH: 121
<212> TYPE: PRT
<213> ORGANISM: Artificial Sequence
<220> FEATURE:
<223> OTHER INFORMATION: Ox40mAb24 VH sequence

<400> SEQUENCE: 603

Gln Val Gln Leu Gln Glu Ser Gly Pro Gly Leu Val Lys Pro Ser Gln
1               5                   10                  15

Thr Leu Ser Leu Thr Cys Ala Val Tyr Gly Gly Ser Phe Ser Ser Gly
            20                  25                  30

Tyr Trp Asn Trp Ile Arg Lys His Pro Gly Lys Gly Leu Glu Tyr Ile
        35                  40                  45

Gly Tyr Ile Ser Tyr Asn Gly Ile Thr Tyr His Asn Pro Ser Leu Lys
    50                  55                  60

Ser Arg Ile Thr Ile Asn Arg Asp Thr Ser Lys Asn Gln Tyr Ser Leu
65                  70                  75                  80

Gln Leu Asn Ser Val Thr Pro Glu Asp Thr Ala Val Tyr Tyr Cys Ala
            85                  90                  95

Arg Tyr Lys Tyr Asp Tyr Asp Gly Gly His Ala Met Asp Tyr Trp Gly
            100                 105                 110

Gln Gly Thr Leu Val Thr Val Ser Ser
        115                 120

<210> SEQ ID NO 604
<211> LENGTH: 107
<212> TYPE: PRT
<213> ORGANISM: Artificial Sequence
<220> FEATURE:
<223> OTHER INFORMATION: OX40mAb24 VL sequence

<400> SEQUENCE: 604

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Ser Ala Leu Pro Trp
                85                  90                  95

Thr Phe Gly Gln Gly Thr Lys Val Glu Ile Lys
            100                 105

<210> SEQ ID NO 605
<211> LENGTH: 5
<212> TYPE: PRT
<213> ORGANISM: Artificial Sequence
<220> FEATURE:
<223> OTHER INFORMATION: INCAGN1949 Antibody a VH CDR1

<400> SEQUENCE: 605

Gly Ser Ala Met His
1               5

<210> SEQ ID NO 606
<211> LENGTH: 19
<212> TYPE: PRT
<213> ORGANISM: Artificial Sequence
<220> FEATURE:
<223> OTHER INFORMATION: INCAGN1949 Antibody a VH CDR2

<400> SEQUENCE: 606

Arg Ile Arg Ser Lys Ala Asn Ser Tyr Ala Thr Ala Tyr Ala Ala Ser
1               5                   10                  15

Val Lys Gly

<210> SEQ ID NO 607
<211> LENGTH: 10
<212> TYPE: PRT
<213> ORGANISM: Artificial Sequence
<220> FEATURE:
<223> OTHER INFORMATION: INCAGN1949 Antibody a VH CDR3

```
<400> SEQUENCE: 607

Gly Ile Tyr Asp Ser Ser Gly Tyr Asp Tyr
1               5                   10

<210> SEQ ID NO 608
<211> LENGTH: 16
<212> TYPE: PRT
<213> ORGANISM: Artificial Sequence
<220> FEATURE:
<223> OTHER INFORMATION: INCAGN1949 Antibody a VL CDR1

<400> SEQUENCE: 608

Arg Ser Ser Gln Ser Leu Leu His Ser Asn Gly Tyr Asn Tyr Leu Asp
1               5                   10                  15

<210> SEQ ID NO 609
<211> LENGTH: 7
<212> TYPE: PRT
<213> ORGANISM: Artificial Sequence
<220> FEATURE:
<223> OTHER INFORMATION: INCAGN1949 Antibody a VL CDR2

<400> SEQUENCE: 609

Leu Gly Ser Asn Arg Ala Ser
1               5

<210> SEQ ID NO 610
<211> LENGTH: 9
<212> TYPE: PRT
<213> ORGANISM: Artificial Sequence
<220> FEATURE:
<223> OTHER INFORMATION: INCAGN1949 Antibody a VL CDR3

<400> SEQUENCE: 610

Met Gln Ala Leu Gln Thr Pro Leu Thr
1               5

<210> SEQ ID NO 611
<211> LENGTH: 121
<212> TYPE: PRT
<213> ORGANISM: Artificial Sequence
<220> FEATURE:
<223> OTHER INFORMATION: INCAGN1949 Antibody b VH sequence

<400> SEQUENCE: 611

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Ala Met His Trp Val Arg Gln Ala Ser Gly Lys Gly Leu Glu Trp Val
        35                  40                  45

Gly Arg Ile Arg Ser Lys Ala Asn Ser Tyr Ala Thr Ala Tyr Ala Ala
    50                  55                  60

Ser Val Lys Gly Arg Phe Thr Ile Ser Arg Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Ser Gly Ile Tyr Asp Ser Ser Gly Tyr Asp Tyr Trp Gly
            100                 105                 110

Gln Gly Thr Leu Val Thr Val Ser Ser
        115                 120
```

<210> SEQ ID NO 612
<211> LENGTH: 112
<212> TYPE: PRT
<213> ORGANISM: Artificial Sequence
<220> FEATURE:
<223> OTHER INFORMATION: INCAGN1949 Antibody b VL sequence

<400> SEQUENCE: 612

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 613

<400> SEQUENCE: 613

000

<210> SEQ ID NO 614

<400> SEQUENCE: 614

000

<210> SEQ ID NO 615

<400> SEQUENCE: 615

000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

```
<210> SEQ ID NO 631
<400> SEQUENCE: 631
000

<210> SEQ ID NO 632
<400> SEQUENCE: 632
000

<210> SEQ ID NO 633
<400> SEQUENCE: 633
000

<210> SEQ ID NO 634
<400> SEQUENCE: 634
000

<210> SEQ ID NO 635
<400> SEQUENCE: 635
000

<210> SEQ ID NO 636
<400> SEQUENCE: 636
000

<210> SEQ ID NO 637
<400> SEQUENCE: 637
000

<210> SEQ ID NO 638
<400> SEQUENCE: 638
000

<210> SEQ ID NO 639
<400> SEQUENCE: 639
000

<210> SEQ ID NO 640
<400> SEQUENCE: 640
000

<210> SEQ ID NO 641
<400> SEQUENCE: 641
000
```

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

<210> SEQ ID NO 688

<400> SEQUENCE: 688

000

<210> SEQ ID NO 689

<400> SEQUENCE: 689

000

<210> SEQ ID NO 690

<400> SEQUENCE: 690

000

<210> SEQ ID NO 691

<400> SEQUENCE: 691

000

<210> SEQ ID NO 692

<400> SEQUENCE: 692

000

<210> SEQ ID NO 693

<400> SEQUENCE: 693

000

<210> SEQ ID NO 694

<400> SEQUENCE: 694

000

<210> SEQ ID NO 695

<400> SEQUENCE: 695

000

<210> SEQ ID NO 696

<400> SEQUENCE: 696

000

<210> SEQ ID NO 697

<400> SEQUENCE: 697

000

<210> SEQ ID NO 698

<400> SEQUENCE: 698

000

<210> SEQ ID NO 699

<400> SEQUENCE: 699

000

<210> SEQ ID NO 700
<211> LENGTH: 167
<212> TYPE: PRT
<213> ORGANISM: Artificial Sequence
<220> FEATURE:
<223> OTHER INFORMATION: Tremelimumab VH sequence

<400> SEQUENCE: 700

Gly Val Val Gln Pro Gly Arg Ser Leu Arg Leu Ser Cys Ala Ala Ser
1               5                   10                  15

Gly Phe Thr Phe Ser Ser Tyr Gly Met His Trp Val Arg Gln Ala Pro
            20                  25                  30

Gly Lys Gly Leu Glu Trp Val Ala Val Ile Trp Tyr Asp Gly Ser Asn
        35                  40                  45

Lys Tyr Tyr Ala Asp Ser Val Lys Gly Arg Phe Thr Ile Ser Arg Asp
50                  55                  60

Asn Ser Lys Asn Thr Leu Tyr Leu Gln Met Asn Ser Leu Arg Ala Glu
65                  70                  75                  80

Asp Thr Ala Val Tyr Tyr Cys Ala Arg Asp Pro Arg Gly Ala Thr Leu
                85                  90                  95

Tyr Tyr Tyr Tyr Tyr Gly Met Asp Val Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His
                165

<210> SEQ ID NO 701
<211> LENGTH: 139
<212> TYPE: PRT
<213> ORGANISM: Artificial Sequence
<220> FEATURE:
<223> OTHER INFORMATION: Tremelimumab VL sequence

<400> SEQUENCE: 701

Pro Ser Ser Leu Ser Ala Ser Val Gly Asp Arg Val Thr Ile Thr Cys
1               5                   10                  15

Arg Ala Ser Gln Ser Ile Asn Ser Tyr Leu Asp Trp Tyr Gln Gln Lys
            20                  25                  30

```
Pro Gly Lys Ala Pro Lys Leu Leu Ile Tyr Ala Ala Ser Ser Leu Gln
        35              40              45
Ser Gly Val Pro Ser Arg Phe Ser Gly Ser Gly Thr Asp Phe
    50              55              60
Thr Leu Thr Ile Ser Ser Leu Gln Pro Glu Asp Phe Ala Thr Tyr Tyr
65                  70              75              80
Cys Gln Gln Tyr Tyr Ser Thr Pro Phe Thr Phe Gly Pro Gly Thr Lys
                85              90              95
Val Glu Ile Lys Arg Thr Val Ala Ala Pro Ser Val Phe Ile Phe Pro
            100             105             110
Pro Ser Asp Glu Gln Leu Lys Ser Gly Thr Ala Ser Val Val Cys Leu
        115             120             125
Leu Asn Asn Phe Tyr Pro Arg Glu Ala Lys Val
        130             135
```